US007342148B2

(12) United States Patent
Takagi et al.

(10) Patent No.: US 7,342,148 B2
(45) Date of Patent: Mar. 11, 2008

(54) GENE AND PEPTIDE FOR TRANSCRIPTIONAL REPRESSOR

(75) Inventors: Masaru Takagi, Ibaraki (JP); Keiichirou Hiratsu, Ibaraki (JP)

(73) Assignees: National Institute of Advanced Industrial Science and Technology, Chiyoda-ku (JP); GreenSogna, Inc., Ibaraki (JP)

( * ) Notice: Subject to any disclaimer, the term of this patent is extended or adjusted under 35 U.S.C. 154(b) by 288 days.

(21) Appl. No.: 10/500,361

(22) PCT Filed: Dec. 24, 2002

(86) PCT No.: PCT/JP02/13443

§ 371 (c)(1),
(2), (4) Date: Jun. 28, 2004

(87) PCT Pub. No.: WO03/055903

PCT Pub. Date: Jul. 10, 2003

(65) Prior Publication Data

US 2005/0183169 A1    Aug. 18, 2005

(30) Foreign Application Priority Data

| Dec. 26, 2001 | (JP) | ............................. 2001-395487 |
| Dec. 26, 2001 | (JP) | ............................. 2001-395488 |
| May 31, 2002 | (JP) | ............................. 2002-160671 |

(51) Int. Cl.
  A01H 9/00     (2006.01)
  C07H 21/02    (2006.01)
  C07K 14/00    (2006.01)
(52) U.S. Cl. .................. 800/295; 435/320.1; 435/325; 530/300; 536/23.1
(58) Field of Classification Search ................ 530/350, 530/300; 435/320.1, 252.2, 325, 410; 800/295
  See application file for complete search history.

(56) References Cited

U.S. PATENT DOCUMENTS 6,215,043 B1 * 4/2001 Takatsuji et al. ........... 800/290

FOREIGN PATENT DOCUMENTS

| JP | 2001269179 | 10/2001 |
| JP | 2001292776 | 10/2001 |
| JP | 2001292777 | 10/2001 |
| JP | 20011269176 | 10/2001 |
| JP | 20011269177 | 10/2001 |
| JP | 2001269178 | 10/2002 |
| WO | WO93/21337 A | 10/1993 |
| WO | WO 00/47754 | 8/2000 |
| WO | WO 00/52467 A | 9/2000 |
| WO | WO 02/061087 A | 8/2002 |

OTHER PUBLICATIONS

Sato et al. 2000; Structural analysis of *Arabidopsis thaliana* chromosome 3. Sequence features of the regions of 4,504,864 bp covered by sixty P1 and Tac clones. DNA Res. 7: 131-135.*
Hiratsu et al. 2004 ; Identification of the minimal repression domain in SUPERMAN shows that the DLELRL hexapeptide is both necessary and sufficient for repression of transcription in *Arabidopsis*. Biochem. Biophys, Res. Commun. 321:172-178.*
Masaur Ohta et al., Repression Domains of Class II ERF Transcriptional Repressors Share an Esstential Motif for Active Repression, The Plant Cell, vol. 13, 1959-1968, Aug. 2001, www.plantcell.org@2001American Society of Plant Biologists.
Supplementary Partial European Search Report of EP 02 79 0848.
Database CA Online! Chemical Abstracts Service, Columbus Ohio US; Scott D. Barry et al., "Novel and Complex Chromosomal Arrangement of Rhizobium Loti Nodulation Genes", XP002319791 *Abstract.
Hajime Sakai et al., "Role of Superman in maintaining *Arabidopsis* floral whorl boundaries", Nature, vol. 378, Nov. 9, 1995, pp. 199-203.
Kyoko Matsui et al., "Functional Analysis of the ERF transcription factors in plants", American Society of Plant Biologists, Aug. 2002, Abstract.
Masaru Ohta et al., "Three ethylene-responsive transcription factors in tobacco with distinct transactivation functions", The Plant Journal, (2000) 22(1), pp. 29-38.
Keiichiro Hiratsu et al., "The SUPERMAN protein is an active repressor whose carboxy-terminal repression domain is required for the development of normal flowers", FEBS Letters 514 (2002) 351-354.
Keiichiro Hiratsu et al., "Identification of the minimal repression domain of SUPERMAN shows that the DLELRL hexapeptide is both necessary and sufficient for repression of transcription in *Arabidopsis*", Biochemical and Biophysical Research Communications, 321 (2004) pp. 172-178.
Plant and Cell Physiology, vol. 39, no. suppl., May 3, 1998, pp. S63, XP001076676, JP Japanese Society of Plant Physiology, "the whole document".

* cited by examiner

*Primary Examiner*—Karen Cochrane Carlson
(74) *Attorney, Agent, or Firm*—Foley & Lardner LLP

(57) ABSTRACT

This invention relates to a peptide or protein capable of converting a transcription factor into a transcriptional repressor, a gene encoding such peptide or protein, a chimeric protein in which the aforementioned peptide or protein is fused to a transcription factor, a chimeric gene in which the gene encoding a peptide or protein is fused to a gene encoding a transcription factor, a recombinant vector having such chimeric gene, and a transformant comprising such recombinant vector. The peptide of the invention that is capable of converting a transcription factor into a transcriptional repressor is very short. Thus, it can be very easily synthesized, and it can effectively and selectively repress the transcription of a specific gene. Accordingly, such gene is applicable to and useful in a wide variety of fields, such as repression of the expression of cancerous genes and regulation of the expression of genes encoding pigment-metabolic enzymes.

5 Claims, 30 Drawing Sheets
(6 of 30 Drawing Sheet(s) Filed in Color)

Construction of effector plasmid

Construction of reporter gene

Construction of effector plasmid

Construction of effector plasmid

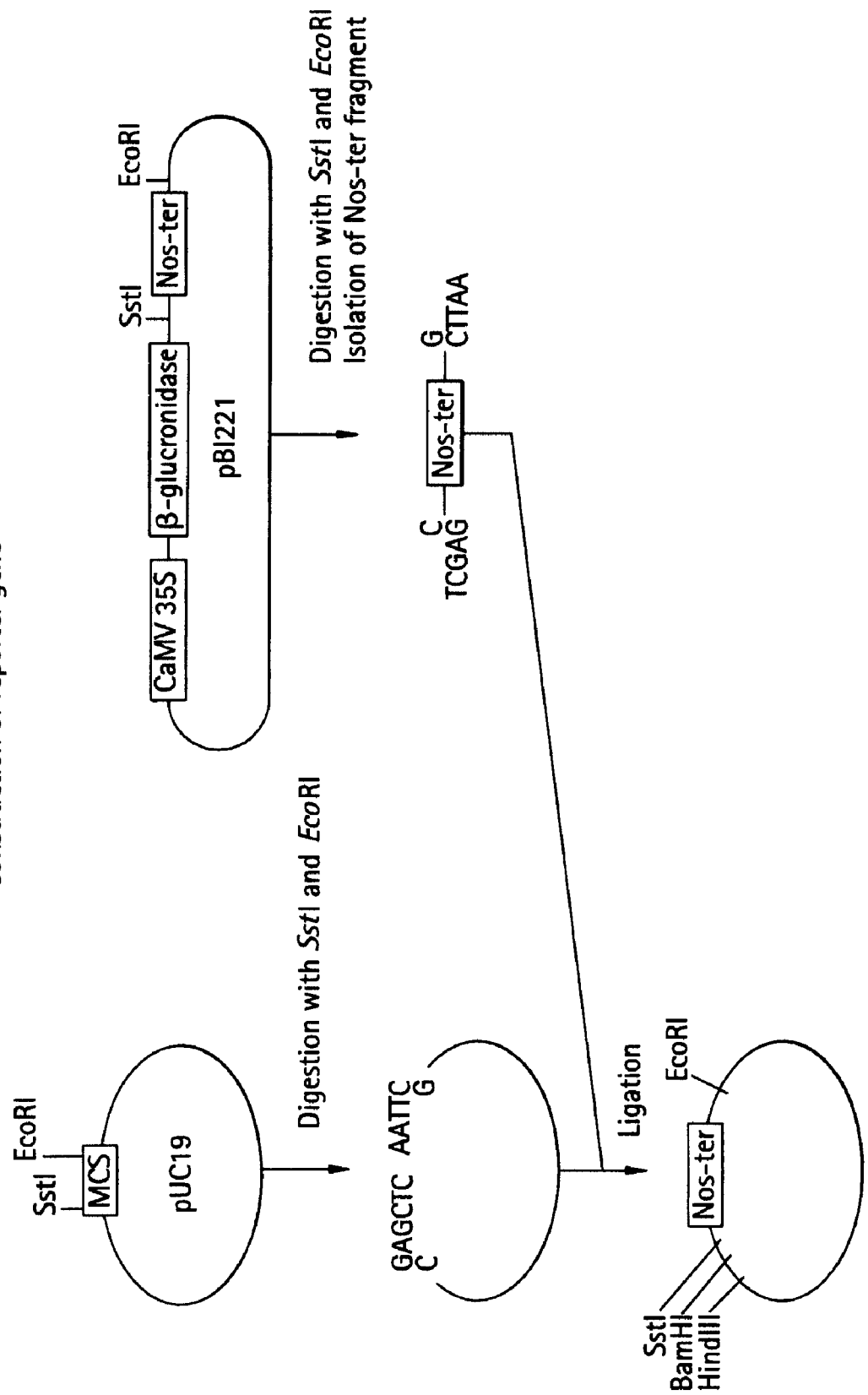

Reporter
    GAL4GCC-LUC    5xGAL4-4xGCC-TATA - [LUC] - Nos

Effector
AtERF5    CaMV35S - Ω - [AtERF5] - Nos
GAL4DB    CaMV35S - Ω - [GAL4DB] - Nos
GAL4DB-SUP    CaMV35S - Ω - [GAL4DB/1/204SUP] - Nos
GAL4DB-175/204SUP    CaMV35S - Ω - [GAL4DB/174/204SUP] - Nos

US 7,342,148 B2

GENE AND PEPTIDE FOR TRANSCRIPTIONAL REPRESSOR

TECHNICAL FIELD

The present invention relates to a peptide or protein capable of converting a transcription factor into a transcriptional repressor, a gene encoding such peptide or protein, a chimeric protein in which the aforementioned peptide or protein is fused to a transcription factor, a chimeric gene in which the gene encoding a peptide or protein is fused to a gene encoding a transcription factor, a recombinant vector having such chimeric gene, and a transformant comprising such recombinant vector.

BACKGROUND ART

In the past, the antisense method and the ribozyme method were known as means of repressing the transcription of organisms' genes to mRNA or repressing the expression of such genes. Research on the application of these techniques to, for example, repression of the expression of genes that can cause diseases, such as oncogenes, or improvement of plants, has made progress. In the antisense method, antisense DNA or RNA that is complementary to a specific site of a target gene, transcription of which is to be repressed, or mRNA to which the target gene has been transcribed, is employed. Existing antisense DNA or RNA, however, cannot be used for repressing the expression of genes other than the aforementioned target gene. Thus, new antisense DNA or RNA needs to be prepared in accordance with sequences of other target genes. In the case of the ribozyme method, the target DNA or mRNA cannot be cleaved with a ribozyme unless such ribozyme is designed to have a complementary sequence in order to bind to the target DNA or mRNA and to be capable of cleaving it at a predetermined position. Even when the ribozyme is designed to cleave the target gene, an excessive sequence is sometimes added to a transcribed ribozyme, which may result in the loss of ribozyme activity when, for example, it is ligated to a promoter such as the cauliflower mosaic virus 35S promoter and a transcription terminator sequence to construct a vector for introduction, and the resultant is actually introduced to a plant cell. In these conventional techniques, identification of the target gene and determination of its nucleotide sequence have always been indispensable. A method for repressing the gene expression via the gene knock-out technique has also been available, although this technique could not be applied to, for example, amphidiploid plants.

The present inventors have found that *Arabidopsis* proteins, namely, AtERF3, AtERF4, AtERF7, and AtERF8 are transcription factors which can significantly repress transcription of genes via an approach completely different from those of the aforementioned conventional techniques. They constructed effector plasmids comprising the genes encoding the aforementioned proteins and DNAs cleaved therefrom, and they introduced the resultants to plant cells. Thus, they actually succeeded in repressing gene transcription (JP Patent Publication (Kokai) Nos. 2001-269177 A, 2001-269178 A, 2001-292776 A, and 2001-292777 A). Further, the present inventors subjected a gene encoding tobacco ethylene responsive element binding factor (ERF) 3, which is a Class II ERF genes (JP Patent Publication (Kokai) No. 2001-269176 A), a gene encoding Oryza sativa Os ERF3 protein (JP Patent Publication (Kokai) No. 2001-269179 A), and genes encoding *Arabidopsis thaliana* ZAT10 and ZAT11, which are Zn finger protein genes, to a test similar to the aforementioned test. As a result, they found that transcription of target gene was repressed. They demonstrated the existence of a conserved motif (L/F)DLN(L/F)(X)P (X denotes any amino acid residue) (SEQ ID NO: 122) in proteins or peptides encoded by these genes, although the nucleotide sequences of these genes are different from each other (The Plant Cell, Vol. 13, 1959-1968, August, 2001).

An object of the present invention is to provide a simple and extensively applicable means for repressing transcription of genes, which eliminates the need for designing new DNA or RNA in each case in accordance with the nucleotide sequence of the target gene, unlike the conventional antisense and ribozyme methods. It is another object of the present invention to provide a peptide for facilitating the repression of transcription of genes and a gene thereof by further advancing the research concerning the transcriptional regulatory protein and identifying the most essential amino acid partial sequence that is actually needed for repressing transcription of genes.

DISCLOSURE OF THE INVENTION

In order to attain the above objects, the present inventors have conducted concentrated studies concerning proteins having the aforementioned conserved motifs. As a result, they have found that a protein that represses the transcription of genes may have a very simple structure, and such short peptide is capable of converting a transcription factor into a transcriptional repressor. The present inventors have also found that the *Arabidopsis* protein, SUPERMAN (hereinafter it may be referred to as "SUP"), has a motif that does not match the aforementioned conserved motifs. However, such protein is capable of converting a transcription factor into a transcriptional repressor, and a chimeric gene in which a gene encoding the SUP protein is fused to a gene encoding a transcription factor can produce proteins having potent capacities for repressing transcription of genes. This has led to the completion of the present invention.

Specifically, the present invention includes the following inventions.

(1) A peptide having the amino acid sequence represented by formula (I) and capable of converting a transcription factor into a transcriptional repressor:

$$\text{X1-Leu-Asp-Leu-X2-Leu-X3} \quad \text{(I) (SEQ ID NO: 123)}$$

wherein X1 denotes 0 to 10 amino acid residues; X2 denotes Asn or Glu; and X3 denotes at least 6 amino acid residues.

(2) A peptide having the amino acid sequence represented by formula (II) and capable of converting a transcription factor into a transcriptional repressor:

$$\text{Y1-Phe-Asp-Leu-Asn-Y2-Y3} \quad \text{(II) (SEQ ID NO: 124)}$$

wherein Y1 denotes 0 to 10 amino acid residues; Y2 denotes Phe or Ile; and Y3 denotes at least 6 amino acid residues.

(3) A peptide having the amino acid sequence represented by formula (III) and capable of converting a transcription factor into a transcriptional repressor:

$$\text{Z1-Asp-Leu-Z2-Leu-Arg-Leu-Z3} \quad \text{(III) (SEQ ID NO: 125)}$$

wherein Z1 denotes Leu, Asp-Leu, or Leu-Asp-Leu; Z2 denotes Glu, Gln, or Asp; and Z3 denotes 0 to 10 amino acid residues.

(4) A peptide having the amino acid sequence represented by Asp-Leu-Z4-Leu-Arg-Leu (wherein Z4 denotes Glu, Gln, or Asp) (SEQ ID NO: 126) and capable of converting a transcription factor into a transcriptional repressor.

(5) A protein having any of the following amino acid sequences (a) to (d) and capable of converting a transcription factor into a transcriptional repressor:

(a) the amino acid sequence as shown in SEQ ID NO: 31, (encoded by SEQ ID NO: 131);

(b) an amino acid sequence derived from the amino acid sequence as shown in SEQ ID NO: 31 by deletion, substitution, or addition of one or a plurality of amino acid residues;

(c) the amino acid sequence as shown in SEQ ID NO: 61; or (d) an amino acid sequence derived from the amino acid sequence as shown in SEQ ID NO: 61 by deletion, substitution, or addition of one or a plurality of amino acid residues.

(6) A gene encoding a peptide having the amino acid sequence represented by formula (I) and capable of converting a transcription factor into a transcriptional repressor:

X1-Leu-Asp-Leu-X2-Leu-X3    (I) (SEQ ID NO: 123)

wherein X1 denotes 0 to 10 amino acid residues; X2 denotes Asn or Glu; and X3 denotes at least 6 amino acid residues.

(7) A gene encoding a peptide having the amino acid sequence represented by formula (II) and capable of converting a transcription factor into a transcriptional repressor:

Y1-Phe-Asp-Leu-Asn-Y2-Y3    (II) (SEQ ID NO: 124)

wherein Y1 denotes 0 to 10 amino acid residues; Y2 denotes Phe or Ile; and Y3 denotes at least 6 amino acid residues.

(8) A gene encoding a peptide having the amino acid sequence represented by formula (III) and capable of converting a transcription factor into a transcriptional repressor:

Z1-Asp-Leu-Z2-Leu-Arg-Leu-Z3    (III) (SEQ ID NO: 125)

wherein Z1 denotes Leu, Asp-Leu, or Leu-Asp-Leu; Z2 denotes Glu, Gln, or Asp; and Z3 denotes 0 to 10 amino acid residues.

(9) A gene encoding a peptide having the amino acid sequence represented by Asp-Leu-Z4-Leu-Arg-Leu (wherein Z4 denotes Glu, Gln, or Asp) (SEQ ID NO: 126) and capable of converting a transcription factor into a transcriptional repressor.

(10) A gene encoding a protein having any of the following amino acid sequences (a) to (d) and capable of converting a transcription factor into a transcriptional repressor:

(a) the amino acid sequence as shown in SEQ ID NO: 31;

(b) an amino acid sequence derived from the amino acid sequence as shown in SEQ ID NO: 31 by deletion, substitution, or addition of one or a plurality of amino acid residues;

(c) the amino acid sequence as shown in SEQ ID NO: 61; or (d) an amino acid sequence derived from the amino acid sequence as shown in SEQ ID NO: 61 by deletion, substitution, or addition of one or a plurality of amino acid residues.

(11) Double-stranded DNA comprising a region encoding any of the above peptides or proteins (1) to (5) and having restriction enzyme sites at its both ends.

(12) A chimeric protein, wherein any of the above peptides or proteins (1) to (5) is fused to a transcription factor.

(13) A chimeric gene, wherein any of the above genes (6) to (10) is fused to a gene encoding a transcription factor.

(14) A recombinant vector comprising the chimeric gene according to (13).

(15) A transformant comprising the recombinant vector according to (14).

(16) A plant comprising the recombinant vector according to (14).

BRIEF DESCRIPTION OF THE DRAWINGS

The application contains at least one drawing executed in color. Copies of this patent or patent application publication with color drawing(s) will be provided by the Office upon request and payment of the necessary fee.

In FIG. 1 to FIG. 4A, 5×GAL4 represents the DNA-binding sequence for the GAL4 transcription factor; TATA represents a region comprising the TATA box of the CaMV 35S promoter; LUC represents a luciferase gene; CaMV 35S represents the 35S protein gene promoter derived from the cauliflower mosaic virus: GAL4DB represents a region encoding the DNA binding domain of yeast GAL4 transcription factor; and Nos represents the transcriptional terminator of the nopaline synthase gene.

FIG. 5 shows a procedure for constructing the effector plasmid pGAL4DB-SUP.

Figure 1A:
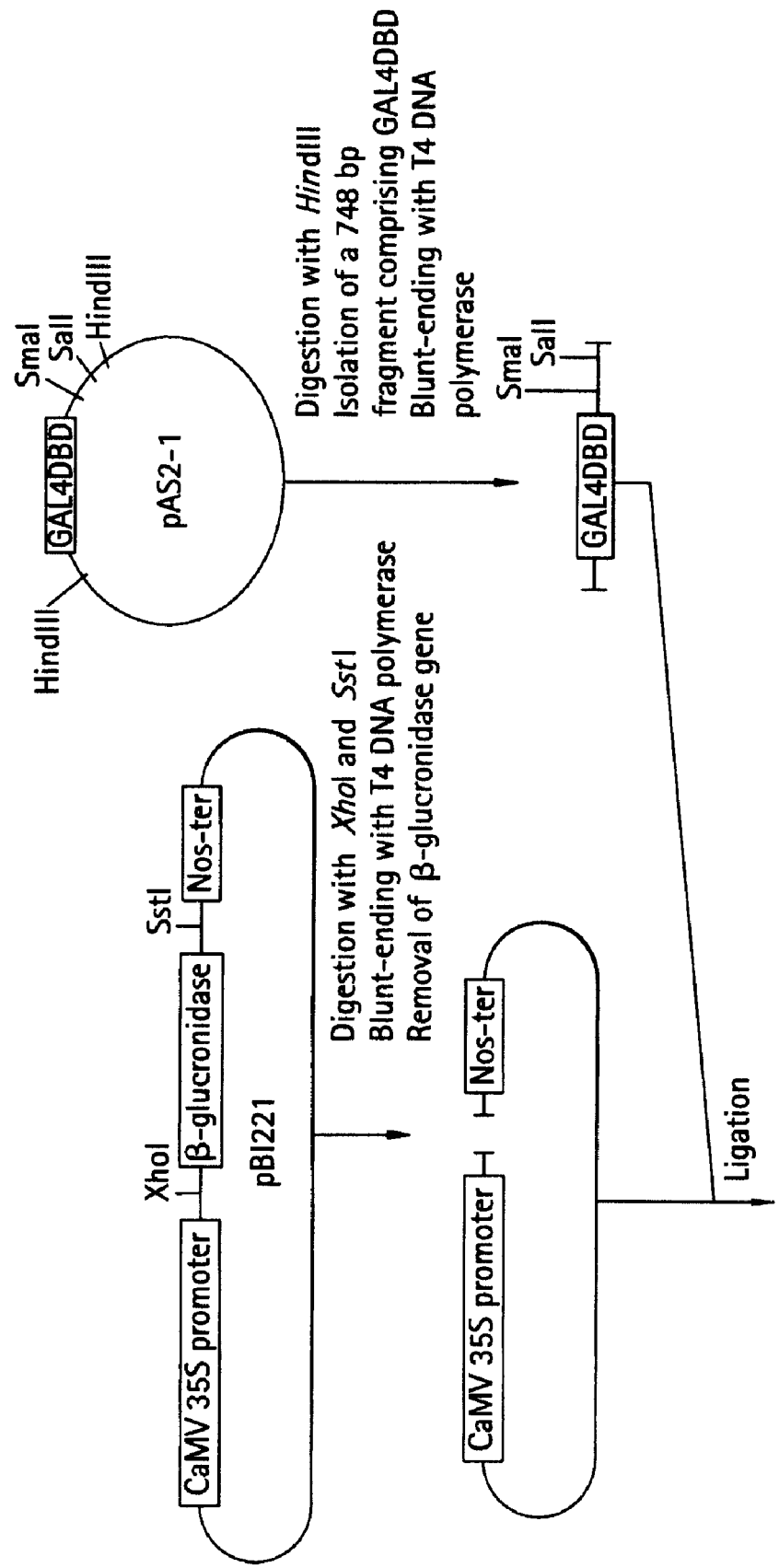
FIG. 1 shows a procedure for constructing an effector plasmid GAL4DB-RD comprising a variety of DNA fragments that are to be tested.

Hereinafter, the present invention is described in greater detail.

The present invention provides a peptide having the amino acid sequence represented by formula (I) and capable of converting a transcription factor into a transcriptional repressor:

X1-Leu-Asp-Leu-X2-Leu-X3      (I) (SEQ ID NO: 123)

wherein X1 denotes 0 to 10 amino acid residues; X2 denotes Asn or Glu; and X3 denotes at least 6 amino acid residues.

In formula (I), X1 may be 0 to 10 amino acid residues, although a shorter sequence is more convenient in terms of the ease of peptide synthesis. Thus, the number of amino acid residues is preferably 10 or less, and more preferably 5 or less.

The number of amino acid residues denoted by X3 is essential, and a minimum of 6 amino acid residues was unexpectedly found to be sufficient for exhibiting the aforementioned functions. Further, X1 and X3 may be amino acids of any type. For example, P (proline) in the aforementioned conserved motif (L/F)DLN(L/F)(X)P (SEQ ID NO: 122) of peptides described in the Background Art section is not necessary for X3. X3 may be simply comprised of aligned alanines.

In contrast, a sequence consisting of LDLNL (Leu-Asp-Leu-Asn-Leu) (SEQ ID NO: 13) or LDLN (Leu-Asp-Leu-Asn) (SEQ ID NO: 10) does not exhibit the aforementioned functions. A sequence that was designed to have 5 or 6 amino acid residues denoted by X2 very significantly exhibits the aforementioned functions whereas the one designed to have 3 amino acid residues does not exhibit such functions.

The present invention also provides a peptide having the amino acid sequence represented by formula (II) and capable of converting a transcription factor into a transcriptional repressor:

Y1-Phe-Asp-Leu-Asn-Y2-Y3      (II) (SEQ ID NO: 124)

wherein Y1 denotes 0 to 10 amino acid residues; Y2 denotes Phe or Ile; and Y3 denotes at least 6 amino acid residues.

In formula (II), Y1 may be 0 to 10 amino acid residues, although a shorter sequence is more convenient in terms of the ease of peptide synthesis. Thus, the number of amino acid residues is preferably 10 or less, and more preferably 5 or less.

A minimum of 6 amino acid residues denoted by Y3 were found to be sufficient for exhibiting the aforementioned functions. Further, Y1 and Y3 may be any amino acids.

The present invention also provides a peptide having the amino acid sequence represented by formula (III) and capable of converting a transcription factor into a transcriptional repressor:

Z1-Asp-Leu-Z2-Leu-Arg-Leu-Z3      (III) (SEQ ID NO: 125)

wherein Z1 denotes Leu, Asp-Leu, or Leu-Asp-Leu; Z2 denotes Glu, Gln, or Asp; and Z3 denotes 0 to 10 amino acid residues.

In formula (III), Z3 may be 0 to 10 amino acid residues, although a shorter sequence is more convenient in terms of the ease of peptide synthesis. Thus, the number of amino acid residues is preferably 10 or less, and more preferably 5 or less. Specific examples of Z3 include, but are not limited to, G, GFF, GFA, GYY, and AAA. A peptide represented by formula (III) has a motif DLELRL (SEQ ID NO: 83) that is different from a conserved motif (L/F)DLN(L/F)(X)P (SEQ ID NO: 122) of peptides as described in the Background Art section. This motif corresponds to the amino acid sequence (the 196/201 region) of the SUP protein (Asp-Leu-Glu-Leu-Arg-Leu) (SEQ ID NO: 83). The total number of peptides is preferably 20 amino acids at a maximum in terms of the ease of peptide synthesis. Examples of preferable peptides include the following.

```
Leu-Asp-Leu-Glu-Leu-Arg-Leu,        (SEQ ID NO: 89)

Leu-Asp-Leu-Glu-Leu-Arg-Leu-Gly,    (SEQ ID NO: 101)

Leu-Asp-Leu-Glu-Leu-Arg-Leu-Ala-    (SEQ ID NO: 95)
Ala-Ala

Leu-Asp-Leu-Glu-Leu-Arg-Leu-Gly-    (SEQ ID NO: 16)
Phe-Ala

Asp-Leu-Asp-Leu-Glu-Leu-Arg-Leu-    (SEQ ID NO: 119)
Gly-Phe-Ala
```

-continued

Leu-Asp-Leu-Asp-Leu-Glu-Leu-Arg-        (SEQ ID NO: 120)
Leu-Gly-Phe-Ala

The peptide in the present invention that is capable of converting the transcription factor into a transcriptional repressor may comprise the minimum sequence Asp-Leu-Glu-Leu-Arg-Leu (SEQ ID NO: 83).

In the above peptide, glutamic acid (E) in the minimum sequence may be substituted with glutamine (Q) or aspartic acid (D). Peptides, such as Leu-Asp-Leu-Gln-Leu-Arg-Leu-Gly-Tyr-Tyr (SEQ ID NO: 86) or Asp-Leu-Asp-Leu-Arg-Leu (SEQ ID NO: 116), have excellent effects of repressing transcriptional activities. In contrast, the sequence Leu-Glu-Leu-Arg-Leu (SEQ ID NO: 104) does not have a function of transcriptional repression.

Accordingly, only 5 or 6 amino acid residues are required in the peptides represented by formulae (I) to (III) in order to convert a transcription factor into a transcriptional repressor.

The present invention provides a protein having any of the following amino acid sequences (a) to (d) and capable of converting a transcription factor into a transcriptional repressor:

(a) the amino acid sequence as shown in SEQ ID NO: 31;

(b) an amino acid sequence derived from the amino acid sequence as shown in SEQ ID NO: 31 by deletion, substitution, or addition of one or a plurality of amino acid residues;

(c) the amino acid sequence as shown in SEQ ID NO: 61; or (d) an amino acid sequence derived from the amino acid sequence as shown in SEQ ID NO: 61 by deletion, substitution, or addition of one or a plurality of amino acid residues.

The range of "one or a plurality of" in "an amino acid sequence derived from the amino acid sequence as shown in SEQ ID NO: 31 (or SEQ ID NO: 61) by deletion, substitution, or addition of one or a plurality of amino acid residues" is not particularly limited. For example, the number of amino acids is approximately 1 to 20, preferably 1 to 10, more preferably 1 to 7, still more preferably 1 to 5, and particularly preferably 1 to 3.

The aforementioned deletion, substitution, or addition of amino acid residues can be implemented by modifying a gene encoding the aforementioned protein in accordance with a technique conventional in the art. Mutation can be introduced to a gene by conventional techniques such as the Kunkel method or the gapped duplex method or techniques in accordance therewith. Mutation can be introduced by, for example, using a kit for introducing mutation utilizing site-specific mutagenesis (e.g., Mutant-K (Takara) or Mutant-G (Takara)) or the LA PCR in vitro Mutagenesis Series kit (Takara).

The SUP protein having the amino acid sequence as shown in SEQ ID NO: 31 and SUP gene are already known. The amino acid sequence (residues 195 to 199, corresponding to the nucleotide sequence (the 583/597 region)) are leucine (L)-aspartic acid (D)-leucine (L)-glutamic acid (E)-leucine (L) (SEQ ID NO: 127), and a proline residue is not present downstream of this sequence toward the 3'-terminus. Instead, an amino acid sequence that is different from the motif (L/F)DLN(L/F)(X)P (SEQ ID NO: 122) as mentioned in the Background Art section is present in the aforementioned sequence.

In the present invention, a protein used for converting a transcription factor into a transcriptional repressor is not limited to the one having the full-length of the amino acid sequence as shown in SEQ ID NO: 31. The protein may be a protein or peptide comprising a partial sequence of the aforementioned amino acid sequence.

An example of a protein having such partial sequence has the amino acid sequence as shown in SEQ ID NO: 61 (the 175/204 region of the SUP protein). An example of a peptide having a partial sequence is represented by formula (III).

The present invention provides a gene encoding any of the aforementioned peptides or proteins.

The present invention also provides a chimeric protein in which any of the aforementioned peptides or proteins is fused to a transcription factor and a chimeric gene in which the gene encoding any of the aforementioned peptides or proteins is fused to a gene encoding a transcription factor. In a transformant prepared by using a recombinant vector comprising the aforementioned chimeric gene, a chimeric protein corresponding to the aforementioned chimeric gene is produced. The DNA-binding region derived from a transcription factor in this chimeric protein binds to a target gene. In this case, however, functions of a transcription factor are converted to those for repressing transcription, and transcription of the target gene is repressed. Accordingly, the target gene is not expressed.

The chimeric protein of the present invention is capable of repressing transcription of genes regardless of the type of gene. The chimeric protein of the present invention is required to bind to the target gene in order to repress its transcription. Accordingly, the gene encoding a peptide or protein (hereinafter, it may be referred to as "the gene of the present invention") is allowed to fuse with a gene encoding a DNA-binding domain of a transcription factor that binds to a specific target gene to prepare a chimeric gene, and transcription of specific target genes can be selectively repressed.

Specifically, the chimeric gene of the present invention expresses a chimeric protein in which a peptide or protein capable of converting a transcription factor into a transcriptional repressor is fused to transcription factor. The aforementioned chimeric gene specifically represses the transcription of genes to which a DNA-binding domain derived from a transcription factor of the chimeric protein binds. When transcription of a given gene is intended to be repressed, therefore, transcription of such gene may be repressed by selecting a transcription factor that plays a key role in transcription of the aforementioned gene, ligating the gene of the present invention to the terminus or a DNA-binding domain of a gene encoding the aforementioned transcription factor to construct a chimeric gene, ligating the resulting gene to an adequate vector, and introducing the resultant into a site of an organism of interest.

A chimeric protein resulting from the chimeric gene of the present invention specifically represses the transcription of a gene to which a DNA-binding domain of the transcription factor binds. Such repression appears as a dominant trait. That is, such chimeric protein can repress functions of other transcription factors that are also involved in this gene transcription.

This is described more specifically with reference to a case where the cup-shaped cotyledon 1 (CUC1) transcription factor is used (Plant Cell, 9, 841, 1997).

Figure 14:
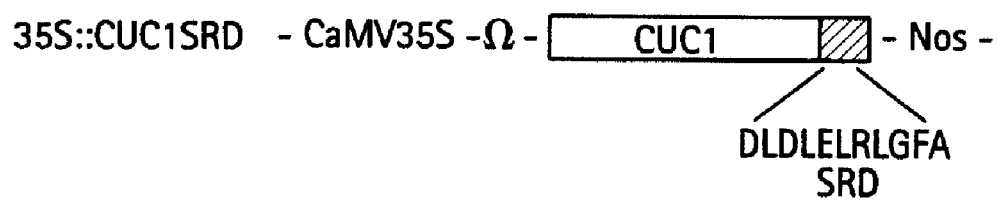
FIG. 14 schematically shows the structure of the plasmid p35S::CUC1SRD for transforming *Arabidopsis thaliana* SRD is SEQ ID NO: 16. (SEQ ID NO: 119).
Figure 15:
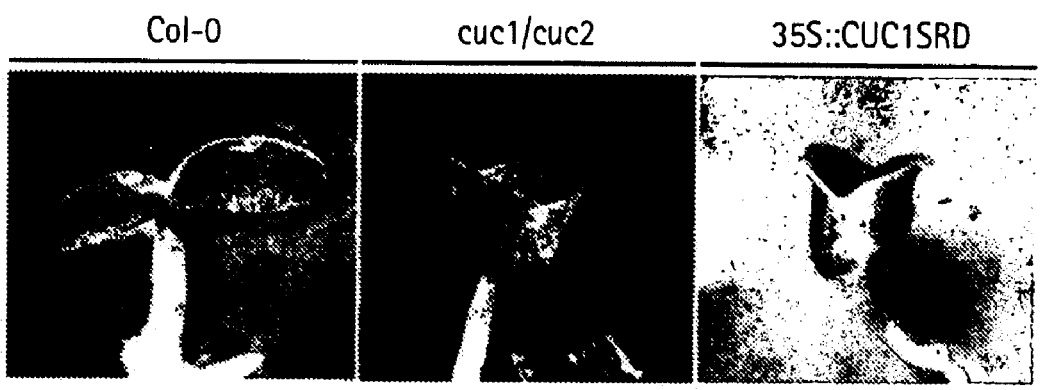
FIG. 15 is a photograph showing 5- to 10-days old cotyledons of a wild-type (Col-0), cuc1/cuc2 double mutant (cuc1/cuc2), and a plant transformed with p35S::CUC1SRD (35S::CUC1SRD).

CUC1 is a transcription factor that regulates apical bud formation of seedlings together with CUC2 having the same NAC domain. Only when mutation is present in both CUC1 and CUC2 genes, the cotyledon of the plant forms a cup-like shape (a cup-shaped cotyledon), and the apical meristem is not formed. In contrast, a plant having mutation in only either CUC1 or CUC2 is normal. Accordingly, CUC1 and CUC2 are known to be functionally redundant factors (Development, 126, 1563, 1999; Development, 128, 1127, 2000). When a chimeric gene, in which a gene encoding the peptide of the present invention is bound to either one of the functionally redundant CUC1 or CUC2 transcription factor genes, for example, the CUC1 gene, is allowed to express in a plant, the expressed chimeric protein can suppress transcription activity of the functionally redundant CUC2 transcription factor as well as that of the CUC1 transcription factor. That is, it can repress the expression of genes regulated by the CUC1 transcription factor. In such a case, the cotyledon of the plant forms a cup-like shape, which is a trait of a cuc1/cuc2 double mutant (a cup-shaped cotyledon), and the apical meristem is not formed. In the Example 5 below, a chimeric gene was constructed, wherein the gene encoding the DLDLELRLGFA peptide (SEQ ID NO: 119) of the present invention (this peptide is referred to as "SRD") had been allowed to fuse with the CUC1 gene (FIG. 14), and *Arabidopsis thaliana* was transformed with the chimeric gene. This demonstrates that the transgenic plant takes on a cup-like shape indicating a phenotype of a cuc1/cuc2 double mutant (a cup-shaped cotyledon) (FIG. 15, right). Formation of the apical meristem is not observed as with the case of the deficiencies of STM gene which regulates the formation of the apical meristem regulated by the CUC1 transcription factor. This indicates that the CUC1 transcription factor capable of activating transcription was functionally converted to a transcriptional repressor via fusion with the DLDLELRLGFA peptide (SEQ ID NO: 119) of the present invention. The aforementioned further indicates that the above peptide suppresses not only activity of CUC1 transcription factor, but also preferentially suppresses activity of the CUC2 transcription factor which is functionally redundant with CUC1, and represses expression of genes located downstream.

As shown from the foregoing, the peptide of the present invention and a gene encoding the peptide are capable of converting any transcription factor into a transcriptional repressor and are also capable of suppressing activity of other transcription factors that are functionally redundant.

In many cases, a plant has a plurality of functionally redundant transcription factors as demonstrated with reference to CUC. The transcriptional repressor, functions of which had been converted by the present invention, appears as a dominant trait. The present invention is, therefore, very useful since functions of transcription factors that were not elucidated by conventional single-gene knockout technology can be analyzed, and it can be effectively applied to plants having amphidiploid genomes such as wheat.

As mentioned above, the chimeric gene of the present invention produces a chimeric protein corresponding thereto, and this chimeric protein is allowed to bind to the target gene. Thus, transcription of the target gene is repressed. Accordingly, this chimeric protein is separately synthesized and the resultant may be directly introduced into a site in an organism where the target genes are expressed.

This chimeric protein may be synthesized by a conventional technique of genetic engineering. For example, the chimeric gene may be incorporated into an adequate vector, microorganisms may be transformed using the same, and the transgenic microorganisms may be cultured. Thus, a large amount of the chimeric proteins can be synthesized.

The site where the gene of the present invention is fused to a transcription factor is located downstream of the region encoding the DNA-binding domain in the transcription factor. When the gene of the present invention is intended to be inserted in a gene encoding a transcription factor, this insertion involves laborious operations such as cleavage of the gene encoding a transcription factor or ligation and recombination of the gene of the present invention. Accordingly, it is convenient to simply bind the gene of the present invention to the terminus located downstream of the region encoding the transcription factor protein. This is one of the advantages of the present invention.

The gene of the present invention may have any nucleotide sequence as long as it encodes a peptide having any of the amino acid sequences represented by formulae (I) to (III) or a protein having the amino acid sequence as shown in SEQ ID NO: 31 or 61. The gene of the present invention may have a site where it is fused to the gene encoding a transcription factor. When the amino acid reading frame of the gene of the present invention is not in-frame with the reading frame of the gene encoding the transcription factor, the gene should be designed to have a reading frame to be in-frame with that of interest. Thus, the gene may have additional nucleotide sequences.

In the present invention, gene transcription may be repressed by directly introducing the aforementioned chimeric protein in an organism. When breed improvement in plant is intended, for example, transcription of a specific gene must be constantly repressed to repress expression thereof. Accordingly, it is more effective to ligate a gene encoding the aforementioned chimeric protein to an adequate vector and transform plants and the like using the resulting recombinant vector. This enables a gene encoding a chimeric protein to be constantly expressed in a plant, and the resulting chimeric protein continuously represses transcription of genes.

This mechanism of repressing transcription is described in greater detail with reference to a case where the *Arabidopsis thaliana* ethylene-insensitive 3 gene (hereafter referred to as the "EIN3 gene") is used as a transcription factor. The sequence of this EIN3 gene and that of a protein produced there from are shown in SEQ ID NOS 52 and 132, respectively.

The EIN3 protein factor, which is the EIN3 gene product, serves as a transcription factor and is a factor in ethylene signal transduction mediating biological activities induced by phytohormone ethylene, such as morphological changes of the etiolated seedling (the triple response), inhibition of elongation, and expression of an ethylene responsive gene.

A gene fragment encoding the peptide or protein according to the present invention is fused to a region encoding the DNA-binding domain of the EIN3 gene to prepare a chimeric gene. The resultant is ligated to, for example, a vector for plant transformation having the cauliflower mosaic virus 35S promoter, and *Arabidopsis thaliana* is transformed using this recombinant vector. Wild-type *Arabidopsis thaliana* exhibits morphological changes in the etiolated seedling (the triple response) and inhibition of elongation in the presence of ethylene or its precursor 1-aminocyclopropane-D-carboxylic acid. In the case of transgenic *Arabidopsis thaliana*, however, ethylene-responsive biological activities thereof are significantly suppressed. Accordingly, the gene of the present invention is capable of converting the function of EIN3 for activating transcription to that for repressing transcription.

In the present invention, examples of a transcription factor that is converted into a transcriptional repressor and a gene thereof include, but are not limited to, the aforementioned EIN3 and a gene thereof, yeast GAL4, ERF4, CBF1, ERF2, EREB1, CUC1, and CUC2 proteins and genes thereof. Transcription factors of animals, plants, and microorganisms and genes thereof can be extensively employed.

BEST MODES FOR CARRYING OUT THE INVENTION

The present invention is hereafter described with reference to the following examples, although the technical scope of the present invention is not limited thereto.

In Example 1, (i) an effector plasmid in which a variety of synthesized gene fragments fused to the encoding region of the DNA-binding domain of the yeast GAL4 transcription factor was ligated to the downstream region of the cauliflower mosaic virus 35S promoter, which functions in plant cells, and (ii) a reporter gene comprising the luciferase gene in which the enhancer region of the cauliflower mosaic virus 35S promoter, the GAL4 protein-binding DNA sequence, and the TATA region of the cauliflower mosaic virus 35S promoter are ligated to the promoter region were constructed. These effector plasmid and reporter gene were co-introduced into Arabidopsis thaliana leaves using a particle gun, and activity of the luciferase gene, i.e., the reporter gene, was assayed to investigate the repression activity of transcription of the synthesized gene fragments.

In Example 2, the transcriptional repression activity of the gene encoding a protein having the full-length SUP amino acid sequence and the gene encoding the partial amino acid sequence (the 175/204 region) of the SUP protein was investigated based on the assay of luciferase activity of the reporter gene.

In Example 3, the activity of the gene encoding the partial SUP protein having the amino acid sequence (the 175/204 region) of SUP for repressing transcriptional function of EIN3 was investigated in plants.

In Example 4, the activity of the gene encoding the partial ERF3 protein having the amino acid sequence (the 191/225 region) of ERF3 for repressing transcriptional function of EIN3 was investigated in plants.

In Example 5, a gene fragment encoding DLDLELRLGFA (SEQ ID NO: 119) (SUPERMAN repression domain (SRD), residues 194-204) was fused to a transcription factor CUC1, and the resultant was ligated to the downstream region of the cauliflower mosaic virus 35S promoter to construct a plasmid for transformation, Arabidopsis thaliana was transformed using the aforementioned plasmid, and morphological changes of the cotyledon after germination were observed. Thus, effects of the aforementioned gene fragment in repressing the expression of the genes for CUC1, and for CUC2 that is functionally redundant with CU1, were investigated In Example 6, a gene encoding LDLELRLGFA (SEQ ID NO: 16) (SUPERMAN repression domain (SRD1), residues 195-204) and LDLNLAPPMEF (SEQ ID NO: 4) (ERF3 repression domain (RD1), residues 215-225) was fused to a plant transcription factor EIN3, Arabidopsis thaliana was transformed in the same manner, and morphological changes of relevant plants in the presence of ethylene were observed. Thus, effects of the aforementioned gene fragment in repressing transcription of the target gene for EIN3 were inspected.

In Example 7, a chimeric repressor (35S::PAP1SRDX) prepared by applying a peptide (SRDX) consisting of 12 amino acid residues represented by the amino acid sequence LDLDLELRLGFA (SEQ ID NO: 120) to the carboxyl terminus of the production-of-anthocyanin-pigment 1 transcription factor (PAP1) (Borevitz J. O., Xia Y., Blount J., Dixon R. A. & Lamb C., Activation tagging identifies a conserved MYB regulator of phenylpropanoid biosynthesis, Plant Cell 12, 2383, 2000)) was introduced into Arabidopsis thaliana to produce the transgenic plants. The effects of repressing the transcription of an anthocyanin-synthesizing gene in the plants were inspected.

In Example 8, a chimeric repressor (35S:: AtMYB23SRDX) prepared by applying a peptide (SRDX) consisting of 12 amino acid residues represented by the amino acid sequence LDLDLELRLGFA (SEQ ID NO: 120) to the carboxyl terminus of the AtMYB23 transcription factor (Kink V., Schnittger A., Radchuk V., Adler K., Hulskamp M., & Baumlein H., Ectopic expression of the Arabidopsis AtMYB23 gene induces differentiation of trichome cells, Dev Biol. 235, 366 (2001); a conserved MYB regulator of phenylpropanoid biosynthesis, Plant Cell 12, 2383 (2000)) was introduced to Arabidopsis thaliana to produce the transgenic plants. The effects of repressing the transcription of genes that regulate trichome generation were inspected.

In Example 9, a repression activity of transcription was tested using tobacco leaf and petunia.

EXAMPLE 1

Figure 1B:
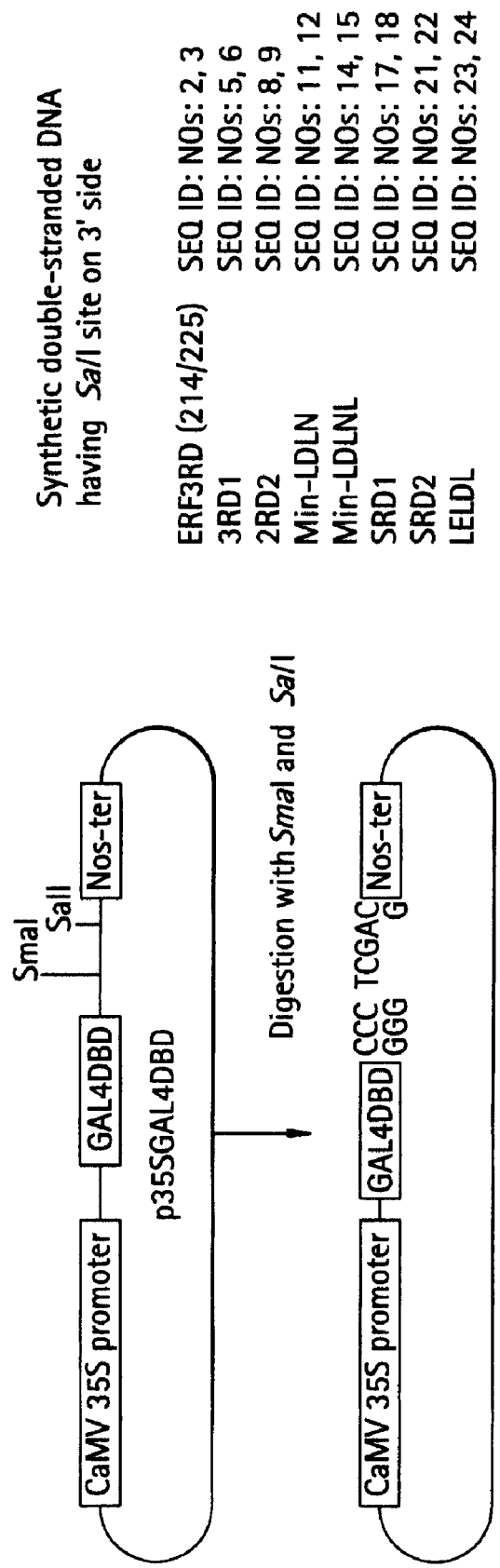
Figure 1C:
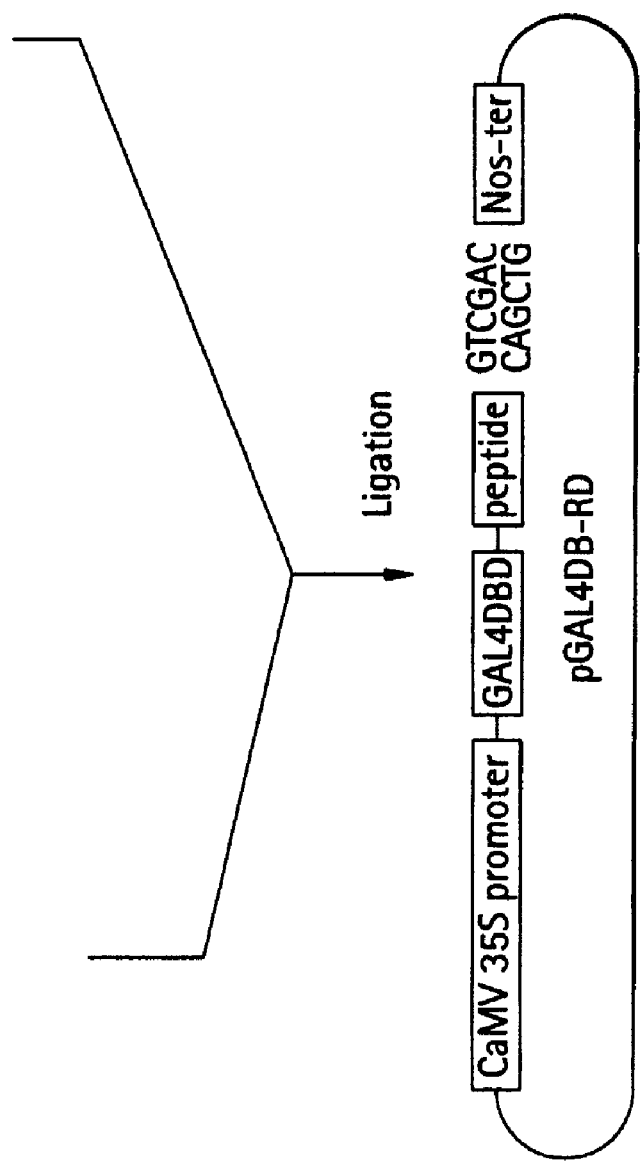
Figure 2A:
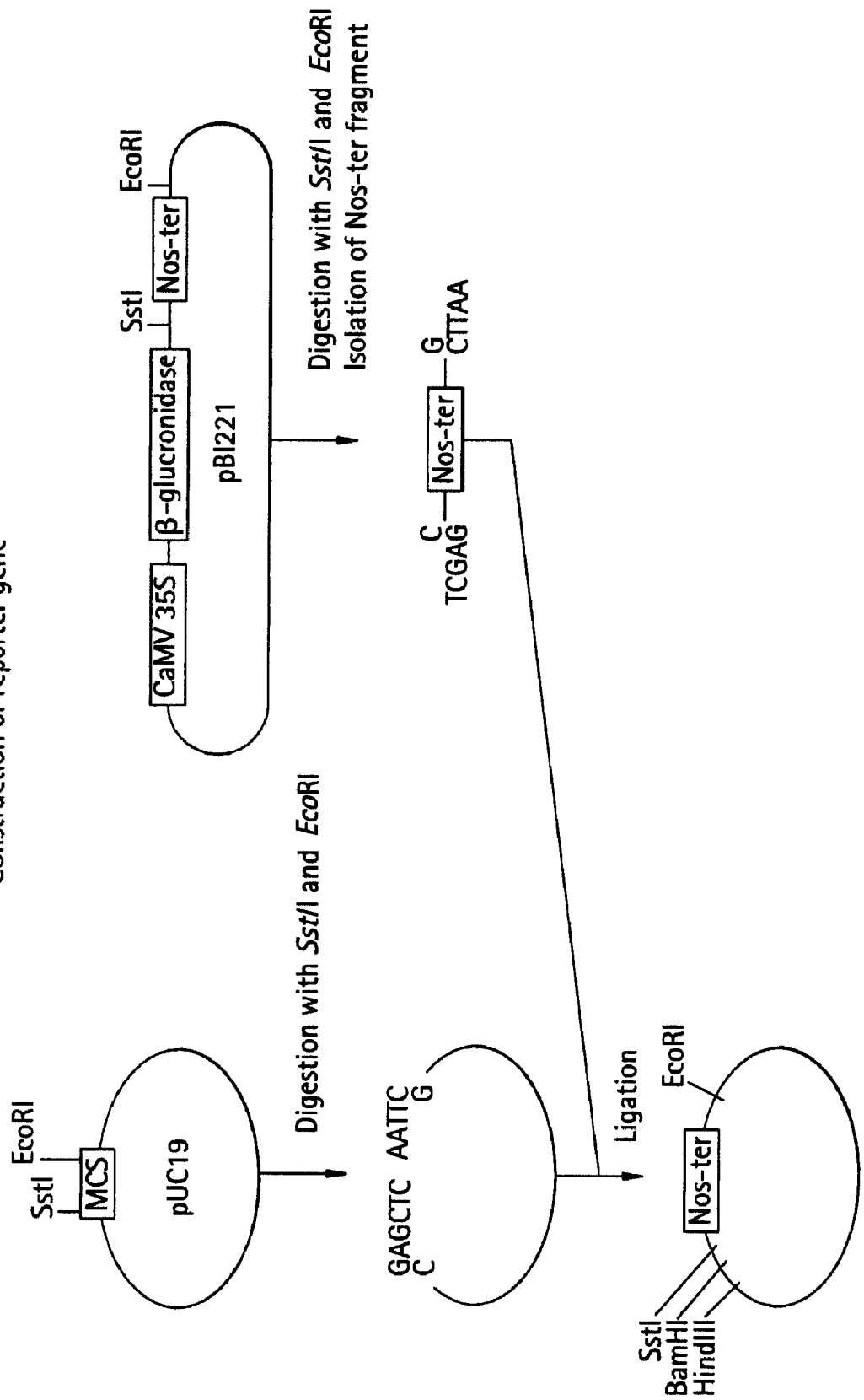
FIG. 2 shows the first half of the procedure for constructing a reporter gene p35S-GAL4-LUC.
Figure 2B:
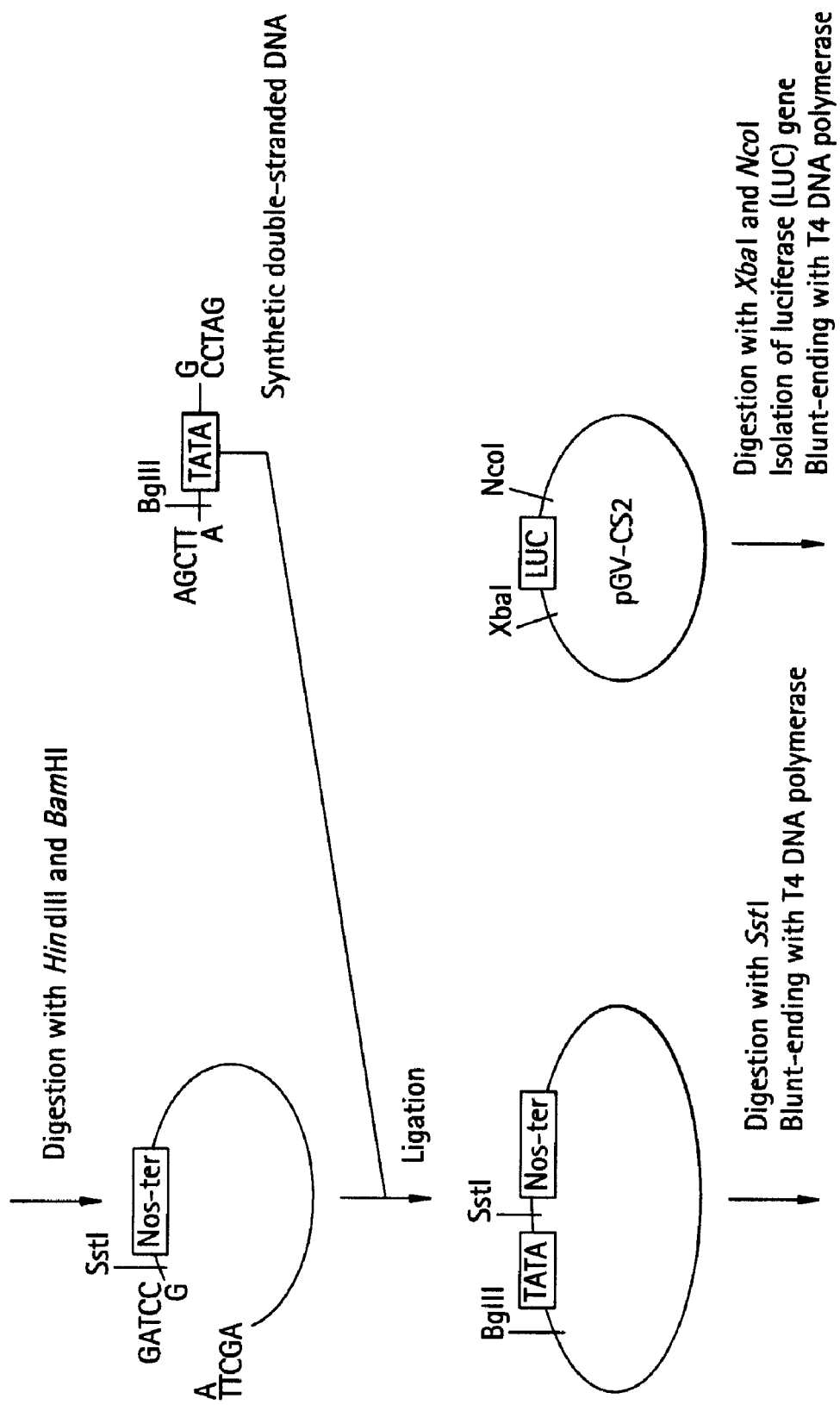
Figure 2C:
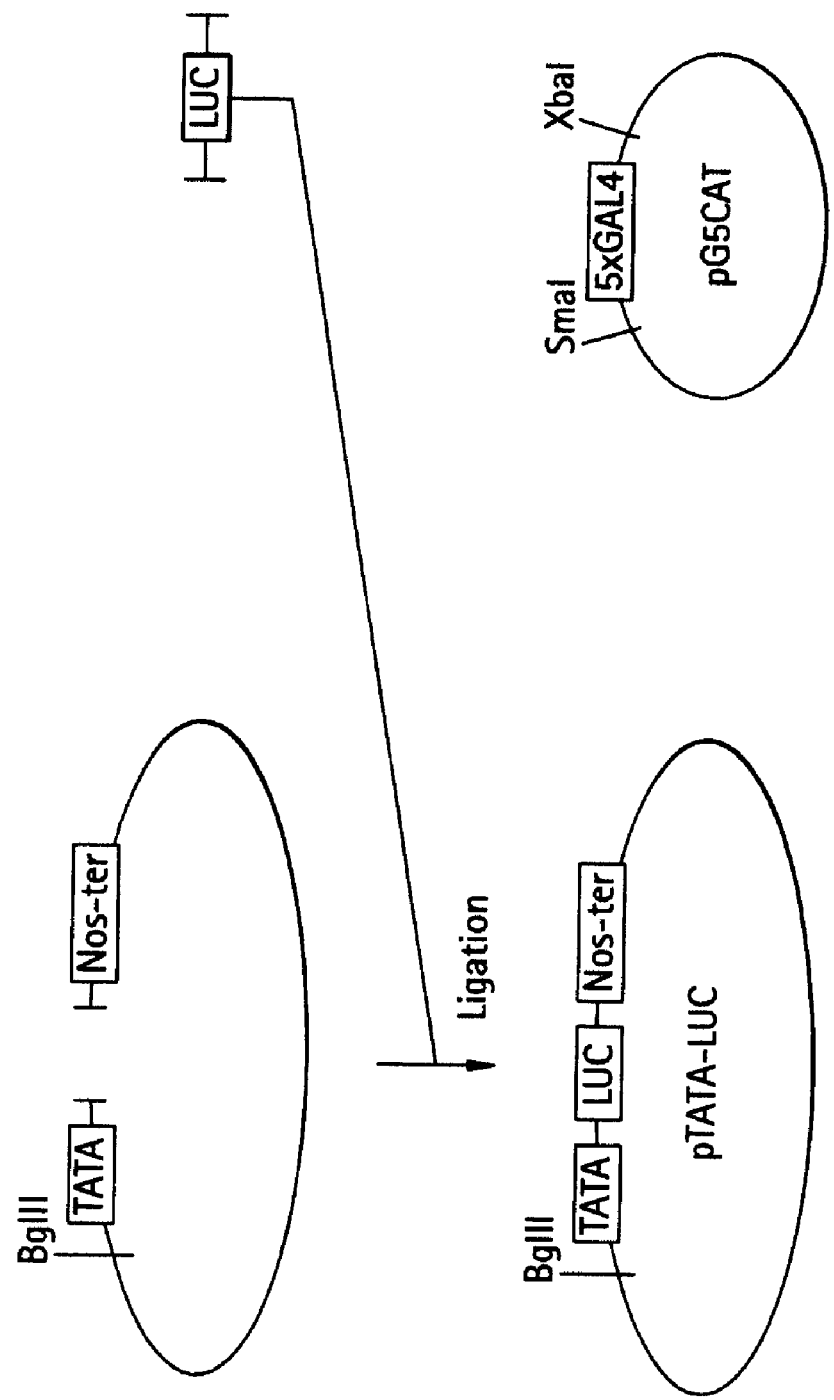
Figure 2D:
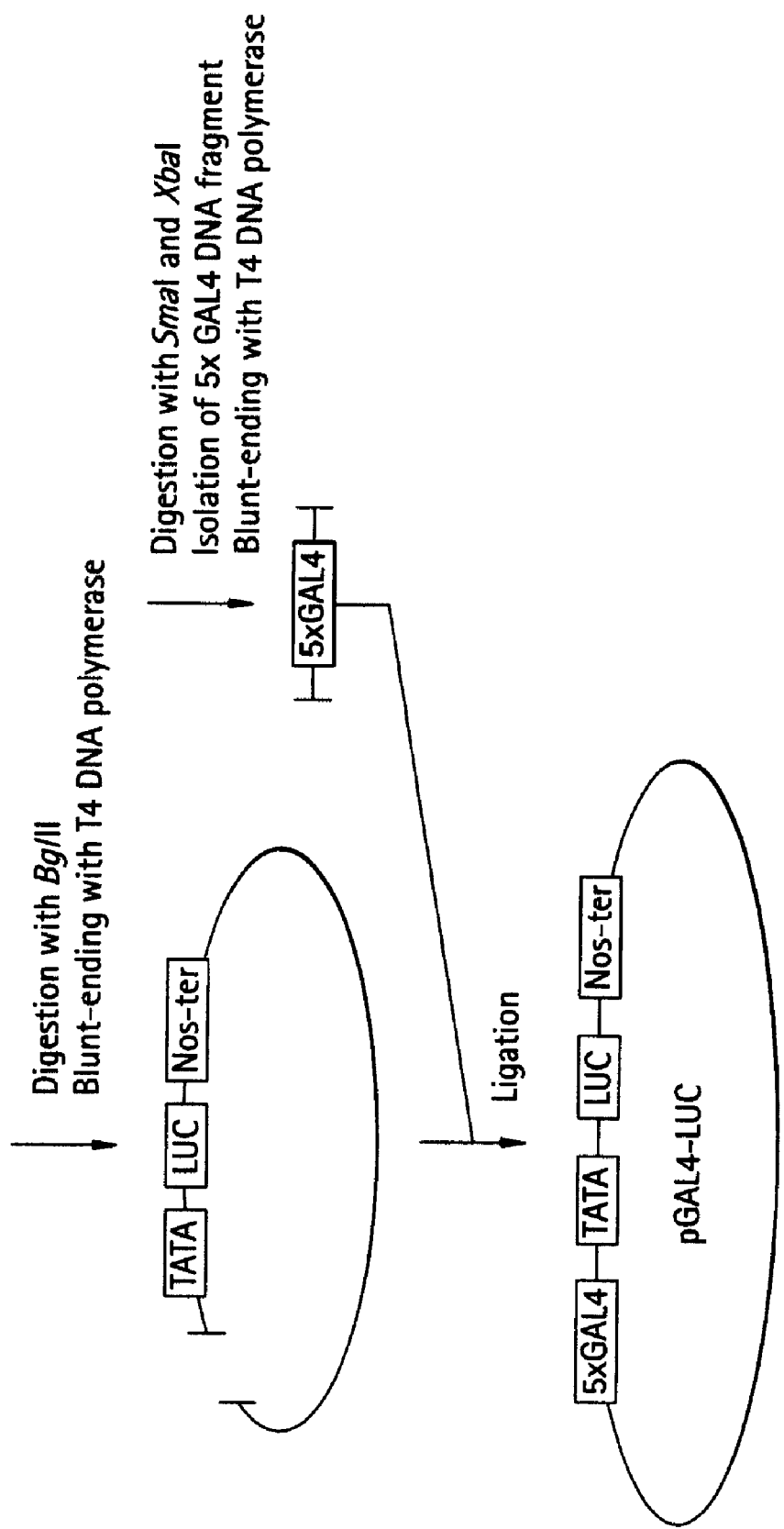

Identification of Peptide that Serves as a Repression Domain (1) Construction of Effector Plasmid pGAL4DB-RD (FIG. 1)

Plasmid pBI221 (Clontech, U.S.A.) was cleaved with restriction enzymes XhoI and SacI and blunt-ended with T4 polymerase. Thereafter, the GUS gene was removed by agarose gel electrophoresis to obtain a fragment of 35S-Nos plasmid DNA comprising the cauliflower mosaic virus 35S promoter (hereafter referred to as "CaMV 35S") and a transcription terminator of the nopaline synthase gene (Nos terminator, hereafter referred to as "Nos-ter").

The pAS2-1 vector (Clontech) was digested with a restriction enzyme HindIII, a 748 bp DNA fragment encoding a DNA-binding domain of the yeast GAL4 protein (hereafter this fragment (the 1/147 region) is referred to as "GAL4DBD") was isolated by agarose gel electrophoresis, and the isolated fragment was blunt-ended with T4 DNA polymerase. This DNA fragment comprising the GAL4DBD-encoding region was inserted in the blunt-ended site between the 35S promoter and the Nos terminator of the aforementioned 35S-Nos DNA fragment, and a clone in which the ORFs of the DNA-binding domain of the yeast GAL4 protein are oriented in the forward direction relative to the 35S promoter was selected to construct a p35S-GAL4DBD vector.

Two DNA strands encoding a peptide to be tested, which had been designed to have a reading frame to be in-fame with the amino acid reading frame of GAL4DBD, were synthesized. The nucleotide sequences of the synthesized DNA and the amino acid sequences encoded thereby are shown below.

```
ERF3RD (214/225)
Amino acid sequence: DLDLNLAPPMEF        (SEQ ID NO: 1)

5'-CGATCTTGATCTTAACCTTGCTCCACCTATG        (SEQ ID NO: 2)
GAATTTTGAG-3'

5'-TCGACTCAAAATTCCATAGGTGGAGCAAGGT        (SEQ ID NO: 3)
TAAGATCAAGATCG-3'

3 RD1
Amino acid sequence: LDLNLAPPMEF         (SEQ ID NO: 4)

5'-CCTTGATCTTAACCTTGCTCCACCTATGGAA        (SEQ ID NO: 5)
TTTTGAG-3'

5'-TCGACTCAAAATTCCATAGGTGGAGCAAGGT        (SEQ ID NO: 6)
TAAGATCAAGG-3'

3 RD2
Amino acid sequence: LDLNLAAAAAA         (SEQ ID NO: 7)

5'-CCTTGATCTTAACCTTGCTGCTGCTGCTGCT        (SEQ ID NO: 8)
```

-continued
```
GCTTGAG-3'

5'-TCGACTCAAGCAGCAGCAGCAGCAGCAAGGT      (SEQ ID NO: 9)
TAAGATCAAGG-3'

Min-LDLN
Amino acid sequence: LDLN              (SEQ ID NO: 10)

5'-CCTGGATCTAAATTAAG-3'                 (SEQ ID NO: 11)

5'-TCGACTTAATTTAGATCCAGG-3'             (SEQ ID NO: 12)

Min-LDLNL
Amino acid sequence: LDLNL             (SEQ ID NO: 13)

5'-CCTGGATCTAAATCTGTAAG-3'              (SEQ ID NO: 14)

5'-TCGACTTACAGATTTAGATCCAGG-3'          (SEQ ID NO: 15)

SRD1
Amino acid sequence: LDLELRLGFA        (SEQ ID NO: 16)

5'-CCTGGATCTAGAACTCCGTTTGGGTTTCGCT      (SEQ ID NO: 17)
TAAG-3'

5'-TCGACTTAAGCGAAACCCAAACGGAGTTCTA      (SEQ ID NO: 18)
GATCCAGG-3'

SRD2
Amino acid sequence: LDLELGFA          (SEQ ID NO: 19)

5'-CCTGGATCTAGAACTCGGTTTCGCTTAA         (SEQ ID NO: 20)
G-3'

5'-TCGACTTAAGCGAAACCGAGTTCTAGATCC       (SEQ ID NO: 21)
AGG-3'

LELDL
Amino acid sequence: LELDLAAAAAA       (SEQ ID NO: 22)

5'-ACTGGAACTAGATCTAGCTGCAGCTGCAGCT      (SEQ ID NO: 23)
GCTTAAG-3'

5'-TCGACTTAAGCAGCTGCAGCTGCAGCTAGAT      (SEQ ID NO: 24)
CTAGTTCCAGT-3'

Amino acid sequence: LELRLAAAAAA       (SEQ ID NO: 80)

5'-ACTAGAACTCCGTTTGGCTGCCGCAGCGGCT      (SEQ ID NO: 81)
GCATAATGAG-3'

5'-TCGACTCATTATGCAGCCGCTGCGGCAGCCA      (SEQ ID NO: 82)
AACGGAGTTCTAGT-3'

Amino acid sequence: DLELRL            (SEQ ID NO: 83)

5'-AGATCTAGAACTCCGTTTGTAATGAG-3'        (SEQ ID NO: 84)

5'-TCGACTCATTACAAACGGAGTTCTAGATCT-      (SEQ ID NO: 85)
3'

Amino acid sequence: LDLQLRLGYY        (SEQ ID NO: 86)

5'-ACTGGATCTACAACTCCGTTTGGGTTATTAC      (SEQ ID NO: 87)
TAATGAG-3'

5'-TCGACTCATTAGTAATAACCCAAACGGAGTT      (SEQ ID NO: 88)
GTAGATCCAG-3'

Amino acid sequence: LDLELRL           (SEQ ID NO: 89)

5'-ACTGGATCTAGAACTCCGTTTGTAATGAG-3'     (SEQ ID NO: 90)

5'-TCGACTCATTACAAACGGAGTTCTAGATCC       (SEQ ID NO: 91)
AG T-3'

Amino acid sequence: LDLELAAAAAA       (SEQ ID NO: 92)

5'-ACTGGATCTAGAACTCGCTGCCGCAGCGGCT      (SEQ ID NO: 93)
GCATAATGAG-3'

5'-TCGACTCATTATGCAGCCGCTGCGGCAGCGA      (SEQ ID NO: 94)
GTTCTAGATCCAGT-3'

Amino acid sequence: LDLELRLAAA        (SEQ ID NO: 95)

5'-ACTGGATCTAGAACTCCGTTTGGCTGCCGCA      (SEQ ID NO: 96)
TAATGAG-3'

5'-TCGACTCATTATGCGGCAGCCAAACGGAGTT      (SEQ ID NO: 97)
CTAGATCCAGT-3'

Amino acid sequence: LELDLAAAAAA       (SEQ ID NO: 98)

5'-CCTTGAGCTTGATCTTGCTGCTGCTGCTGCT      (SEQ ID NO: 99)
GCTTGAG-3'

5'-TCGACTCAAGCAGCAGCAGCAGCAGCAAGAT      (SEQ ID NO: 100)
CAAGCTCAAGG-3'

Amino acid sequence: LDLELRLG          (SEQ ID NO: 101)

5'-CCTGGATCTAGAACTCCGTGGTTAAG-3'        (SEQ ID NO: 102)

5'-TCGACTTAACCACGGAGTTCTAGATCCAG        (SEQ ID NO: 103)
G-3'

Amino acid sequence: LELRL             (SEQ ID NO: 104)

5'-TCTA GAA CTC CGT TTG TAA TGA         (SEQ ID NO: 105)
G-3'

5'-TCGACTCA TTA CAA ACG GAG TTC T       (SEQ ID NO: 106)
AG A-3'

Amino acid sequence: FDLNFAPLDCV       (SEQ ID NO: 107)

5'-ATTCGATCTTAATTTTGCACCGTTGGATTGT      (SEQ ID NO: 108)
GTTTAAG-3'

5'-TCGACTCATTAAACACAATCCAACGGTGCAA      (SEQ ID NO: 109)
AATTAAGATCGAAT3'

Amino acid sequence: FDLNIFPPIPEF      (SEQ ID NO: 110)

5'-GTTTGACCTCAACATCCCTCCGATCCCTGAA      (SEQ ID NO: 111)
TTCTAAG-3'

5'-TCGACTTAGAATTCAGGGATCGGAGGGATGT      (SEQ ID NO: 112)
TGAGGTCAAAC-3'

Amino acid sequence: FQFDLNFPPLDCV     (SEQ ID NO: 113)

5'-CTTTCAATTCGATCTTAATTTTCCACCGTTG      (SEQ ID NO: 114)
GATTGTGTTTAAG-3'

5'-TCGACTTAAACACAATCCAACGGTGGAAAAT      (SEQ ID NO: 115)
TAAGATCGAATTGAAAG-3'

Amino acid sequence: DLDLRL            (SEQ ID NO: 116)

5'-ACTGGATCTAGATCTCCGTTTGTAATGA         (SEQ ID NO: 117)
G-3'

5'-TCGACTCATTACAAACGGAGATCTAGATCCA      (SEQ ID NO: 118)
GT-3'
```

Each of a DNA fragment encoding these peptides was incorporated into the plasmid p35S-GAL4DBD that had been previously digested with restriction enzymes, SmaI and SalI, to construct the effector plasmid pGAL4DB-RD.

(2) Construction of Reporter Gene (2-1) Construction of Reporter Gene pGAL4-LUC (FIG. 2)

Plasmid pUC18 was digested with restriction enzymes, EcoRI and SstI. Plasmid pBI221 (Clontech) was digested with restriction enzymes, EcoRI and SstI, and a 270 bp DNA fragment comprising the nopaline synthase terminator (Noster) region was isolated by agarose gel electrophoresis. The resulting fragment was inserted into the EcoRI-SstI site of the plasmid pUC18 that had been digested with restriction enzymes EcoRI and SstI. Complementary strands DNA 1: AGCTTAGATCTGCAAGACCCTTCCTC-TATATAAGGAAGTTCATTTCATTTGGAG AGGA-CACGCTG (SEQ ID NO: 25) and DNA 2: GATCCAGCGT-GTCCTCTCCAAATGAAATGAACTTCCTTATATAGAG GAAGGGT CTTGCAGATCTA (SEQ ID NO: 26) comprising the TATA box of the cauliflower mosaic virus 35S promoter were synthesized.

The synthesized DNA was incubated at 90° C. for 2 minutes, further incubated at 60° C. for 1 hour, and then allowed to stand at room temperature (25° C.) for 2 hours for annealing to form double-stranded DNA. The plasmid pUC18 comprising Nos-ter was digested with restriction enzymes, HindIII and BamHI. The synthesized double-stranded DNA was inserted into the HindIII-BamHI site of pUC18 to construct a plasmid comprising the TATA-box and Nos-ter.

This plasmid was digested with a restriction enzyme, SstI and then blunt-ended with T4 DNA polymerase.

The plasmid vector PGV-CS2 (Toyo Ink Mfg. Co., Ltd.) having the firefly luciferase gene (LUC) was digested with restriction enzymes, XbaI and NcoI and then blunt-ended with T4 DNA polymerase. Thereafter, a 1.65 kb DNA fragment comprising the luciferase gene was isolated and purified by agarose gel electrophoresis. This DNA fragment was inserted into the aforementioned plasmid comprising the TATA box and the Nos-terminator to construct the reporter gene pTATA-LUC.

The plasmid pG5CAT (Clontech) having 5 repeats of the yeast GAL4 DNA-binding domain was digested with restriction enzymes, SmaI and XbaI and blunt-ended with T4 DNA polymerase. Thereafter, a DNA fragment comprising 5 repeats of the GAL4 DNA-binding domain was purified by agarose gel electrophoresis. The TATA-LUC vector was digested with a restriction enzyme, BglII and blunt-ended with T4 DNA polymerase. The blunt-ended DNA fragment comprising 5 repeats of the GAL4 DNA-binding domain was inserted into this site, and a clone in which the GAL4 DNA-binding domain is oriented in the forward direction was selected from among the obtained plasmids to construct the reporter gene pGAL4-LUC (see FIG. 2).

Figure 3:
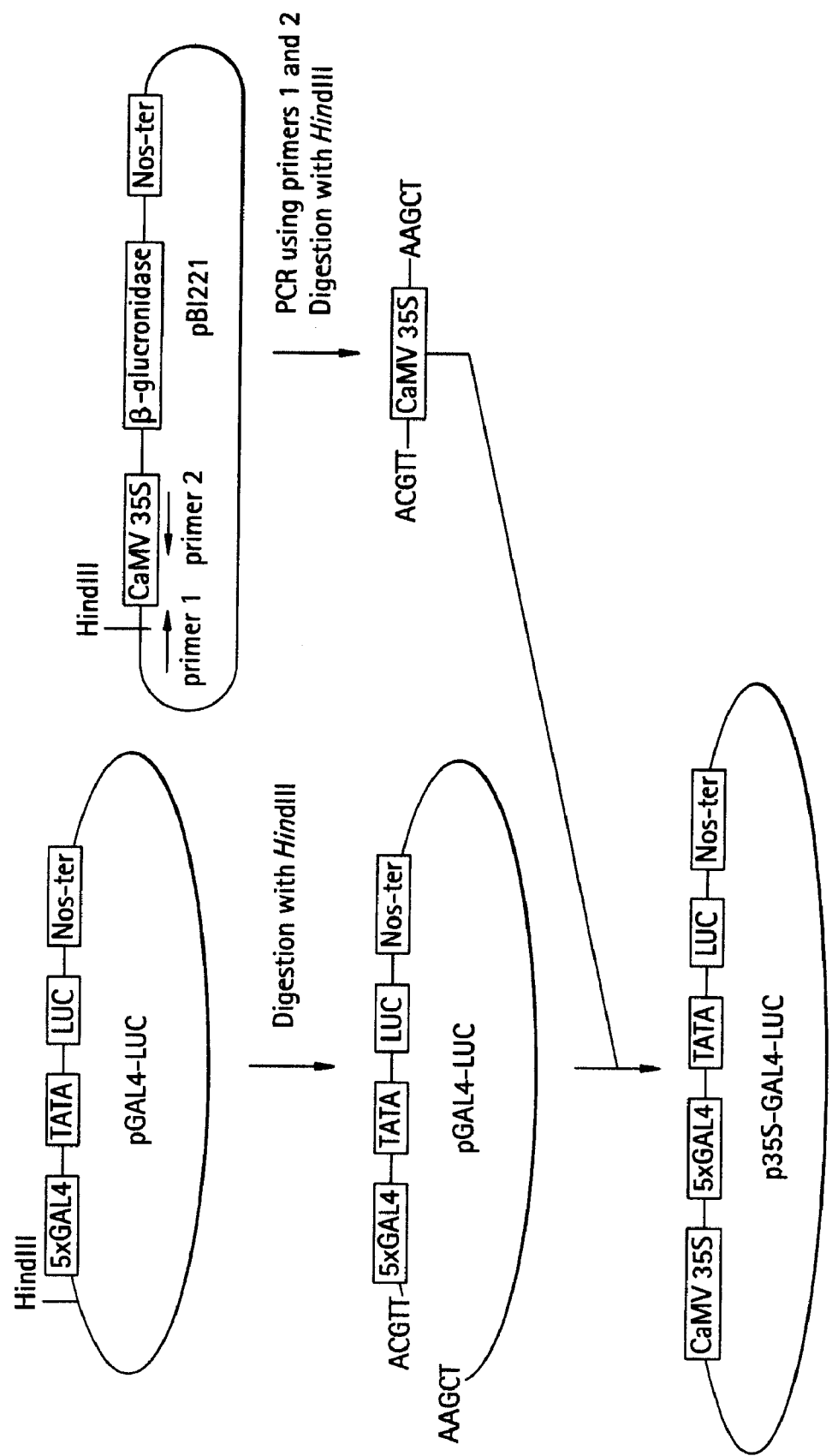
FIG. 3 shows the last half of the procedure for constructing a reporter gene p35S-GAL4-LUC.

(2-2) Construction of p35S-GAL4-LUC (FIG. 3)

PCR was carried out using the plasmid pBI121 as a template and using the 5'-primer: CGCCAGGGTTTTC-CCAGTCACGAC (SEQ ID NO: 27) and the 3'-primer: AAGGGTAAGCTTAAGGATAGTGGGAT-TGTCGTCATC (SEQ ID NO: 28). Thus, a DNA fragment comprising the CaMV 35S promoter domain (from −800 to −46) was obtained. After the digestion with the restriction enzyme, HindIII, a 760 bp DNA fragment comprising the CaMV 35S promoter domain (from −800 to −46) was isolated by agarose gel electrophoresis. This HindIII-CaMV35S fragment was inserted into the reporter gene pGAL4-LUC that had been previously digested with the restriction enzyme, HindIII, and a clone in which DNA of the CaMV 35S promoter is oriented in the forward direction was selected to construct the reporter gene p35S-GAL4-LUC (see FIG. 3).

(3) Construction of Reference Gene

The cassette vector pRL-null (Promega) having the Renilla luciferase gene was cleaved with restriction enzymes NheI and XbaI and blunt-ended with T4 DNA polymerase. Thereafter, a 948 bp DNA fragment comprising the Renilla luciferase gene was purified by agarose gel electrophoresis. This DNA fragment was inserted into a region in the pBI221 vector from which the GUS gene used for constructing the effector plasmid had been removed. A clone in which the Renilla luciferase gene is oriented in the forward direction was selected from among the obtained plasmids (construction of pPTRL).

(4) Method for Assaying of the Activity of Reporter Gene

The reporter gene and the effector plasmid were introduced into Arabidopsis thaliana by the particle gun method, and effects of the effector plasmid were analyzed by assaying activity of the reporter gene.

(5) Gene Introduction Using Particle Gun

Gold grains (510 mg, diameter 1 mm, Bio-Rad) were coated with 1.2 mg of DNA of the reporter gene p35S-GAL4-LUC prepared above, 1.2 mg of DNA of the effector plasmid pGAL4DB-RD prepared above, and 0.32 mg of the reference gene plasmid. Arabidopsis thaliana leaves (7 leaves) of 21 day-old were laid out a water-moistened filter paper in a 9-cm petri dish, and DNA was introduced therein using the PDS 1000/HE device for particle bombardment (Bio-Rad). The leaves were allowed to stand at 22° C. for 6 hours in a well-lit place, and the activity of the reporter gene was then assayed.

(6) Assay of Luciferase Activity

Figure 4A:
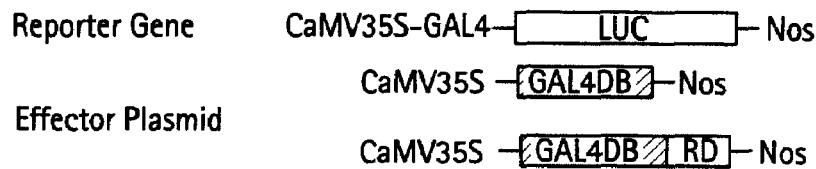
FIG. 4A shows a reporter gene and an effector plasmid.
Figure 4B:
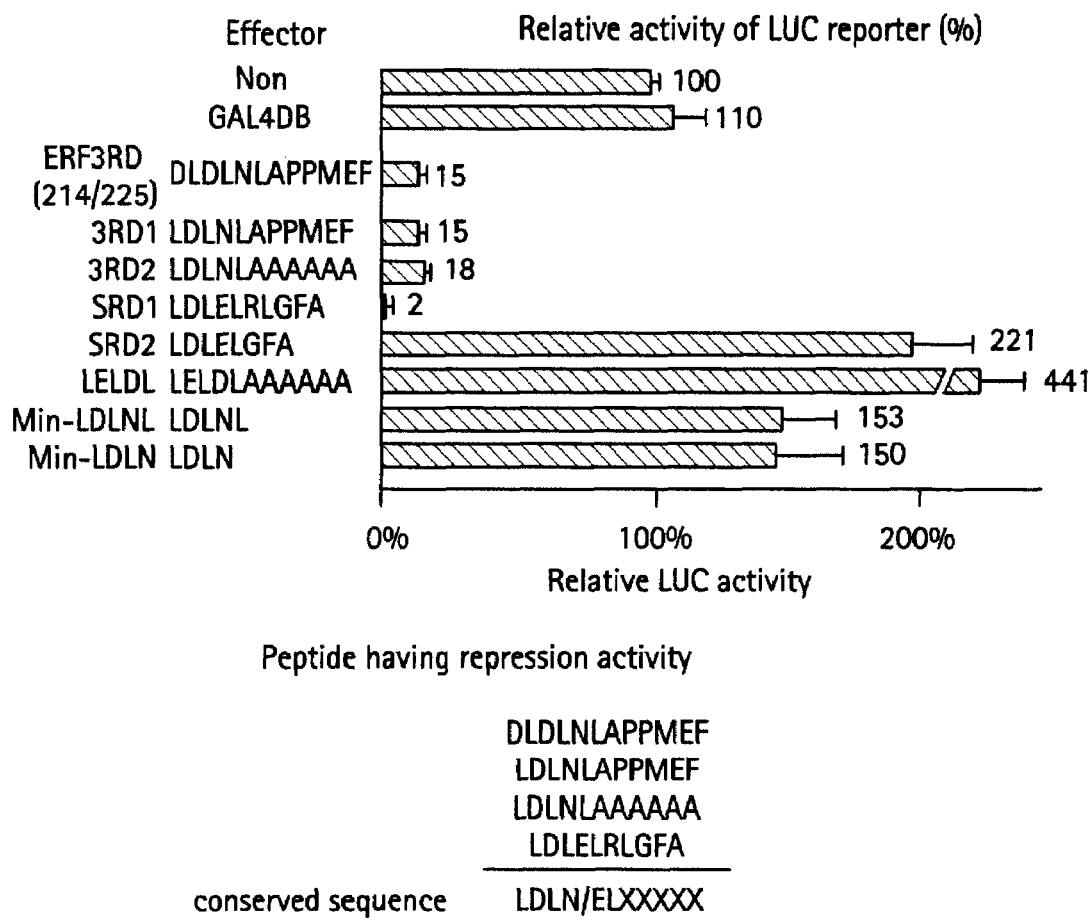
FIG. 4B shows the effects of a variety of peptides (SEQ ID NOS 1, 4, 7, 16, 19, 22, 13, and 10, respectively in order of appearance) fused to pGAL4DB on activity of the reporter gene (relative activity), wherein the graph on the right side shows activity of the reporter gene when the effector plasmid comprising a variety of DNA fragments is introduced (the activity of the reporter gene without the effector plasmid was set to be 100) ERF3RD is SEQ ID NO: 1; 3RD1 is SEQ ID NO: 4; 3RD2 is SEQ ID NO: 7; SRD1 is SEQ ID NO: 16, SRD2 is SEQ ID NO: 19; LELDL is SEQ ID NO: 22; and Min-LDLNL is SEQ ID NO: 13. (peptides shown below are disclosed as SEQ ID NOS 1, 4, 7, 16, and 10, respectively in order of appearance).

The Arabidopsis thaliana leaves that had been allowed to stand for 6 hours were grinded in liquid nitrogen, suspended in 200 µl of the Passive Lysis Buffer from the Dual-Luciferase® Reporter Assay System (Promega), and then centrifuged to recover the supernatant. This cell extract (20 µl) was mixed with 100 µl of the assay buffer attached to the Dual-Luciferase® Reporter Assay System (Promega), and luciferase activity was assayed using a luminometer (TD 20/20, Turner Design). Activity of the firefly luciferase and that of Renilla luciferase were assayed by measuring luminescence over 10 seconds in the integral mode in accordance with the instructions of the assay kit. A value indicating reference gene activity was divided by a value indicating reporter gene activity, and the relative value thereof, i.e., the relative luciferase activity, was determined as a measured value. Each type of effector plasmid was subjected to a transient assay for three times, and the mean and the standard deviation were determined. The relative activity value of the reporter gene p35S-GAL4-LUC without the effector plasmid was set to be 100, and effects of the effector plasmid were analyzed based on variations in values of the reporter gene activity when the effector plasmid was co-expressed in cells. Specifically, if the value indicating reporter gene activity decreases upon introduction of the reporter gene p35S-GAL4-LUC and the effector plasmid pGAL4DB-RD comprising DNA encoding each peptide sequence incorporated therein, such decrease indicates that the peptide has the effect of repressing the activity of the reporter gene (repression activity). When the reporter gene activity was measured and the relative activity value of the reporter gene p35S-GAL4-LUC became 100 or smaller, the effector plasmid introduced was determined to have a repression activity (7) Identification of Repression Domain FIG. 4A shows the structure of the reporter gene and that of the effector plasmid. FIG. 4B and Table 1 below show the results of assaying of activity of reporter gene.

TABLE 1

| Identification of peptide | Peptide sequence | Relative value (%) | SEQ ID NO: |
|---|---|---|---|
| ERF3RD (214/225) | DLDLNLAPPMEF | 15.0 | 1 |
| 3RD1 | LDLNLAPPMEF | 14.6 | 4 |
| 3RD2 | LDLNLAAAAAA | 17.5 | 7 |
| SRD1 | LDLELRLGFA | 2.0 | 16 |
| SRD2 | LDLELGFA | 221 | 19 |
| LELDL | LELDLAAAAAA | 196 | 22 |
| Min-LDLN | LDLN | 153 | 10 |
| Min-LDLNL | LDLNL | 150 | 13 |
| | LELRLAAAAAA | 130.6 | 80 |
| | DLELRL | 8.9 | 83 |
| | LDLQLRLGYY | 3.8 | 86 |
| | LDLELRL | 4.5 | 89 |
| | LDLELAAAAAA | 72.5 | 92 |
| | LDLELRLAAA | 6.9 | 95 |
| | LELDLAAAAAA | 196.0 | 98 |
| | LDLELRLG | 8.9 | 101 |
| | LELRL | 101.5 | 104 |
| | FDLNFAPLDCV | 17.5 | 107 |
| | FDLNIFPPIPEF | 16.0 | 110 |
| | FQFDLNFPPLDCV | 10.9 | 113 |
| | DLDLRL | 9.2 | 116 |
| Control | GAL4DB alone | 100 | |

According to the above results, activity of reporter gene of a peptide comprising LDL(N/E)L (SEQ ID NO: 128) or FDLN(F/I) (SEQ ID NO: 129) and at least 6 amino acid residues at its C-terminus or a peptide comprising DL(E/Q/D)LRL (SEQ ID NO: 130) decreases by 85% to 98%, in comparison with that of the reporter gene (containing no effector plasmid, i.e., the control). This demonstrates that the aforementioned peptides serve as functional peptides capable of repressing transcriptions of genes.

The control p35S-GAL4DBD, which does not contain the coding sequence for the peptide, did not effect the activity of the reporter gene. This indicates that the aforementioned peptide bound to the GAL4 DNA-binding domain serves as a repressor of transcription.

EXAMPLE 2

Repression of Transcription by SUP Gene-containing Effector Plasmid (1) Isolation of SUP Gene The nucleotide sequence of the SUP gene has already been reported. Oligonucleotides having sequences corresponding to the sequences on the 5'-side and the 3'-side of the protein-encoding region of the SUP gene of *Arabidopsis thaliana* were synthesized, and PCR was carried out using the resulting sequences as primers and using the TAC clone:K14B15 (assigned from the Kazusa DNA Research Institute) comprising the SUP gene as a template. The DNA fragment comprising the protein-encoding region of the SUP gene was isolated. The total nucleotide sequence was determined, and it was confirmed to be the protein-encoding region of the SUP gene that had been already reported. The conditions for the aforementioned PCR was as follows: 25 cycles each consisting of denaturation at 94° C. for 1 minute; annealing at 47° C. for 2 minutes; and elongation at 74° C. for 1 minute.

Figure 5A:
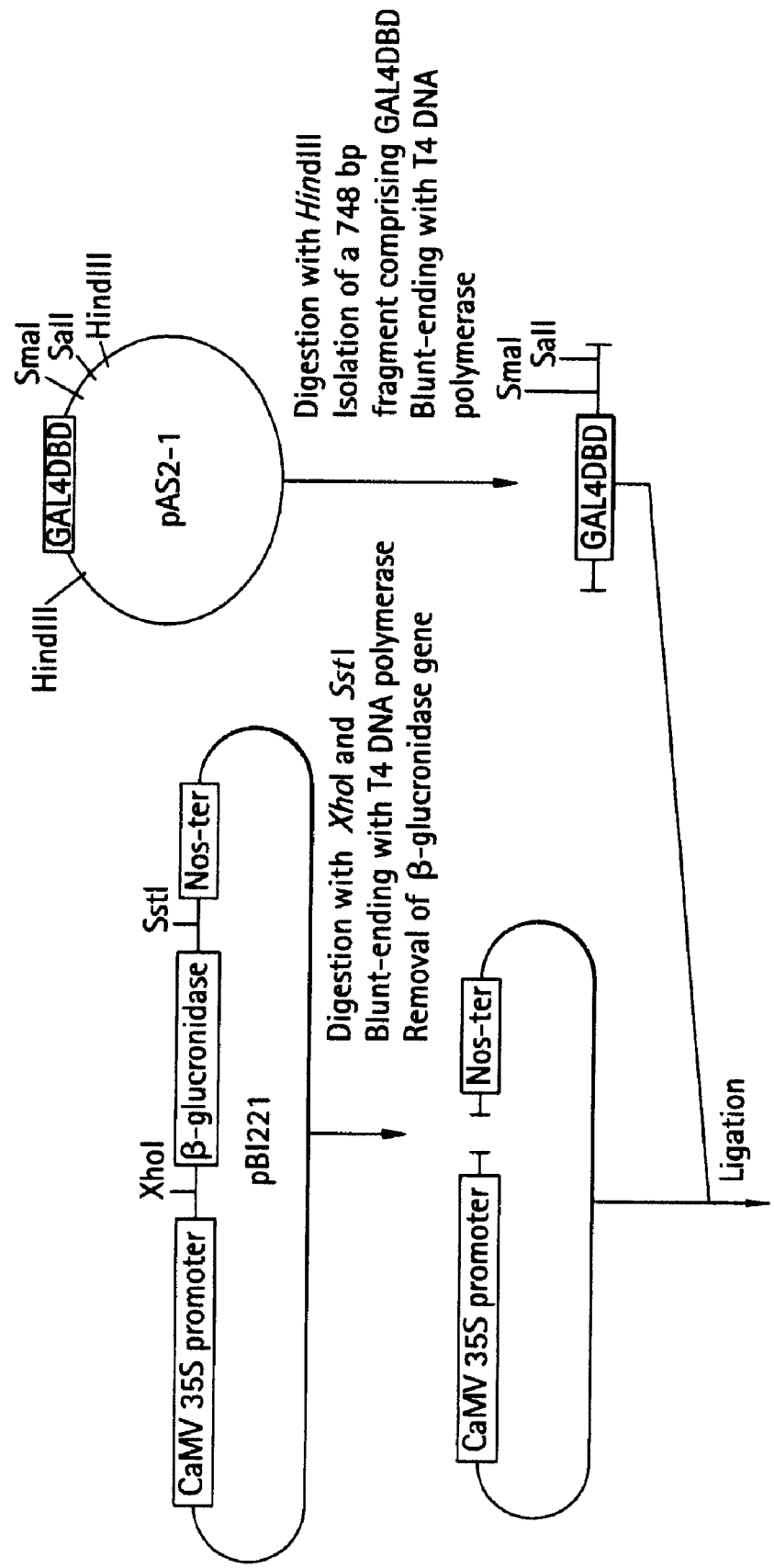
Figure 5B:
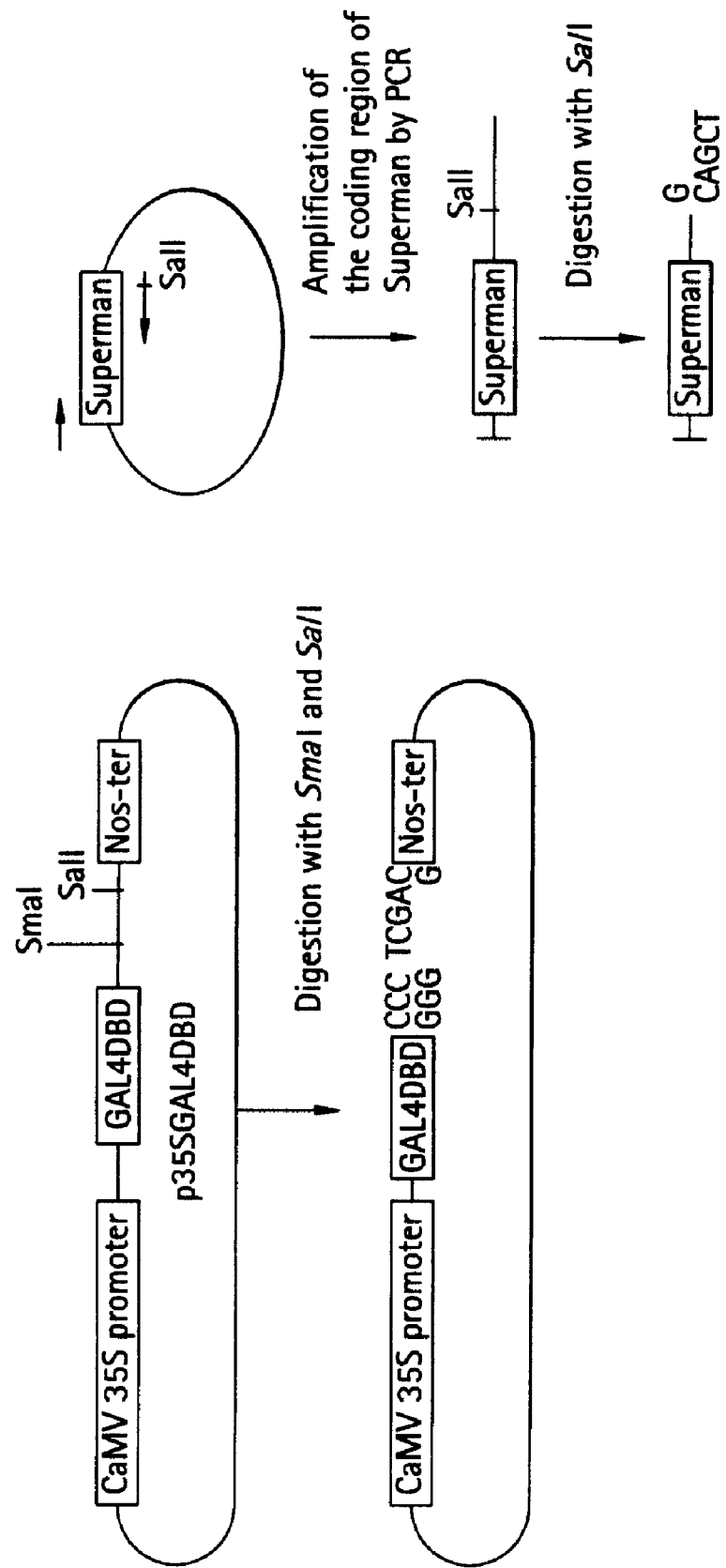
Figure 5C:
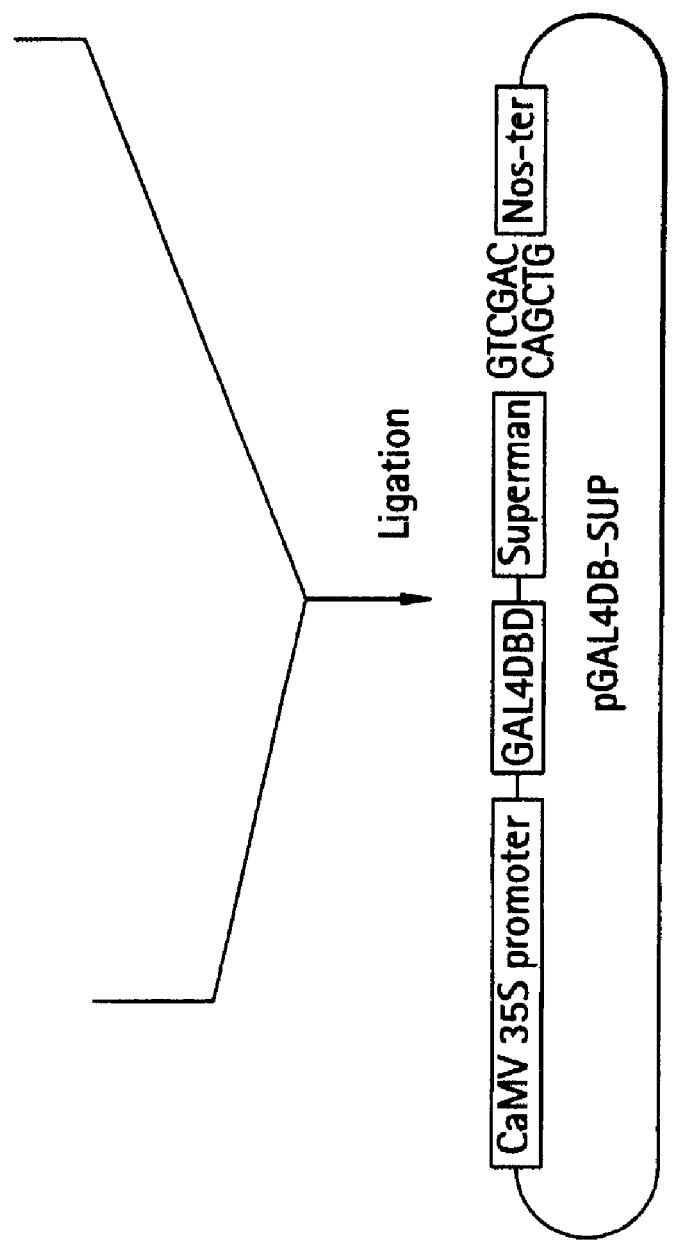

(2) Construction of Effector Plasmid (2-1) Construction of Effector Plasmid, pGAL4DB-SUP, Comprising the Full-length Protein-encoding Region of the SUP Gene (FIG. 5)

Plasmid pBI221 (Clontech, U.S.A.) was cleaved with restriction enzymes, XhoI and SacI, and the GUS gene was removed by agarose gel electrophoresis and blunt-ended with T4 polymerase, to obtain a fragment of 35S-Nos plasmid DNA comprising CaMV 35S and Nos-ter.

The pAS2-1 vector (Clontech) was digested with a restriction enzyme, HindIII, GAL4DBD, i.e., a transcription activator of yeast, was isolated by agarose gel electrophoresis, and the isolated fragment was blunt-ended with T4 DNA polymerase. This DNA fragment comprising the GAL4DBD-encoding region was inserted in the blunt-ended site between the 35S promoter and the Nos terminator of the aforementioned 35S-Nos DNA fragment, and a clone in which the ORFs of the DNA-binding domain of the yeast GAL4 protein are oriented in the forward direction to the 35S promoter was selected to construct a p35S-GAL4DBD vector.

PCR was carried out using the 5'-primer 1: GATG-GAGAGATCAAACAGC (SEQ ID NO: 29, bound to the nucleotide sequence (the 1/18 region) of the SUP gene) of the SUP gene and the 3'-primer 2: GATAAAGTTATTAC-CGTCGACTTAAGCGAAAC (SEQ ID NO: 30, bound to the nucleotide sequence (the 602/641 region) of the SUP gene) having a restriction enzyme, SalI site, each of which had been designed to have the reading frame to be in-frame with that of GAL4DBD, to amplify the total protein-encoding region of the SUP gene (SEQ ID NO: 31, the 1/204 amino acid sequence) to obtain a DNA fragment. The conditions for PCR was as follows: 25 cycles each consisting of denaturation at 94° C. for 1 minute; annealing at 47° C. for 2 minutes; and elongation at 74° C. for 1 minute. Hereafter, all PCRs were carried out under the same conditions. The resulting DNA fragment was digested with a restriction enzyme, SalI, and the DNA fragment of interest was isolated by agarose gel electrophoresis. This SUP-encoding DNA fragment was incorporated into the plasmid p35S-GAL4DB that had been previously digested with restriction enzymes, SmaI and SalI to construct the effector plasmid pGAL4DB-SUP.

(2-2) Construction of Effector Plasmid pGAL4DB-175/204SUP Comprising the Amino Acid Sequence (the 175/204 region) of SUP PCR was carried out using the 5'-primer 3: GAATGAT-GAAATCATCAG (SEQ ID NO: 32, bound to the nucleotide sequence (the 522/539 region) of the SUP gene) and the 3'-primer 2: GATAAAGTTATTACCGTCGACTTAAGC-GAAAC (SEQ ID NO: 30, bound to the nucleotide sequence (the 602/641 region) of the SUP gene) having the restriction enzyme, SalI site, each of which had been designed to have the reading frame to be in-frame with that of GAL4DBD, to obtain a DNA fragment comprising a nucleotide sequence (the 523/612 region) corresponding to the region encoding the amino acid sequence (the 175/204 region) of SUP. This DNA fragment was digested with a restriction enzyme, SalI, the DNA fragment of interest was isolated by agarose gel electrophoresis, and the nucleotide sequence thereof was determined. A DNA fragment (the 523/612 region) encoding the amino acid sequence (the 175/204 region) of SUP was incorporated into the plasmid 35S-GAL4DBD that had been previously digested with restriction enzymes, SmaI and SalI, to construct the effector plasmid pGAL4DB-175/204SUP.

Figure 6A:
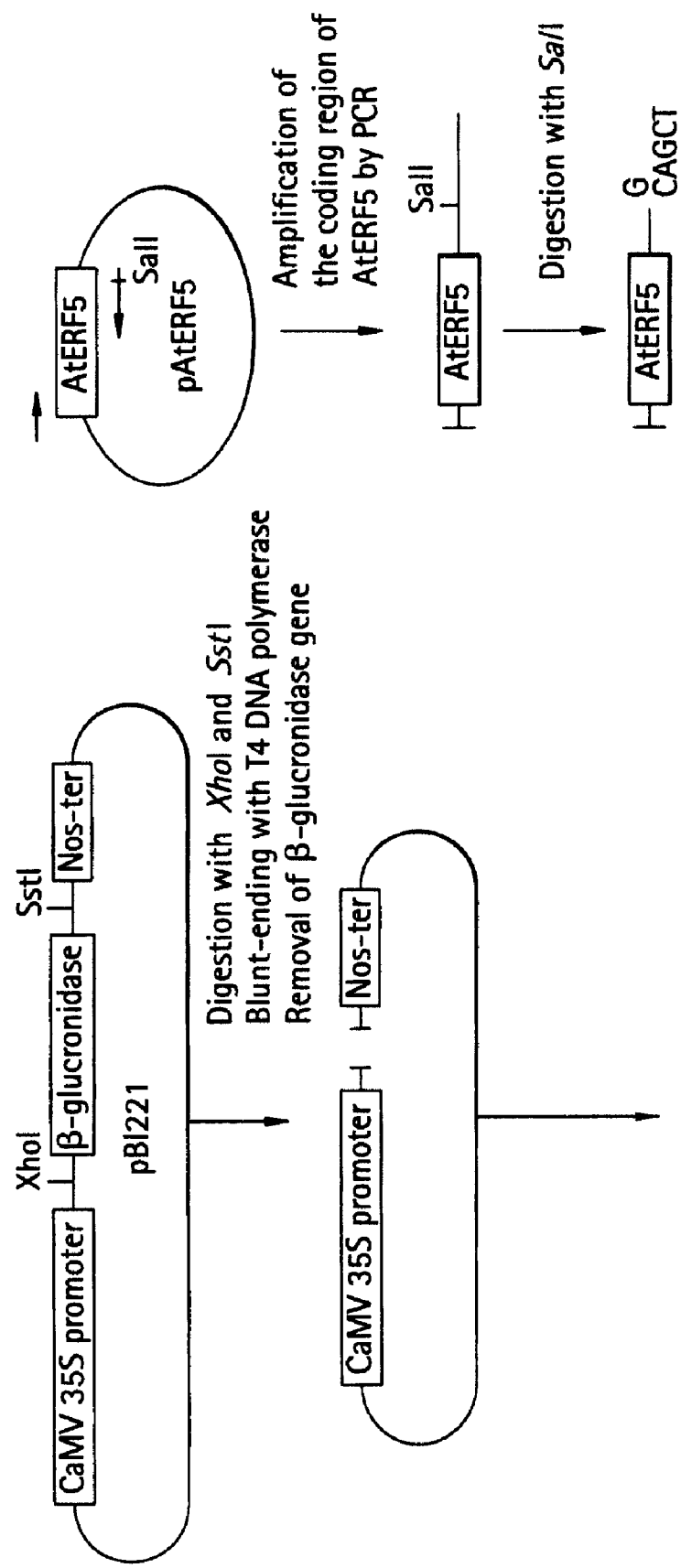
FIG. 6 shows a procedure for constructing the effector plasmid pAtERF5.
Figure 6B:
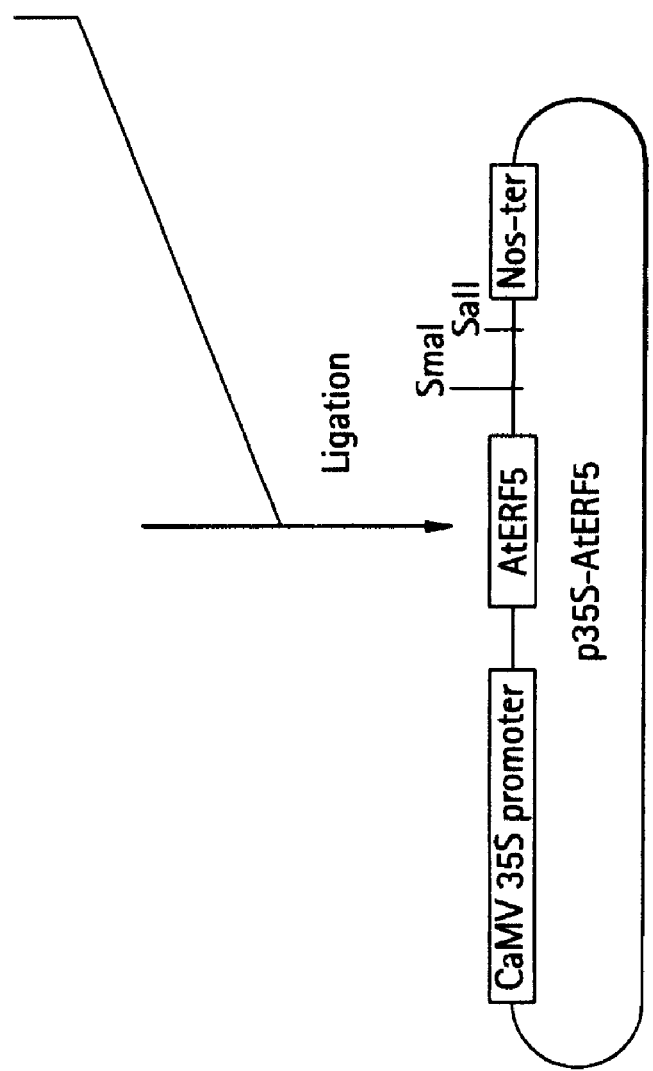

(2-3) Construction of Control Effector Plasmid (FIG. 6)

PCR was carried out using the clone pAtERF5 comprising *Arabidopsis thaliana* AtERF5cDNA as a template and using the 5'-primer 4: CATGGCGACTCCTAACGAAGTATCTG-CAC (SEQ ID NO: 33) and the 3'-primer 5: ATCGT-TCAAAAACTCAAGGCTAACTAATCAACAACGGTC (SEQ ID NO: 34) to amplify the full-length protein-encoding region of AtERF5. This DNA fragment was cloned into the aforementioned blunt-ended 35S-Nos plasmid fragment to construct the effector plasmid p35S-AtERF5.

Separately, the effector plasmid pGAL4DB was constructed in the same manner as described above, except that the SUP gene and 175/204 SUP were not used.

(3) Construction of Reporter Gene

Two types of reporter genes, p35S-GAL4-LUC and pGAL4-GCC-LUC, were constructed in the following procedure.

(3-1) Construction of p35S-GAL4-LUC (FIG. 2 and FIG. 3)

a. Construction of pGAL4-LUC (FIG. 2)

Plasmid pUC18 was digested with restriction enzymes, EcoRI and SstI. Separately, plasmid pBI221 (Clontech) was digested with restriction enzymes, EcoRI and SstI, and a 270 bp DNA fragment comprising the nopaline synthase terminator (Nos-ter) region was isolated by agarose gel electrophoresis. The resulting fragment was inserted into the EcoRI-SstI site of the plasmid pUC18 that had been digested with restriction enzymes EcoRI and SstI. Subsequently, complementary strands of DNA 1: AGCTTAGATCTG-CAAGACCCTTCCTCTATATAAGGAAGT-TCATTTCATTTGGAG AGGACACGCTG (SEQ ID NO: 35) and DNA 2: GATCCAGCGTGTCCTCTCCAAAT-GAAATGAACTTCCTTATATAGAGGAAGGGT CTTG-CAGATCTA (SEQ ID NO: 36) comprising the TATA box of the cauliflower mosaic virus 35S promoter were synthesized.

The synthesized DNA was incubated at 90° C. for 2 minutes, further incubated at 60° C. for 1 hour, and then allowed to stand at room temperature (25° C.) for 2 hours for annealing to prepare double-stranded DNA. The plasmid pUC18 comprising Nos was digested with restriction enzymes, HindIII and BamHI. The synthesized double-stranded DNA was inserted into the HindIII-BamHI site of pUC18 to construct a plasmid comprising the TATA-box and Nos-ter.

This plasmid was digested with a restriction enzyme, SstI and then blunt-ended with T4 DNA polymerase.

Separately, the plasmid vector PGV-CS2 (Toyo Ink Mfg. Co., Ltd.) having the firefly luciferase gene (LUC) was digested with restriction enzymes, XbaI and NcoI and then blunt-ended with T4 DNA polymerase. Thereafter, a 1.65 kb DNA fragment comprising the luciferase gene was isolated and purified by agarose gel electrophoresis. This DNA fragment was inserted into the aforementioned plasmid comprising the TATA box and the Nos-terminator to construct the reporter gene pTATA-LUC.

The plasmid pG5CAT (Clontech) having 5 repeats of the yeast GAL4 DNA-binding domain was digested with restriction enzymes, SmaI and XbaI and blunt-ended with T4 DNA polymerase. Thereafter, a DNA fragment comprising 5 repeats of the GAL4 DNA-binding domain was purified by agarose gel electrophoresis. The TATA-LUC vector was digested with a restriction enzyme, BglII and blunt-ended with T4 DNA polymerase. The blunt-ended DNA fragment comprising 5 repeats of the GAL4 DNA-binding domain was inserted into this restriction site, a clone in which the GAL4 DNA-binding domain is oriented in the forward direction was selected from among the obtained plasmids to construct the reporter gene pGAL4-LUC (see FIG. 2).

b. Construction of p35S-GAL4-LUC (FIG. 3)

PCR was carried out using the plasmid pBI121 as a template and using the 5'-primer 6: CGCCAGGGTTTTC-CCAGTCACGAC (SEQ ID NO: 37) and the 3'-primer 7: AAGGGTAAGCTTAAGGATAGTGGGAT-TGTGCGTCATC (SEQ ID NO: 38). Thus, a DNA fragment comprising the CaMV 35S promoter domain (from −800 to −46) was obtained. After the digestion with the restriction enzyme, HindIII, a 760 bp DNA fragment comprising the CaMV 35S promoter domain (from −800 to −46) was isolated by agarose gel electrophoresis. This HindIII fragment was inserted into the reporter gene pGAL4-LUC that had been previously digested with the restriction enzyme, HindIII, and a clone in which DNA of the CaMV 35S promoter is oriented in the forward direction was selected to construct the reporter gene p35S-GAL4-LUC (see FIG. 3).

Figure 7B:
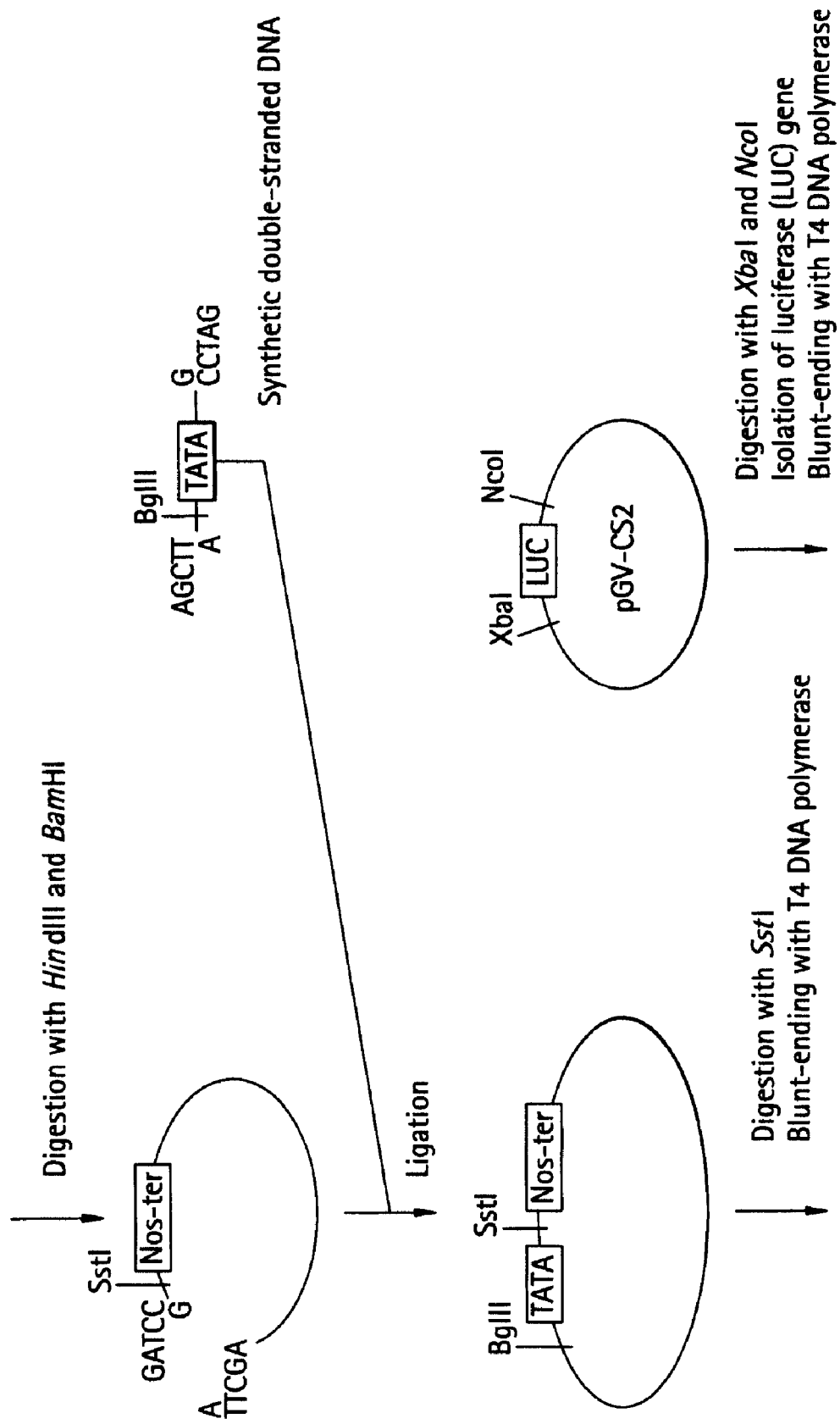
FIG. 7 shows the first half of the procedure for constructing the reporter plasmid pGAL4-GCC-LUC.
Figure 7C:
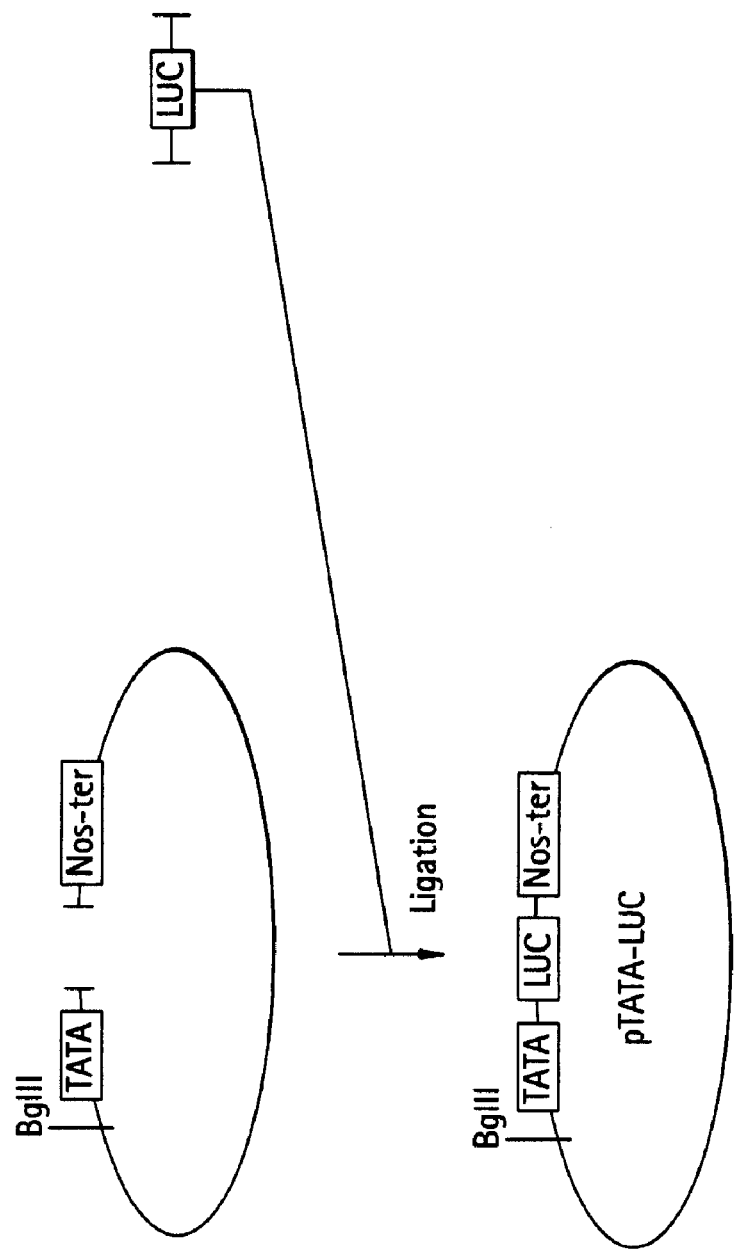
Figure 7D:
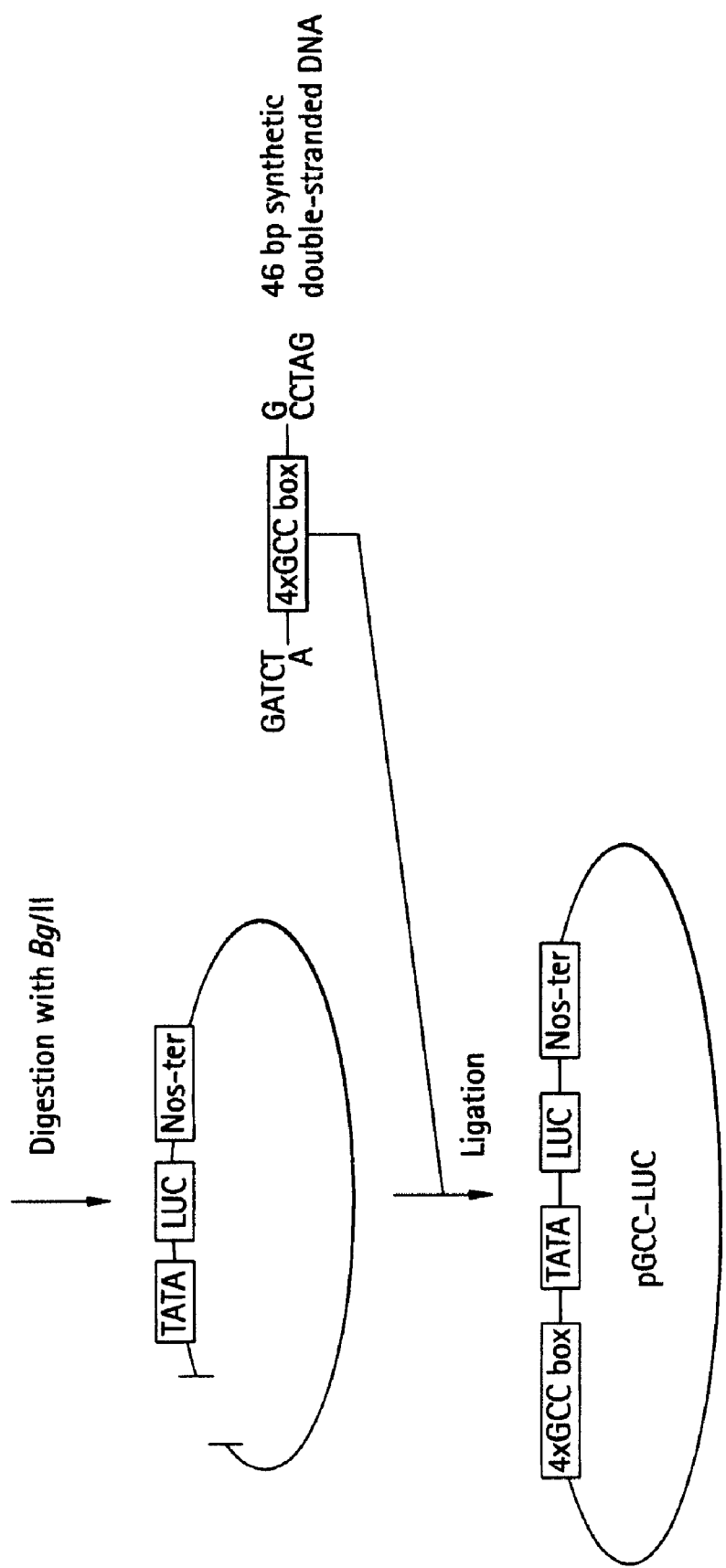
Figure 8:
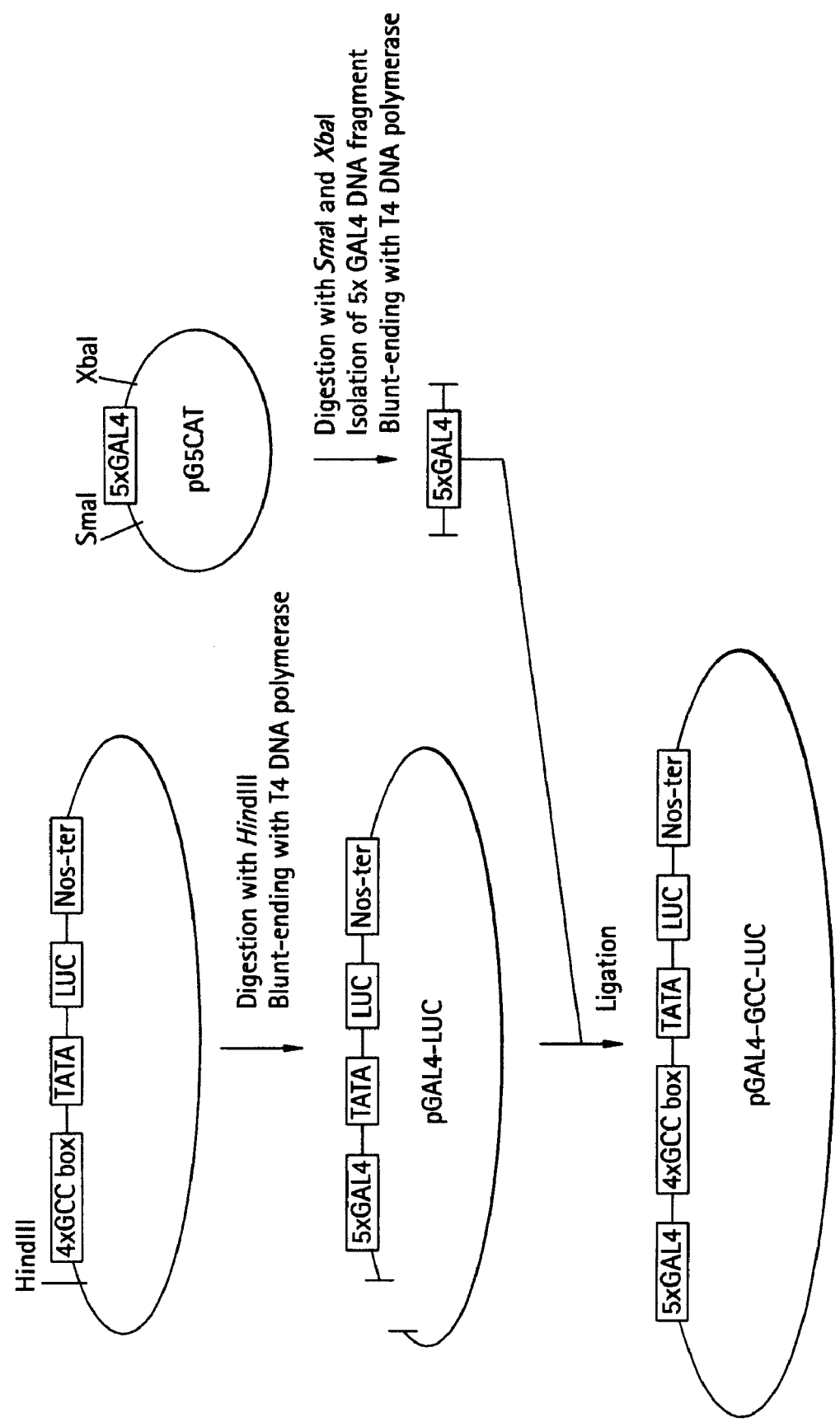
FIG. 8 shows the last half of the procedure for constructing the reporter plasmid pGAL4-GCC-LUC.

(3-2) Construction of pGAL4-GCC-LUC (FIG. 7 and FIG. 8)

Complementary strands (shown below) of a 45 bp DNA fragment comprising 4 GCC box sequences (AGCCGCC) were synthesized. The synthesized strands were incubated at 70° C. for 15 minutes and allowed to stand at room temperature for 60 minutes for annealing to prepare double-stranded DNA.

```
                                            (SEQ ID NO: 39)
5'-GATCAGCCGCCGATCAGCCGCCGATCAGCCGCCGATCAGCCGCC-3'

(SEQ ID NO: 40)
3'-TCGGCCGGCTAGTCGGCGGCTAGTCGGCGGCTAGTCGGCGGGATC-5'
```

This 45 bp DNA fragment was mixed with the aforementioned TATA-LUC vector that had been previously digested with a restriction enzyme BglII at a molar ratio of 1:1, ligation was carried out using T4 ligase, and a clone in which a GCC box-containing DNA fragment is oriented in the forward direction was selected to construct the plasmid pGCC-LUC. This plasmid was digested with a restriction enzyme, BglII and blunt-ended with T4 DNA polymerase (see FIG. 7).

The plasmid pG5CAT (Clontech) having 5 repeats of the yeast GAL4 DNA-binding domain was digested with restriction enzymes, SmaI and XbaI and blunt-ended with T4 DNA polymerase. Thereafter, a DNA fragment comprising 5 repeats of the GAL4 DNA-binding domain was purified by agarose gel electrophoresis. This DNA fragment was inserted into the blunt-ended plasmid pGCC-LUC, and a clone in which the GAL4 sequence is oriented in the forward direction was selected to construct the reporter gene pGAL4-GCC-LUC (see FIG. 8).

(4) Gene Introduction Using Particle Gun

Gold particles (510 μg, diameter 1 mm, Bio-Rad) were coated with 1.6 μg of the reporter gene pGAL4-LUC, 1.2 μg of DNA of the effector plasmid pGAL4DB-SUP or a deletion thereof, pGAL4DB-175/204SUP, 1.2 μg of the control plasmid p35S-AtERF5 or pGAL4DB, and 0.32 μg of the reference gene plasmid. *Arabidopsis thaliana* leaves (7 leaves) on the 21st day of growing were laid out in a 9-cm petri dish on a water-moistened filter paper, and DNA was introduced therein using the PDS 1000/HE device for particle bombardment (Bio-Rad). Subsequently, the leaves were allowed to stand at 22° C. for 6 hours in a well-lit place, and reporter gene activity was then assayed.

(5) Assay of Luciferase Activity

The *Arabidopsis thaliana* leaves that had been allowed to stand for 6 hours were grinded in liquid nitrogen, allowed to become suspended in 200 μl of the Passive Lysis Buffer from the Dual-Luciferase® Reporter Assay System (Promega), and then centrifuged to recover the supernatant. This cell extract (20 μl) was mixed with 100 μl of the assay buffer attached to the Dual-Luciferase® Reporter Assay System (Promega), and luciferase activity was assayed using a luminometer (TD 20/20, Turner Design). Activity of firefly luciferase and that of *Renilla* luciferase were assayed by measuring luminescence over 10 seconds in the integral mode in accordance with the instructions of the assay kit. A value indicating reference gene activity was divided by a value indicating reporter gene activity, and the relative value thereof, i.e., the relative luciferase activity, was determined as a measured value. Each type of effector plasmid was independently subjected to repeat a transient assay three times, and the mean and the standard deviation were determined. The relative activity value of the reporter gene p35S-GAL4-LUC without the effector plasmid was set to be 100, and the relative activity value of the reporter gene pGAL4-GCC-LUC was set to be 1. Effects of the effector plasmid were then inspected based on variations in values indicating reporter gene activity when the effector plasmid was simultaneously introduced into cells.

Figures 9A, 9B:
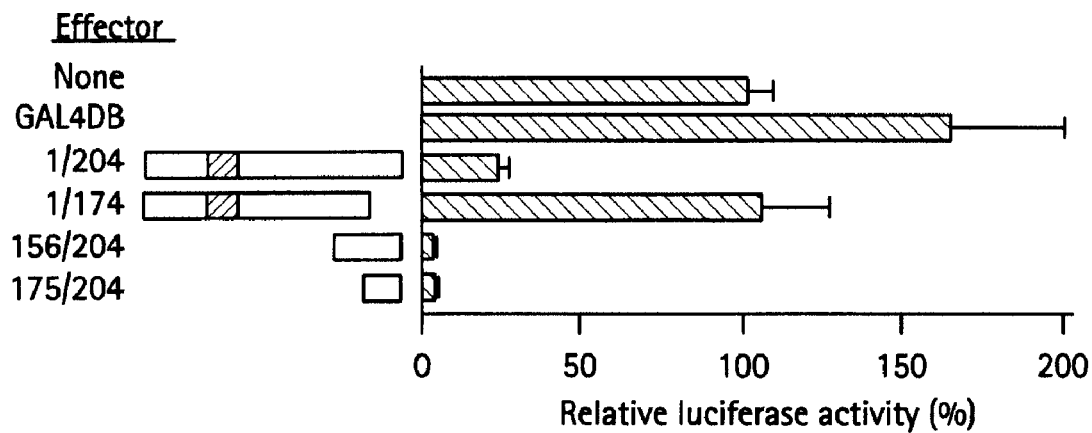
FIG. 9A schematically shows the structure of 35S-GAL4-LUC that was incorporated in a plasmid as a reporter gene and the structure of SUP(D) that was incorporated as an effector gene in the transcriptional repression test.
FIG. 9B shows the results of the test for transcriptional repression activities using the SUP gene and a fragment thereof.

FIG. 9A shows the reporter gene and the effector plasmid, wherein 5×GAL4 represents the DNA-binding sequence of the GAL4 transcription factor; TATA represents a region comprising the TATA box of the CaMV 35S promoter; LUC represents a luciferase gene; CaMV 35S represents the 35S protein gene promoter derived from the cauliflower mosaic virus: GAL4DB represents a region encoding DNA-binding domain of an yeast GAL4 transcription factor; and Nos represents the transcription terminator of the nopaline synthase gene.

FIG. 9B shows the effects of SUP and deleted SUP on reporter gene activity (relative activity), wherein numerical values on the left (such as 175/204) indicate the residues constituting an amino acid sequence of SUP, the box in the center represents an amino acid sequence corresponding to the numerical values on the left, and the graph on the right represents reporter gene activity upon introduction of the effector plasmid having the region shown on the left.

According to the results shown in FIG. 9B, the value indicating reporter gene activity decreases upon co-expression of of the reporter gene p35S-GAL4-LUC and the effector plasmid pGAL4DB-SUP. This indicates that pGAL4DB-SUP has the effect of repressing activity of reporter gene (functions as a repressor). The effector plasmid pGAL4DB-SUP caused the reporter gene activity to decrease by 75%, in comparison with the activity when the effector was not introduced (i.e., the control) (FIG. 9B, 1/204). The control p35S-GAL4DB that did not contain any encoding region of SUP did not suppress the activity of the reporter gene. This indicates that SUP serves as a repressor of transcription.

The effector plasmid pGAL4DB-175/204SUP having a DNA fragment from which the protein-encoding region of the SUP gene had been deleted exhibited greater repressing effects than the case where pGAL4DB-SUP had been expressed. Thus, this effector plasmid was found to repress 95% of reporter gene activity (FIG. 9B, 175/204SUP).

This result demonstrates that the domain having functions as a repressor of SUP (the repression domain) existed in the amino acid sequence (the 175/204 region) of SUP. This amino acid sequence is shown in SEQ ID NO: 61.

Figures 10A, 10B:
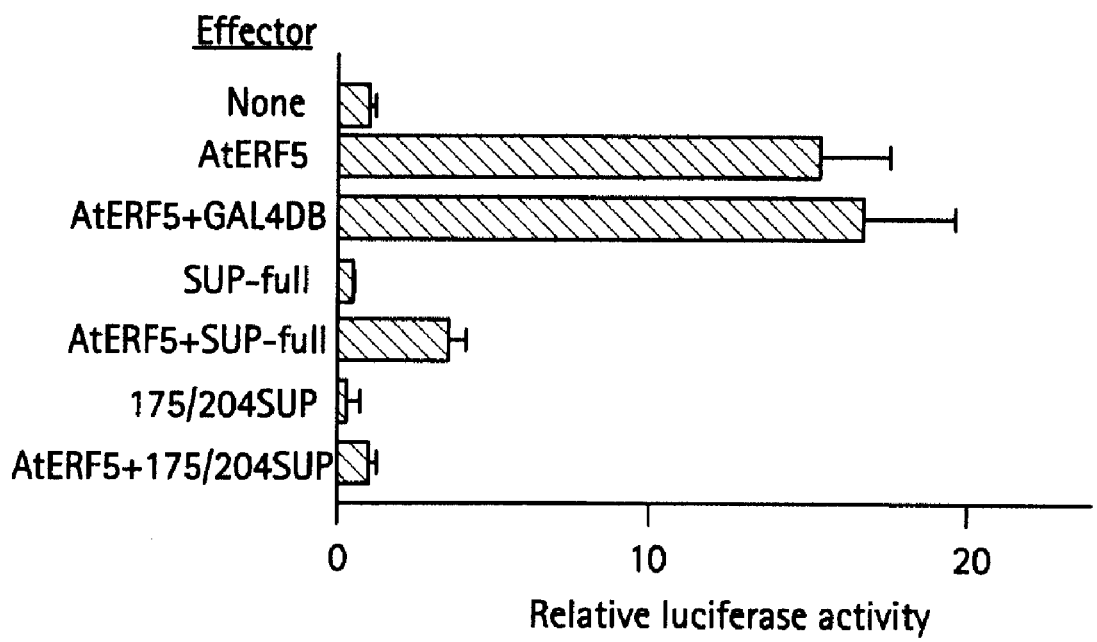
FIG. 10A schematically shows the structure of GAL4-GCC-LUC which was used as a reporter gene and structures of effector genes constructed by incorporating AtERF5, GAL4DB, GAL4 DB-SUP, and GAL4DB175/204SUP, respectively, in the transcriptional repression test.
FIG. 10B shows the results of the transcriptional repression test using each effector plasmid.

FIG. 10A shows the reporter gene pGAL4-GCC-LUC and a variety of effector plasmids.

According to FIG. 10B, reporter gene activity became at least 15 times higher when the reporter gene pGAL4-GCC-LUC and the effector plasmid p35S-AtTERF5 that was known to be capable of activating transcription were expressed into *Arabidopsis thaliana* leaves using a particle gun, in comparison with the case where effector plasmid was not introduced (=1). When the reporter gene was co-expressed with p35S-AtERF5 and pGAL4DB-SUP, the reporter gene activity was increased as low as approximately 2.5 times. This indicates that the SUP protein has the effect of repressing 84% (1-2.5/15) of the activity of AtERF5 for activating transcription. Further, when pGAL4DB-175/204SUP having a region deleted from SUP was co-expressed with the reporter gene GAL4-GCC-LUC and the effector plasmid pATERF5, 90% of the reporter gene activity was repressed. When pGAL4DB was expressed, elevation of reporter gene activity by p35S-AtERF5 was not affected. This indicates that the effect of the reporter gene for repressing transcription is due to the SUP protein.

EXAMPLE 3

Effects of Gene Encoding the 175/204 Repression Domain of SUP in Repressing Transcriptions Activated by EIN3 in Plants (1) Construction of Transformation Vector pBIG2

Plasmid p35S-GFP (Clontech, U.S.A.) was cleaved with restriction enzymes, HindIII and BamHI, a DNA fragment comprising the cauliflower mosaic virus 35S promoter (CaMV 35S) was separated by agarose gel electrophoresis, and the separated fragment was recovered. The plant transformation vector pBIG-HYG assigned from Michigan State University, U.S.A. (Becker, D., 1990, Nucleic Acid Research, 18: 203) was cleaved with restriction enzymes, HindIII and SstI, and a DNA fragment from which the GUS gene had been removed by agarose gel electrophoresis was obtained.

The following DNA strands were synthesized, incubated at 70° C. for 10 minutes, and annealed by natural cooling to prepare double-stranded DNA. This DNA fragment comprises BamHI restriction site at its 5' terminus, the omega sequence derived from the tobacco mosaic virus for improving translation efficiency, and the SmaI and SalI restriction sites.

(SEQ ID NO: 41)
5'-GATCCACAATTACCAACAACAACAAACAACAAACAACATTACAATTA
CAGATCCCGGGGGTACCGTCGACGAGCTC-3'

(SEQ ID NO: 42)
5'-CGTCGACGGTACCCCCGGGATCTGTAATTGTAATGTTGTTTGTTGTTT
GTTGTTGTTGGTAATTGTG-3'

A DNA fragment comprising the CaMV 35S promoter region and the synthesized double-stranded DNA were inserted into the HindIII-SstI site of pBIG-HYG from which the GUS gene had been removed. Thus, the plant transformation vector pBIG2 was obtained.

(2) Construction of Transformation Vector pEIN3SUPRD

PCR was carried out using the clone pEIN3 comprising the full-length cDNA of EIN3 assigned from the Salk Institute, U.S.A. as a template and using the 5'-primer 8: AATGATGTTTAATGAGATGGG (SEQ ID NO: 43) and the 3'-primer 9: ATGAATCCCCGGGATATTATTC (SEQ ID NO: 44) to amplify a DNA fragment comprising the nucleotide sequence (the 1/485 region) corresponding to the region encoding the amino acid sequence (the 1/162 region) of EIN3. The amplified fragment was cleaved with a restriction enzyme, SmaI, and the DNA fragment of interest was isolated by agarose gel electrophoresis. This fragment was inserted into pBIG2, which had been cleaved with a restriction enzyme, SmaI, and a clone that had been cloned in the forward direction was isolated to obtain pBIG2/EIN3-1/162.

The clone pEIN3 comprising the full-length cDNA of EIN3 was cleaved with restriction enzymes, SmaI and PstI, and a DNA fragment (the 487/1695 region) encoding the amino acid sequence (the 163/565 region) of EIN3 was isolated by agarose gel electrophoresis. This DNA fragment was inserted into the cloning vector pBluescriptII that had been cleaved with restriction enzymes, SmaI and PstI to prepare the plasmid pEIN3-163/565.

PCR was carried out using the clone pEIN3 comprising the full-length cDNA of EIN3 as a template and using the 5'-primer 10: CGACACTGCAGATCACAAC (SEQ ID NO: 45) and the 3'-primer 11: ATCCCGAACCATATGGATA-CATCTTGCTGC (SEQ ID NO: 46) in which the stop codon TAA at the 3-terminus had been converted to CCC to amplify a DNA fragment comprising the nucleotide sequence (the 1696/1884 region) corresponding to the region encoding the amino acid sequence (the 566/628 region) of EIN3. The amplified fragment was cleaved with a restriction enzyme, PstI, and the fragment was isolated by agarose gel electrophoresis.

In the same manner as in the case of Example 2 (2) (2-2) above, a DNA fragment comprising the nucleotide sequence (the 523/612 region) corresponding to the region encoding the amino acid sequence (the 175/204 region) of SUP having the restriction SalI site at its 3' terminus and a DNA fragment comprising the nucleotide sequence (the 1696/1884 region) corresponding to the region encoding the amino acid sequence (the 566/628 region) of EIN3, each of which had been designed to have the amino acid reading frame to be in-frame with that of the other, were inserted into the aforementioned pEIN3-163/565 that had been cleaved with restriction enzymes, PstI and SalI to prepare pEIN3-163/628-SupRD.

The plasmid pEIN3-163/628-SupRD was cleaved with restriction enzymes, SmaI and SalI, and a DNA fragment encoding the amino acid sequence (the 163/628 region) of EIN3 and the 175/204 region of SUP was isolated by agarose gel electrophoresis. The isolated fragment was inserted into the pBIG2-EIN3-1/162 prepared by cleaving the pBIG2-EIN3-1/162 with a restriction enzyme SmaI, and the transformation vector pEIN3SUPRD comprising 35S-EIN3-SupRD-Nos was obtained.

(3) Transformation of Plant with pEIN3SUPRD

Arabidopsis thaliana was transformed with pEIN3SUPRD in accordance with the protocol "Transformation of Arabidopsis thaliana by vacuum infiltration (http://www.bch.msu.edu/pamgreen/protocol.htm)," except that infiltration was carried out only by immersing Arabidopsis in infiltration medium without putting it under vacuum. The plasmid pEIN3RD was introduced into soil bacteria (the Agrobacterium tumefaciens strain GV3101 (C58C1Rifr) pMP90 (Gmr) (koncz and Schell 1986)) by an electroporation. The introduced cells were cultured in a 1-liter YEP medium (Table 2 below) until the OD600 became to be 1.

TABLE 2

| YEP medium (1 liter) | |
|---|---|
| 10 g | Bactopeptone |
| 10 g | Yeast extract |
| 5 g | NaCl |

Subsequently, cells were colleted from the culture solution and then suspended in 1 liter of infiltration medium (Table 3 below).

TABLE 3

| Infiltration medium (1 liter) | |
|---|---|
| 2.29 g | MS salt |
| 50 g | Sucrose |
| 0.5 g | MES to pH 5.7 with KOH |
| 0.044 μM | Benzylaminopurine |
| 0.2 ml | Silwet L-77 |

*Arabidopsis thaliana* that had been grown for 14 days was immersed in this solution for 1 minute for infiltration, and the infiltrated *Arabidopsis thaliana* was then allowed to grow until fruition. The colleted seeds were sterilized with a 50% bleach/0.02% Triton X-100 solution for 7 minutes, rinsed three times with sterilized water, and then sowed on the sterilized selection medium containing hygromycin (Table 4 below).

TABLE 4

| Hygromycin selection medium | |
|---|---|
| 4.3 g/l | MS salt |
| 1% | Sucrose |
| 0.5 g/l | MES to pH 5.7 with KOH |
| 0.8% | Phytagar |
| 30 g/ml | Hygromycin |
| 500 ml | Vancomycin |

Transgenic plants to be grown on the aforementioned hygromycin plate were selected and then planted in soil to obtain the next-generation seeds.

(4) Inspection of Ethylene Sensitivity of Transgenic Plant

The seed of the second generation of the transgenic plants (T2) were sowed on the sterilized growth medium-containing MS plate (Table 5 below) comprising an ethylene precursor 1-aminocyclopropane-D-carboxylic acid (ACC, final concentration of 10 μM).

TABLE 5

| Selection medium-containing MS plate | |
|---|---|
| 4.3 g/l | MS salt |
| 1% | Sucrose |
| 0.5 g/l | MES to pH 5.7 with KOH |
| 0.8% | Phytagar ACC (final 10 μM) |

The aforementioned seeds were incubated at 4° C. for 3 days and then allowed to grow in a dark place at 22° C. for 3 days. In accordance with a conventional technique, the triple response, i.e., an ethylene-responsive phenotype, was observed in etiolated seedlings. The results are shown in FIG. 11 and FIG. 12.

Figure 11:
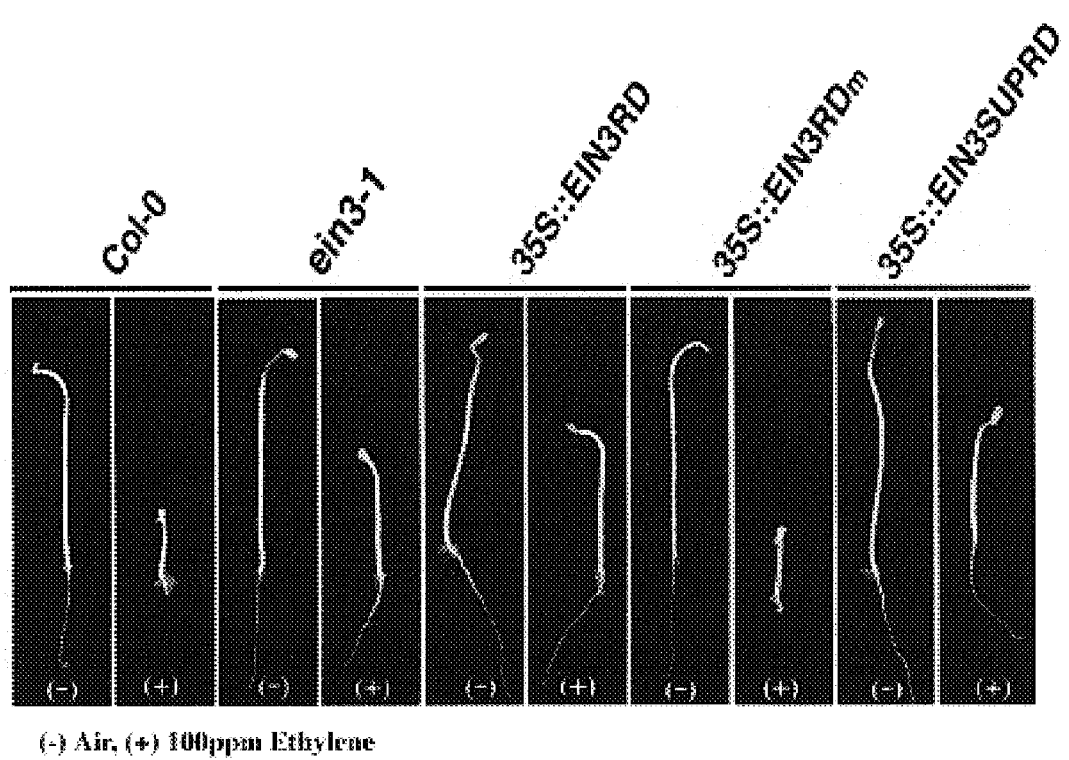
FIG. 11 is a photograph showing the effects of the SUP gene and the ERF3 gene in repressing functions of EIN3 to activate transcription, which are investigated based on the growth level of the stem and root of a plant in the presence of an ethylene.
Figure 12:
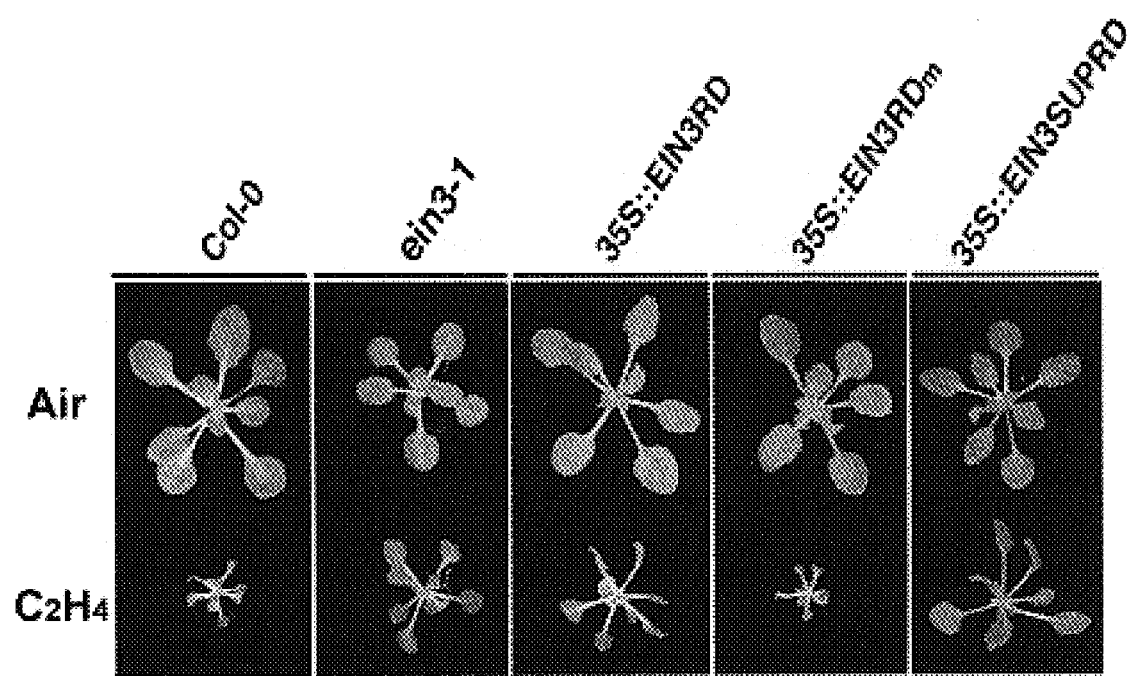
FIG. 12 is a photograph showing the effects of the SUP gene and the ERF3 gene in repressing functions of EIN3 to activate transcription, which are investigated based on the growth level of a plant in the presence of ethylene.

According to FIG. 11 and FIG. 12, wild-type Col-0 strains exhibited the triple response such as the curvature of the apical hook and an inhibition of root elongation in the presence of ACC. The plants transformed with pEIN3SUPRD (FIG. 11; 35S::EIN3SUPRD), however, exhibited no ethylene-responsive phenotype, i.e., the curvature of the apical hook or an inhibition of root elongation did not occur, as with the case of the ein3 mutant that were EIN3 mutants (FIG. 11; ein3-1). Wild-type strains that had been grown under ordinary light became dwarf plants in the constant presence of ethylene gas (100 ppm, 1 ml/min) (i.e., an ethylene-responsive phenotype). In contrast, plants transformed with pEIN3SUPRD (FIG. 12; 35S::EIN3SUPRD) became somewhat larger than the ein3 mutants (FIG. 12; ein3-1).

Expression of the PDF1.2 gene, that of the basic chitinase (BCHN) gene, and that of the ethylene responsive factor 1 (ERF1) gene, of which expression are induced by ethylene in the case of the wild-type strain but are not induced in the case of the ein3 strain, i.e., an ethylene-insensitive mutant, were investigated by Northern blot hybridization of RNAs isolated from the wild-type strains and from the plants transformed with pEIN3SUPRD.

Figure 13:
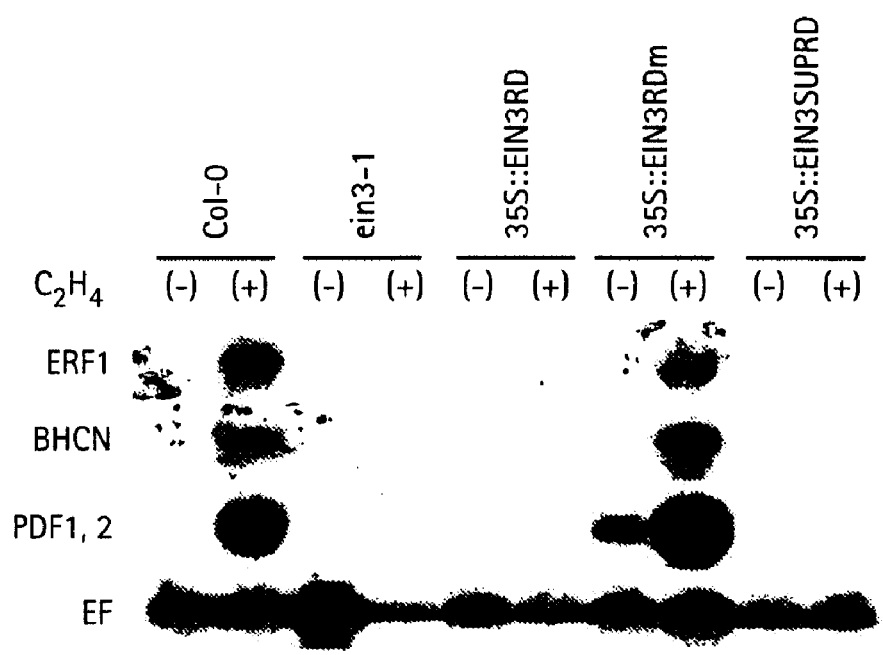
FIG. 13 is a photograph showing the effects of the SUP gene and the ERF3 gene in repressing the expression of PDF1.2, BCHN, and ERF1 genes in the presence of ethylene, which are investigated based on Northern blot hybridization using the detected mRNA representing the expression of these ethylene-inducible genes as an indicator.

As a result, expression of the PDF1.2, that of ERF1, and that of BCHN genes were induced in the wild-type strain (FIG. 13; Col-0) when treated with ethylene (100 ppm ethylene gas for 12 hours) as shown in FIG. 13. As in the case of the ein3 mutant, expression of the PDF1.2, that of ERF1, and that of BCHN genes were not induced in the plant transformed with pEIN3SUPRD (FIG. 13; 35S::EIN3SUPRD) even when they were treated with ethylene. Such transgenic plants exhibited ethylene-insensitive phenotype (in the Figure, "EF" (elongation factor) indicates the endogenous control).

As is apparent from the foregoing, a peptide having the amino acid sequence (the 175/204 region) of SUP and a gene encoding the same were capable of converting any transcription factor into a transcriptional repressor.

EXAMPLE 4

Effects of Gene Encoding the 191/225 Repression Domain of ERF3 on the Repression of the Transcription Activated by EIN3 in Plants (1) Construction of Transformation Vector pBIG2

The transformation vector pBIG2 was constructed in the same manner as in Example 3 (1).

(2) Construction of Transformation Vector pEIN3RD

PCR was carried out using the clone pEIN3 comprising the full-length cDNA of EIN3 assigned from the Salk Institute, U.S.A. as a template and using the 5'-primer 8: AATGATGTTTAATGAGATGGG (SEQ ID NO: 43) and the 3'-primer 9: ATGAATCCCCGGGATATTATTC (SEQ ID NO: 44) to amplify a DNA fragment comprising the nucleotide sequence (the 1/485 region) corresponding to the region encoding the amino acid sequence (the 1/162 region) of EIN3. The amplified fragment was cleaved with a restriction enzyme, SmaI, and the DNA fragment of interest was isolated by agarose gel electrophoresis. This fragment was inserted into pBIG2 that had been cleaved with a restriction enzyme, SmaI, and a clone that had been cloned in the forward direction was isolated to obtain pBIG2/EIN3-1/162.

The clone pEIN3 comprising the full-length cDNA of EIN3 was cleaved with restriction enzymes, SmaI and PstI, and the DNA fragment (the 487/1695 region) encoding the amino acid sequence (the 163/565 region) of EIN3 was isolated by agarose gel electrophoresis. This DNA fragment was inserted into the cloning vector pBluescriptII that had been cleaved with restriction enzymes, SmaI and PstI to prepare the plasmid pEIN3-163/565.

PCR was carried out using the clone pEIN3 comprising the full-length cDNA of EIN3 as a template and using the 5'-primer 10: CGACACTGCAGATCACAAC (SEQ ID NO: 45) and the 3'-primer 11: ATCCCGAACCATATGGATA-CATCTTGCTGC (SEQ ID NO: 46) in which the stop codon TAA at the 3-terminus had been converted to CCC to amplify a DNA fragment comprising the nucleotide sequence (the 1696/1884 region) corresponding to the region encoding the amino acid sequence (the 566/628 region) of EIN3. The amplified fragment was cleaved with a restriction enzyme, PstI and then isolated by agarose gel electrophoresis.

A DNA fragment of the nucleotide sequence (the 571/675 region) corresponding to the region encoding the amino acid sequence (the 191/225 region) of ERF3 having the restriction enzyme, SalI site at its 3' terminus was designed to have a reading frame to be in-frame with the carboxyl terminus of EIN3. The nucleotide sequence of the full-length ERF3 gene and the amino acid sequence thereof are shown in SEQ ID NOS 53 and 133, respectively.

PCR was carried out using the 5'-primer 12: AGTGGGTCCTACTGTGTCGGACTC (SEQ ID NO: 47; bound to the nucleotide sequence (the 569/593 region) of ERF3) and the 3'-primer 13: CCAAATAACATTATCG-GTCGACTCAAAATTCCATAGGTG (SEQ ID NO: 48; bound to the nucleotide sequence (the 661/678 region) of ERF3) having the restriction enzyme, SalI site to obtain a DNA fragment comprising the nucleotide sequence (the 571/675 region) corresponding to the region encoding the amino acid sequence (the 191/225 region) of ERF3. This DNA fragment was digested with a restriction enzyme, SalI, and the DNA fragment of interest was isolated by agarose gel electrophoresis.

A DNA fragment encoding the repression domain of ERF3 and a DNA fragment of the nucleotide sequence (the 1696/1884 region) encoding the amino acid sequence (the 566/628 region) of EIN3 were inserted into the aforementioned pEIN3-163/565 that had been cleaved with restriction enzymes, PstI and SalI to prepare pEIN3-163/628-RD.

The plasmid pEIN3-163/628-RD was cleaved with restriction enzymes, SmaI and SalI, and a DNA fragment encoding the amino acid sequence (the 163/628 region) of EIN3 and the 191/225 region of ERF3 was isolated by agarose gel electrophoresis. The isolated fragment was inserted into the pBIG2-EIN3-1/162 prepared by cleaving the pBIG2-EIN3-1/162 with a restriction enzyme, SmaI, and the transformation vector pEIN3RD comprising 35S-EIN3-RD-Nos was obtained.

(3) Construction of a Control Transformation Vector

In the same manner as described above, a DNA fragment encoding RDm having a mutated domain in which aspartic acids at 215 and 217 in the 191/225 repression domain of ERF3 of the sequence shown below had been substituted with alanines was inserted to obtain pEIN3RDm.

(SEQ ID NO: 49)
VGPTVSDSSSAVEENQYDGKRDIALALNLAPPMEF

The following DNA strands encoding the mutated domain including an alanine substitution were synthesized.

```
5'-AGTGGGTCCTACTGTGTCGGACTCGTCCTCTGCAGTGGAAGAGAACC           (SEQ ID NO: 50)
AATATGATGGGGAAAAGAGGAATTGATCTTGATCTTAACCTTGCTCCACCTATGGAATTTTGAG-3'

5'-TCGACTCAAAATTCCATAGGTGGAGCAAGGTTAAGATCAAGATCAAT           (SEQ ID NO: 51)
TCCTCTTTTCCCCCATCATATTGGTTCTCTTCCACTGCAGAGGACGAGTCCGACACAGTAGGACCCACT-3'
```

(4) Transformation of Plants with pEIN3RD

In the same manner as in Example 3 (3), *Arabidopsis thaliana* was transformed using the transformation vector pEIN3PRD and the control transformation vector pEIN3RDm, and selection was carried out using the hygromycin plate to obtain the next-generation seeds.

(5) Investigation of Ethylene Sensitivity of Transgenic Plant

The next-generation seeds of the transgenic plants (T2) were allowed to grow in the same manner as in Example 3 (4) to observe the triple response, i.e., an ethylene-responsive phenotype, in the etiolated seedlings. Under the same conditions, ethylene responsiveness of wild-type Col-0 strains and that of the ein3 mutants were analyzed. The results are shown in FIG. 11 and FIG. 12.

According to FIG. 11, wild-type Col-0 strains exhibited the triple response such as the curvature of the apical hook and an inhibition of root elongation in the presence of ACC. The plants transformed with pEIN3-RDm (FIG. 11; 35S::EIN3RDm) having RDm with a mutated domain in which aspartic acids at 215 and 217 in the 191/225 repression domain of ERF3 had been substituted with alanines exhibited ethylene responsiveness similar to that of the wild-type Col-0 strains. The plants transformed with pEIN3RD (FIG. 11; 35S::EIN3RD), however, exhibited ethylene insensitive phenotype. That is, neither the curvature of the apical hook or an inhibition of root elongation occurred, as with the case of the ein3 mutant (FIG. 11; ein3-1).

According to FIG. 12, wild-type strains that had been grown under ordinary light became dwarf plants (FIG. 12; Col-1) in the constant presence of ethylene gas (100 ppm for 12 hours) (i.e., an ethylene-responsive phenotype). In contrast, plants transformed with pEIN3RD (FIG. 12; 35S::EIN3RD) became substantially the same size as the ein3 mutant (FIG. 12; ein3-1).

Expression of the PDF1.2 gene, that of the basic chitinase (BCHN) gene, and that of the ethylene responsive factor 1 (ERF1) gene, which are induced by ethylene in the case of the wild-type strain but are not induced in the case of the ein3 mutant, i.e., an ethylene-insensitive mutant, were investigated by Northern blot hybridization of RNAs isolated from the wild-type strains and from the plants transformed with pEIN3RD.

As a result, expression of the PDF1.2, that of ERF1, and that of BCHN genes were induced in the wild-type strains treated with ethylene (100 ppm ethylene gas for 12 hours) as shown in FIG. 13. As with the case of the ein3 mutant, expression of the PDF1.2, that of ERF1, and that of BCHN genes were not induced in the plant transformed with pEIN3RD even when they were treated with ethylene. Such transgenic plants exhibited ethylene-insensitive phenotype.

As is apparent from the foregoing, a peptide having the amino acid sequence (the 191/225 region) of ERF3 and a gene encoding the same were capable of converting any transcription activator into a transcriptional repressor.

EXAMPLE 5

Effects of Gene Encoding the Peptide DLDLELRLGFA (SEQ ID NO: 119) (Corresponding to the 194/204 Repression Domain of SUP (SRD)) in Repressing Functions of CUC1 to Activate Transcription in Plants (1) Construction of Transformation Vector pBIG2

The transformation vector pBIG2 was constructed in the same manner as in Example 3 (1)

(2) Construction of Transformation Vector pCUC1SRD

The following complementary strands (3' complement DNA) were synthesized to prepare the amino acid sequence (VSVWPFTLDLDLELRLGFA) (SEQ ID NO: 121). In this amino acid sequence, the amino acid peptide DLDLELRLGFA (SEQ ID NO: 119) (referred to as "SRD") was bound to the carboxyl terminus of the protein-encoding region (SEQ ID NO: 54 and encoded protein SEQ ID NO: 134) of the cup-shaped cotyledon 1 (CUC1) transcription factor. Also, the reading frame of the sequence in which the stop codon had been deleted from the coding region of the CUC1 gene was designed to be in-frame with the reading frame of the coding region of SRD.

(SEQ ID NO: 55)
5'-TTAAGCGAAACCCAAACGGAGTTCTAGATCCAGATCGAGAGTAAAG
GGCCACACACTCAC-3'

Separately, the following DNA sequence corresponding to the 5' region in the protein-encoding region of the CUC1 gene was synthesized.

(SEQ ID NO:56)
5'-GGGATGGATGTTGATGTGTTTAACGG-3'

PCR was carried out using these two single-stranded DNAs as a primer and using the clone comprising the full-length cDNA of CUC1 assigned from Professor Tasaka of the Nara Institute of Science and Technology as a template to prepare the CUC1SRD gene in which the CUC1 coding region is fused with SRD. PCR conditions are as described above.

The DNA fragment of interest was isolated from the obtained DNA sample by agarose gel electrophoresis, the isolated fragment was inserted into pBIG2 that had been cleaved with a restriction enzyme, SmaI, and a clone that had been cloned in the forward direction was isolated to obtain p35S::CUC1SRD.

(3) Preparation of Plants Transformed with p35S::CUC1SRD

Arabidopsis thaliana was transformed with p35S::CUC1SRD in the same manner as in Example 3 (3).

(4) Phenotype of the Germinated Transgenic Plants

Phenotype of the resulting germinated transgenic plants (35S::CUC1SRD) are shown in FIG. 15 (right).

As a control, the cotyledon traits of the wild-type Col-0 strain and those of the cuc1/cuc2 double mutant are shown in FIG. 15 (left) and FIG. 15 (middle), respectively.

The cotyledon of the wild-type Col-0 strain was divided into two pieces, and fusion was not observed in either the base or leaf body. In the case of the cuc1/cuc2 double mutant, however, two pieces of cotyledons were fused with each other at substantially all regions at both ends, and a cup-like shape was exhibited (a cup-shaped cotyledon).

Some or most regions of the cotyledons were fused in all the germinated Arabidopsis thaliana transformed with p35S::CUC1SRD that were grown in the presence of hygromycin. This feature is very similar to that of a cuc1/cuc2 double mutant. A phenotype of partial fusion of cotyledons was substantially the same as that of the cuc1/stm-1 double mutant (Plant Cell, 9, 841, 1997; Development, 126, 1563, 1999; Development, 128, 1127, 2000). Further, formation of the apical meristem was not observed in most of these transgenic plants.

Accordingly, a peptide having the amino acid sequence DLDLELRLGFA (SEQ ID NO: 119) (corresponding to the 194/204 repression domain of SUP) and a gene encoding the same peptide were found to be capable of converting any transcription factor into a transcriptional repressor.

EXAMPLE 6

Effects of Gene Encoding the Peptide LDLELRLGFA (SEQ ID NO: 16) (Corresponding to the 195/204 Repression Domain of SUP (SRD1)) and the Peptide LDLNLAPPMEF (SEQ ID NO: 4) (Corresponding to the 215/225 Repression Domain of ERF3 (RD1)) in Repressing of the Transcription Activated by EIN3 in Plants (1) Construction of Transformation Vector pBIG2

The transformation vector pBIG2 was constructed in the same manner as in Example 3 (1).

(2) Construction of Transformation Vector pEIN3SUPRD

PCR was carried out using the clone pEIN3 comprising the full-length cDNA of EIN3 assigned from the Salk Institute, U.S.A. as a template and using the 5'-primer 8: AATGATGTTTAATGAGATGGG (SEQ ID NO: 43) and the 3'-primer 9: ATGAATCCCCGGGATATTATTC (SEQ ID NO: 44) to amplify a DNA fragment comprising the nucleotide sequence (the 1/485 region) corresponding to the region encoding the amino acid sequence (the 1/162 region) of EIN3. The amplified fragment was cleaved with a restriction enzyme, SmaI, and the DNA fragment of interest was isolated by agarose gel electrophoresis. This fragment was inserted into pBIG2 that had been cleaved with a restriction enzyme, SmaI, and a clone that had been cloned in the forward direction was isolated to obtain pBIGII/EIN3-1/162.

The clone pEIN3 comprising the full-length cDNA of EIN3 was cleaved with restriction enzymes SmaI and PstI, and the DNA fragment (the 487/1695 region) encoding the amino acid sequence (the 163/565 region) of EIN3 was isolated by agarose gel electrophoresis. This DNA fragment was inserted into the cloning vector pBluescriptII that had been cleaved with restriction enzymes, SmaI and PstI to prepare the plasmid pEIN3-163/565.

PCR was carried out using the clone pEIN3 comprising the full-length cDNA of EIN3 as a template and using the 5'-primer 10: CGACACTGCAGATCACAAC (SEQ ID NO: 45) and the 3'-primer 11: ATCCCGAACCATATGGATACATCTTGCTGC (SEQ ID NO: 46) in which the stop codon TAA at the 3-terminus had been converted to CCC to amplify a DNA fragment comprising the nucleotide sequence (the 1696/1884 region) corresponding to the region encoding the amino acid sequence (the 566/628 region) of EIN3. The amplified fragment was cleaved with a restriction enzyme, PstI and then isolated by agarose gel electrophoresis.

Two DNA strands, each of which had been designed to encode the amino acid sequence of SRD1 (LDLELRLGFA) (SEQ ID NO: 16) having the restriction site of SalI at the 3 terminus and to have the amino acid reading frame to be in-frame with that of GAl4DBD, were prepared in the same manner as in Example 2 (2)(2-2).

```
                                              (SEQ ID NO: 57)
5'-CCTGGATCTAGAACTCCGTTTGGGTTTCGCTTAA-3'

(SEQ ID NO: 58)
5'-TCGACTTAAGCGAAACCCAAACGGAGTTCTAGATCCAGG-3'
```

The above two DNA strands were annealed in the manner described in Example 2 to obtain two double-stranded DNA.

Separately, two another DNA strands, each of which had been designed to encode the amino acid sequence of RD1 (LDLNLAPPMEF) (SEQ ID NO: 4) having the restriction site of SalI at the 3' terminus and to have the amino acid reading frame to be in-frame with that of GAl 4DBD, were prepared.

```
                                              (SEQ ID NO: 59)
5'-CCTTGATCTTAACCTTGCTCCACCTATGGAATTTTGA-3'

(SEQ ID NO: 60)
5'-TCGACTCAAAATTCCATAGGTGGAGCAAGGTTAAGATCAAGG-3'
```

The above another two DNA strands were annealed in the similar manner to obtain two double-stranded DNA. Each of the obtained DNAs and a DNA fragment comprising the nucleotide sequence (the 1696/1884 region) corresponding to the region encoding the amino acid sequence of EIN3 were inserted into the aforementioned pEIN3-163/565 which had been prepared by cleaving with restriction enzymes, PstI and SalI to construct plasmids pEIN3-163/628-SRD1 and pEIN3-163/628-RD1. The plasmids pEIN3-163/628-SRD1 and pEIN3-163/628-RD1 were cleaved with restriction enzymes, SmaI and SalI, and a DNA fragment in which a region encoding SRD1 or RD1 has been fused with the amino acid sequence (the 163/628 region) of EIN3 was isolated by agarose gel electrophoresis. The isolated fragment and pBIG2-EIN3-1/162 obtained in the same manner as in Example 3 (2) were inserted into pBIG2-EIN3-1/162, which had been cleaved with a restriction enzyme, SmaI to obtain transformation vectors pEIN3SRD1 and pEIN3RD1 independently comprising CaMV35S-EIN3-SupRD-Nos.

(3) Preparation of Plants Transformed with pEIN3SRD 1 or pEIN3RD1

*Arabidopsis thaliana* was transformed with pEIN3SRD1 or pEIN3RD1 in the same manner as in Example 3 (3) to obtain the next-generation seeds.

(4) Investigation of Ethylene Sensitivity of Transgenic Plants

The triple response of etiolated seedlings was investigated in the same manner as in Example 3 (4). The results are shown in FIG. 16 and FIG. 17.

Figure 16:
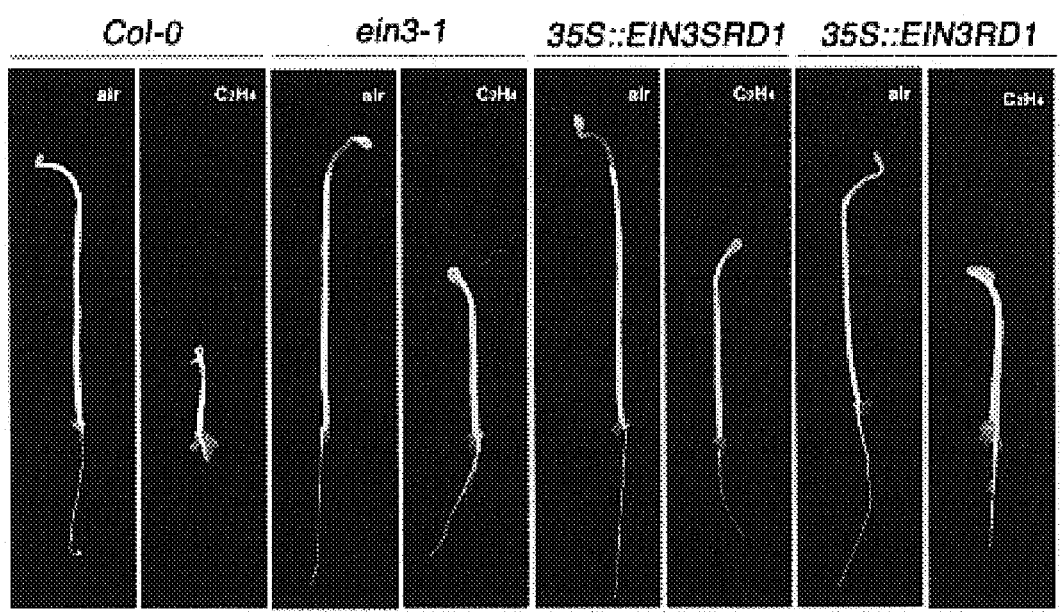
FIG. 16 is a photograph showing the conditions of the stems and roots of *Arabidopsis thaliana* transformed with pEIN3SRD1 (35S::EIN3SRD1) and *Arabidopsis thaliana* transformed with EIN3RD1 (35S::EIN3RD1) observed in the presence of ethylene.
Figure 17:
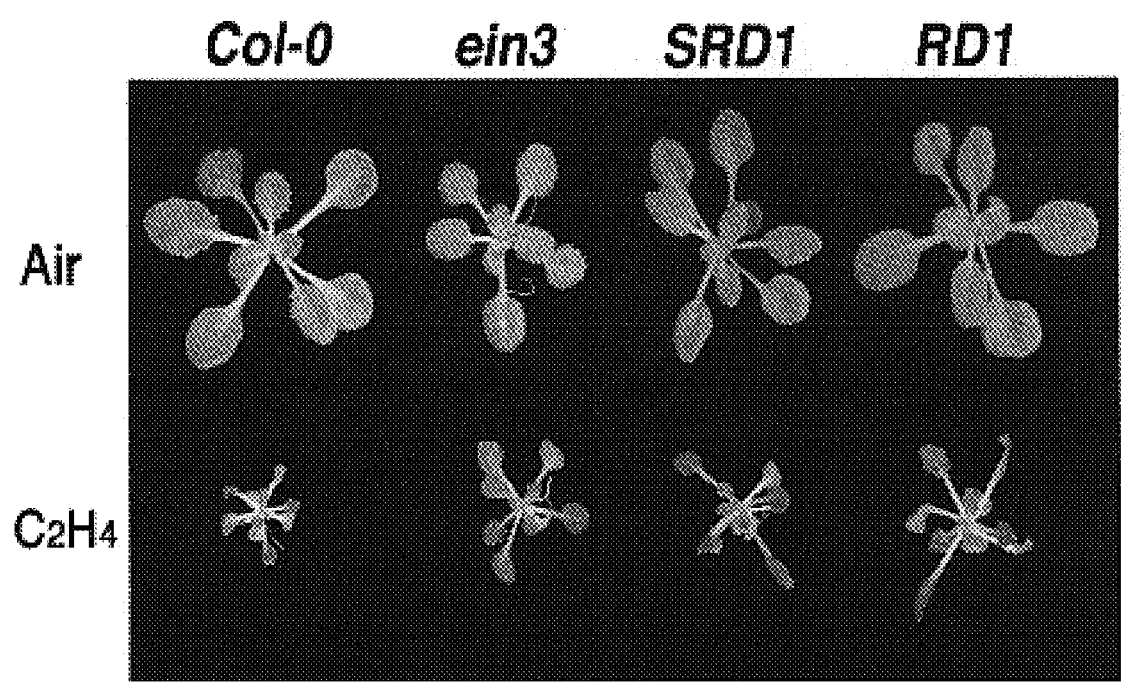
FIG. 17 is a photograph showing the growth level of *Arabidopsis thaliana* transformed with pEIN3SRD1 (35S::EIN3SRD1) and *Arabidopsis thaliana* transformed with EIN3RD1 (35S::EIN3RD1) observed in the presence of ethylene.

According to FIG. 16 and FIG. 17, wild-type Col-0 strains exhibited the triple response such as the curvature of the apical hook and an inhibition of root elongation in the presence of ACC. The plants transformed with pEIN3SRD1 or pEIN3RD1 (FIG. 16; 35S::EIN3SRD1 or 35S:: EIN3RD1), however, exhibited ethylene-insensitive phenotype. That is, neither the curvature of the apical hook or an inhibition of root elongation occurred, as with the case of the ein3 mutant (FIG. 16; ein3-1). Wild-type strains that had been grown under ordinary light became dwarf plants in the constant presence of ethylene gas (100 ppm) (i.e., an ethylene-responsive physiological phenomenon). In contrast, plants transformed with pEIN3SRD1 or pEIN3RD1 (FIG. 17; SRD1 or RD1) became the same size as the plant obtained by growing the ein3 mutant that showed ethylene-insensitive phenotype (FIG. 17; ein3) in the presence of ethylene.

As is apparent from the above results, a peptide having the amino acid sequences LDLELRLGFA (SEQ ID NO: 16) and LDLNLAPPMEF (SEQ ID NO: 4) and a gene encoding the same peptide were capable of converting any transcription factor into a transcriptional repressor.

EXAMPLE 7

Functional Conversion of the Transcription Factor Production-of-anthocyanin-pigment 1 (PAP1) in Plants Caused by the Gene Encoding a Peptide LDLDLELRLGFA (SEQ ID NO: 120) (Corresponding to the 193/204 Repression Domain of SUP (SRDX))

(1) Construction of Transformation Vector p35S:: PAP1SRDX (1-1) Isolation of PAP1 cDNA A DNA fragment comprising the PAP1 coding region but not containing the stop codon was obtained from the *Arabidopsis thaliana* cDNA library. This fragment was amplified by PCR using the following primers. The amplified fragment was separated by agarose gel electrophoresis and then recovered. PCR conditions are as described in Example 3.

```
5' Primer:
                                              (SEQ ID NO: 62)
5'-AAAATGGAGGGTTCGTCCAAAGGGCTGCGAAAAGG-3'

3' Primer:
                                              (SEQ ID NO: 63)
5'-ATCAAATTTCACAGTCTCTCCATCGAAAAGACTC-3'
```

The obtained cDNA of the PAP1 gene and the amino acid sequence encoded thereby are shown in SEQ ID NOS 66 and 135, respectively, in the Sequence Listing.

(1-2) Synthesis of Gene Encoding Peptide LDLDLELRLGFA (SRDX) (SEQ ID NO: 120)

The following DNA strands that were designed to encode a 12-amino acid peptide LDLDLELRLGFA (SRDX) (SEQ ID NO: 120) and to have the stop codon TAA at its 3' terminus were synthesized. The synthesized DNAs were annealed in the same manner as in Example 3 to prepare double-stranded DNA.

```
                                              (SEQ ID NO: 64)
5'-CTGGATCTGGATCTAGAACTCCGTTTGGGTTTCGCTTAAG-3'

(SEQ ID NO: 65)
5'-CTTAAGCGAAACCCAAACGGAGTTCTAGATCCAGATCCAG-3'
```

(1-3) Preparation of Transformation Vector

The DNA fragment consisting of the protein-encoding region of the PAP1 gene obtained above and a DNA fragment comprising the coding region of SRDX were inserted into pBIG2 that had been cleaved with a restriction enzyme, SmaI in the same manner as in Example 3. A clone that had been cloned in the forward direction was isolated to obtain the transformation vector p35S::PAP1SRDX.

(2) Preparation of Plants Transformed with Transformation Vector p35S::PAP1SRDX The next-generation seeds of *Arabidopsis thaliana* transformed with the aid of the transformation vector p35S::PAP1SRDX and the wild-type (Col-0) seeds as the control were sowed on the MS agar medium containing 3% sucrose and the MS agar medium containing no sucrose, and these seeds were allowed to grow under the same conditions as in Example 3. As a result, the wild-type seedlings accumulated reddish-purple pigments (a feature of anthocyanin) in a MS agar medium containing 3% sucrose which applies stress to the strains. In contrast, the *Arabidopsis thaliana* seedlings transformed with p35S::PAP1SRDX did not accumulate such pigments (FIG. 18A).

Figure 18:
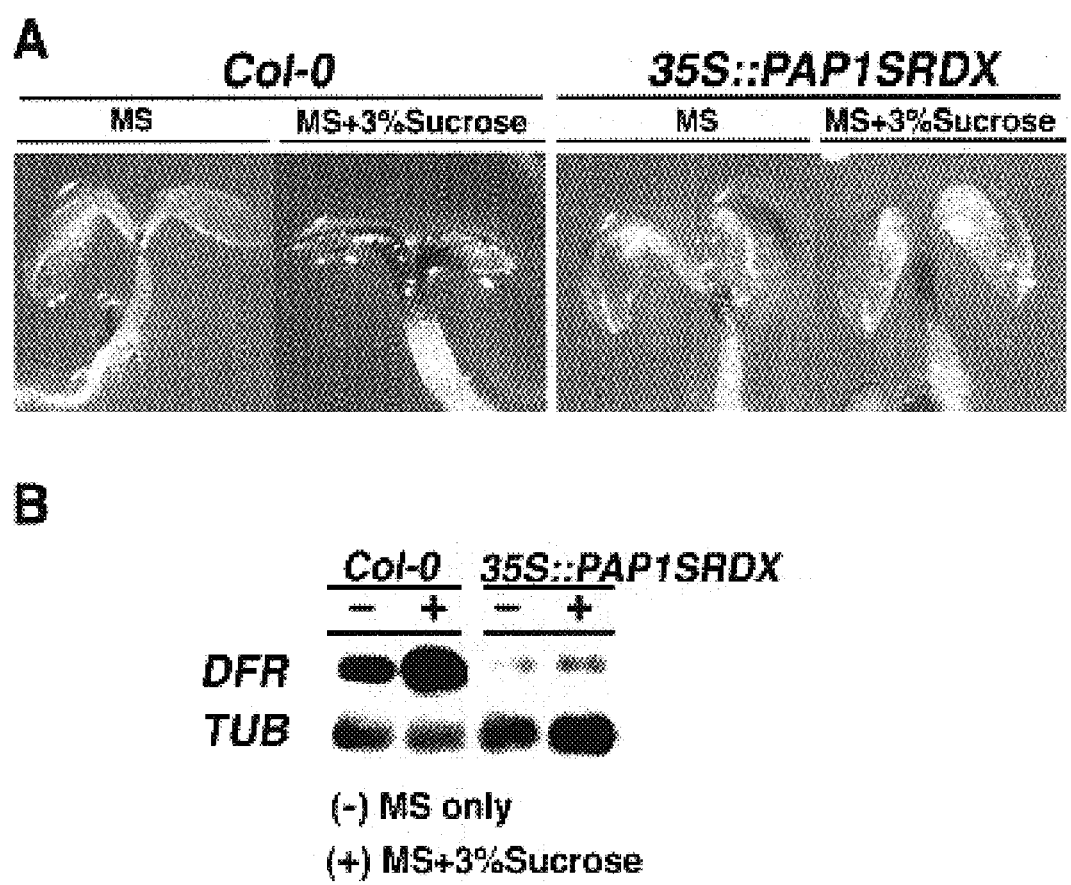
FIG. 18A is a photograph of showing the seedlings of *Arabidopsis thaliana* transformed with p35S::PAP1SRDX and wild-type *Arabidopsis thaliana* that were grown on 3% sucrose-containing MS medium.
FIG. 18B is an electrophoretogram showing the expression profile of DRF gene. in the aforementioned plant by RT-PCR.

Expression of the dihydroflavonol reductase (DFR) gene, that is involved in phenylpropanoid synthesis, i.e., an anthocyanin biosynthesis, was investigated by RT-PCR described in the Reference Example below. As a result, expression of this gene was enhanced simultaneously under stress condition in the case of wild-type strains. In contrast, such enhanced expression was not observed in the *Arabidopsis thaliana* transformed with p35S::PAP1SRDX (FIG. 18). This indicates that the PAP1 transcription factor to which the peptide SRDX had been applied was converted into a repressor, and the resulting the repressor suppresses the expression of the DFR gene in plants to inhibit anthocyanin synthesis. This also indicates that such system for repressing gene expression utilizing a repressor is applicable to the inhibition of synthesis of secondary metabolites.

EXAMPLE 8

Functional Conversion of AtMYB23 Transcription Factor in Plants by Gene Encoding Peptide LDLDLELRLGFA (SRDX) (SEQ ID NO: 120)

(1) Construction of Transformation Vector p35S::AtMYB23SRDX (1-1) Isolation of AtMYB23 cDNA A DNA fragment comprising the AtMYB23 coding region but not comprising the stop codon was obtained from the *Arabidopsis thaliana* cDNA library. This fragment was amplified by PCR using the following primers. The amplified fragment was separated by agarose gel electrophoresis and then recovered. PCR conditions are as described in Example 3.

```
5' Primer:
                                         (SEQ ID NO: 67)
5'-AAAATGAGAATGACAAGAGATGGAAAAGAACATG-3'

3' Primer:
                                         (SEQ ID NO: 68)
5'-AAGGCAATACCCATTAGTAAAATCCATCATAGTG-3'
```

The obtained cDNA of the AtMYB23 gene and the amino acid sequence encoded thereby are shown in SEQ ID NOS 69 and 136, respectively, in the Sequence Listing.

(1-2) Synthesis of Gene Encoding Peptide LDLDLELRLGFA (SRDX) (SEQ ID NO: 120)

The following DNA strands that were designed to encode a 12-amino acid peptide LDLDLELRLGFA (SRDX) (SEQ ID NO: 120) and to have the stop codon TAA at its 3' terminus were synthesized. The synthesized strands were annealed in the same manner as in Example 3 to prepare double-stranded DNA.

```
                                         (SEQ ID NO: 64)
5'-CTGGATCTGGATCTAGAACTCCGTTTGGGTTTCGCTTAAG-3'

(SEQ ID NO: 65)
5'-CTTAAGCGAAACCCAAACGGAGTTCTAGATCCAGATCCAG-3'
```

(1-3) Preparation of Transformation Vector

The DNA fragment consisting of the protein-encoding region of the AtMYB23 gene obtained above and a DNA fragment comprising the SRDX-encoding region were inserted into pBIG2 that had been cleaved with a restriction enzyme, SmaI in the same manner as in Example 3. A clone that had been cloned in the forward direction was isolated to obtain the transformation vector p35S:: AtMYB23SRDX.

Figure 19:
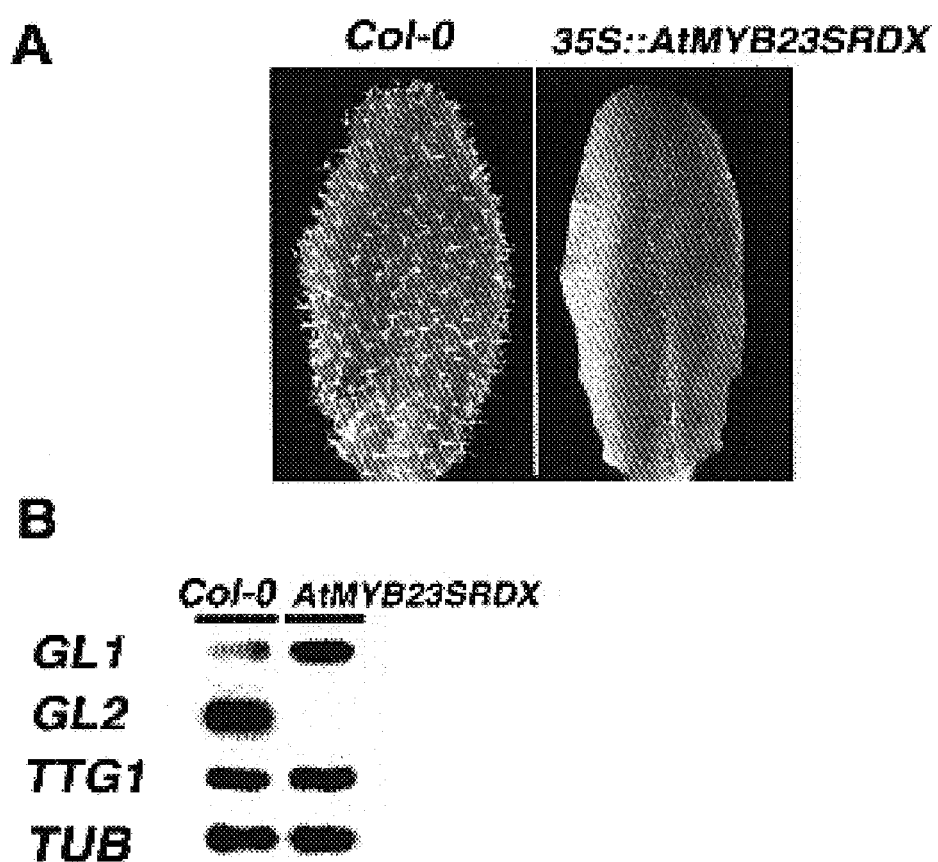
FIG. 19A is a photograph showing leaves of *Arabidopsis thaliana* transformed with p35S::AtMYB23SRDX and wild-type *Arabidopsis thaliana*.
FIG. 19B is an electrophoretogram showing the expression profile of the gene involved in the trichome development in the aforementioned plant by RT-PCR.

(2) Preparation of Plants Transformed with Transformation Vector p35S:: AtMYB23SRDX The next-generation seeds of *Arabidopsis thaliana* transformed with the aid of the transformation vector p35S::AtMYB23SRDX and the wild-type (Col-0) seeds as a control were sowed on the MS agar medium, and these seeds were allowed to grow under the same conditions as in Example 3. As a result, plants transformed with p35S::AtMYB23SRDX were found to have no trichome that was present on the epidermis of a wild-type Col-0 strain. Otherwise, the number of trichomes significantly decreased in comparison with that of the wild-type strain (FIG. 19A).

Also, expression of GLABRA1 (GL1) genes, that of GLABRA2 (GL2) genes, and that of TRANSPARENT TESTA GLABRA 1 (TTG1) genes, which were involved in the formation of trichomes, were investigated by RT-PCR described in the Reference Example below. These three types of genes were expressed similarly in the wild-type strains whereas expression of GL2 was significantly repressed in plants transformed with p35S::AtMYB23SRDX having no trichome (FIG. 19B). This indicates that the AtMYB23 transcription factor comprising a peptide SRDX added thereto is converted into a repressor, and the resultant represses the transcription of the GL2 gene in plants to suppress the formation of trichomes.

EXAMPLE 9

Transcriptional Repression Test in Tobacco Leaf and Petunia

The reporter gene CaMV35S-GAL4::LUC and the effector plasmid CaMV35S::GAL4DBD:RD (the 175/204 repression domain of SUP) were introduced using a particle gun into 1.5 cm-leaves that had been sampled in the same manner as in the case of Example 2 from the plants two weeks after the inoculation of tobacco (*Nicotiana tabacum* BY4) seeds, and allowed to stand on a water-moistened filter paper at 25° C. for 16 hours. Luciferase activity, i.e., reporter gene activity, was then assayed. As a result, the reporter gene activity was found to be inhibited by 84% when 35S-GAL4DB-RD was introduced, in comparison with the case of the control where 35S-GAL4DB and the reporter plasmid had been introduced (relative value of 100). Similarly, the aforementioned effector plasmid and the reporter plasmid were introduced using a particle gun into 1.0 cm-leaves sampled from the plants 3 weeks after the inoculation of petunia seeds, and luciferase activity was then assayed. As a result, the reporter gene activity was found to be inhibited by 82% when 35S-GAL4DB-RD was introduced, in comparison with the case of the control where 35S-GAL4DB and the reporter plasmid had been introduced (relative value of 100).

As is apparent from the above results, a chimeric gene having a repression domain was capable of repressing gene transcription in tobacco leaves and in petunia as well as in *Arabidopsis thaliana*.

REFERENCE EXAMPLE

Method of Analyzing Expression of Gene by RT-PCR

A method of analyzing expression of gene by RT-PCR employed in Examples 7 and 8 above is described below.

Total RNA was extracted from the *Arabidopsis thaliana* leaves and purified in the manner described above. Total RNA (1.65 µg or 2.5 µg) was prepared therefrom, and subjected to the DNase treatment under the following conditions in order to remove DNA that was also present.

| | |
|---|---|
| Total RNA | 1.65 µg or 2.5 µg |
| 10x DNase Buffer | 5 µl |
| DNase I | 1 µl (5 u) |
| RNase inhibitor | 0.5 µl (10 u) |
| DEPC-treated water | Balance (to bring the total amount to 50 µl) |

Reaction was allowed to incubate at 37° C. for 30 minutes, a phenol/chloroform solution was added thereto to deactivate each enzyme, and the total RNA from which DNA had been removed via ethanol precipitation was prepared.

Subsequently, the first strand of cDNA was synthesized from the total RNA using the T-Primed First-Strand Kit (Amersham). The total RNA (1.65 µg or 2.5 µg) was allowed to become suspended in 33 µl of DEPC-treated water, the suspension was incubated at 65° C. for 5 minutes, and the RNA solution was added to a tube containing the First-Strand Reaction Mix, followed by reaction at 37° C. for 60 minutes. Theoretically, the total RNA is considered to have been converted into the first strand cDNA via this reaction.

PCR was carried out using the synthesized first strand cDNA as a template and using a primer specific to the gene to be inspected. The nucleotide sequences of the primers and the composition of the PCR reaction solution used are shown below.

(Nucleotide Sequences of Primers Used in PCR)

```
β-Tubulin (TUB)
5' Primer:
5'-CGTGGATCACAGCAATACAGAGCC        (SEQ ID NO: 70)

3' Primer:
5'-CCTCCTGCACTTCCACTTCGTCTTC       (SEQ ID NO: 71)

DFR
5' Primer:
5'-AAAAAGATGACAGGATGGGT            (SEQ ID NO: 72)

3' Primer:
5'-CCCCTGTTTCTGTCTTGTTA            (SEQ ID NO: 73)

TTG1
5' Primer:
5'-GGGATGGATAATTCAGCTCCAGATTC      (SEQ ID NO: 74)

3' Primer:
```

```
-continued
5'-AACTCTAAGGAGCTGCATTTTG          (SEQ ID NO: 75)

GL1
5' Primer:
5'-GGGATGAGAATAAGGAGAAGAGATGAAAAAG (SEQ ID NO: 76)
AG

3' Primer:
5'-AAGGCAGTACTCAATATCACTAGAAGCAAAA (SEQ ID NO: 77)
TT

GL2
5' Primer:
5'-ATGGCCGTCGACATGTCTTCCAAACAACCCA (SEQ ID NO: 78)
CC

3' Primer:
5'-GCAGGGAGTTCTCGTGCCGTTCTTGAATAG  (SEQ ID NO: 79)
```

(Composition of a PCR Reaction Solution)

| | |
|---|---|
| Template cDNA | 1 µl (50 ng or 75 ng as total RNA) |
| 10 × PCR Buffer | 5 µl |
| 2.5 mM dNTP mix | 4 µl |
| 5' Primer | 0.5 µl (100 pmol/µl) |
| 3' Primer | 0.5 µl (100 pmol/µl) |
| rTaq Polymerase | 0.25 µl (1.25 u) |
| DEPC-treated water | 38.75 µl |

PCR conditions were varied from the aforementioned conditions as follows: denaturation at 95° C. for 2 minutes, 95° C. for 30 seconds, 58° C. for 30 seconds, and 72° C. for 1 minute. The number of times for repeating this cycle was changed from 25 to 35 depending on the type of gene to be inspected.

Subsequently, the RT-PCR product obtained via the aforementioned procedures was analyzed by Southern blotting and then evaluated semiquantitatively. DNA fragments in amounts of 1/100 to 1/1000 of the DNA amplified by PCR was subjected to agarose gel electrophoresis and then transferred to a nylon membrane. DNA of the corresponding gene was prepared as a probe, labeled using the ECL direct nucleic acid labeling and detection system kit (Amersham), and then subjected to hybridization and detection. The detected band represents the amount of DNA corresponding to mRNA of the gene to be inspected. Accordingly, the detected band was compared with that of the wile-type and with that of the transformed sample to inspect the expression level of each gene. In this case, the expression level of the β-tubulin (TUB) of the endogenous gene was simultaneously detected as a control.

All publications, patents, and patent applications cited herein are incorporated herein by reference in their entirety.

INDUSTRIAL APPLICABILITY

The peptide of the present invention that is capable of converting a transcription factor into a transcriptional repressor is very short. Thus, it can be very easily synthesized, and it can effectively repress transcription of genes.

When the gene of the present invention is fused with a gene encoding a DNA-binding domain of a transcription factor that binds to a specific target gene, the gene of the present invention can selectively repress the transcription of a specific gene. Such repression appears as a dominant trait, and the gene of the present invention can also repress functions of other transcription factors that are also involved in the transcription of interest. Accordingly, such gene is very useful for analyzing transcriptional functions that have not been elucidated by conventional single-gene knockout technology. It is also applicable to plants having the amphidiploid genome, such as wheat.

When the gene of the present invention is fused with, for example, DNA that binds specifically to the region for regulating the transcription of cancerous genes and is allowed to express in a cell, the gene of the present invention can effectively repress the expression of cancerous genes.

In the case of plants, for example, the gene of the present invention can create a flower having petals of different colors that could not be attained in the past. This can be realized by regulating the expression of genes encoding the pigment-metabolic enzymes. Also, the gene of the present invention enables the production of low-allergen foods by repressing the expression of allergenic proteins. Furthermore, repression of the expression of genes capable of synthesizing lignin enables the production of trees with low lignin content, thereby producing high-quality pulps. Accordingly, the present invention is applicable to and is able to provide useful technical means for a wide variety of fields.

What is claimed is:

1. A fusion protein, having activity of a transcriptional repressor, that is generated by fusing a peptide to a transcription factor, said peptide consisting of the amino acid sequence represented by:

Asp-Leu-Glu-Leu-Arg-Leu-Z3 (SEQ ID NO:137);
Leu-Asp-Leu-Glu-Leu-Arg-Leu-Z3 (SEQ ID NO:138);
Asp-Leu-Asp-Leu-Glu-Leu-Arg-Leu-Z3 (SEQ ID NO:139);
Leu-Asp-Leu-Asp-Leu-Glu-Leu-Arg-Leu-Z3 (SEQ ID NO:140);
Asp-Leu-Gln-Leu-Arg-Leu-Z3 (SEQ ID NO:141);
Leu-Asp-Leu-Gln-Leu-Arg-Leu-Z3 (SEQ ID NO:142);
Asp-Leu-Asp-Leu-Gln-Leu-Arg-Leu-Z3 (SEQ ID NO:143);
Leu-Asp-Leu-Asp-Leu-Gln-Leu-Arg-Leu-Z3 (SEQ ID NO:144);
Asp-Leu-Asp-Leu-Arg-Leu-Z3 (SEQ ID NO:145);
Leu-Asp-Leu-Asp-Leu-Arg-Leu-Z3 (SEQ ID NO:146);
Asp-Leu-Asp-Leu-Asp-Leu-Arg-Leu-Z3 (SEQ ID NO:147); or
Leu-Asp-Leu-Asp-Leu-Asp-Leu-Arg-Leu-Z3 (SEQ ID NO:148), wherein Z3 denotes 0 to 10 amino acid residues.

2. A gene encoding the fusion protein according to claim 1.

3. A recombinant vector comprising the gene according to claim 2.

4. A transformant expressing the gene according to claim 2.

5. A transformed plant expressing the gene according to claim 2.

* * * * *

SEQUENCE LISTING

```
<160> NUMBER OF SEQ ID NOS: 136

<210> SEQ ID NO 1
<211> LENGTH: 12
<212> TYPE: PRT
<213> ORGANISM: Nicotiana tabacum

<400> SEQUENCE: 1

Asp Leu Asp Leu Asn Leu Ala Pro Pro Met Glu Phe
 1               5                   10

<210> SEQ ID NO 2
<211> LENGTH: 41
<212> TYPE: DNA
<213> ORGANISM: Nicotiana tabacum

<400> SEQUENCE: 2
cgatcttgat cttaaccttg ctccacctat ggaattttga g                           41

<210> SEQ ID NO 3
<211> LENGTH: 45
<212> TYPE: DNA
<213> ORGANISM: Nicotiana tabacum

<400> SEQUENCE: 3
tcgactcaaa attccatagg tggagcaagg ttaagatcaa gatcg                       45

<210> SEQ ID NO 4
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Leu Asp Leu Asn Leu Ala Pro Pro Met Glu Phe
 1               5                   10

<210> SEQ ID NO 5
<211> LENGTH: 38
<212> TYPE: DNA
<213> ORGANISM: Artificial Sequence
<220> FEATURE:
<223> OTHER INFORMATION: Description of Artificial Sequence: Synthetic
      nucleotide sequence

<400> SEQUENCE: 5
ccttgatctt aaccttgctc cacctatgga attttgag                               38
```

<210> SEQ ID NO 6
<211> LENGTH: 42
<212> TYPE: DNA
<213> ORGANISM: Artificial Sequence
<220> FEATURE:
<223> OTHER INFORMATION: Description of Artificial Sequence: Synthetic
      nucleotide sequence

<400> SEQUENCE: 6
tcgactcaaa attccatagg tggagcaagg ttaagatcaa gg                        42

<210> SEQ ID NO 7
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Leu Asp Leu Asn Leu Ala Ala Ala Ala Ala Ala
 1               5                  10

<210> SEQ ID NO 8
<211> LENGTH: 38
<212> TYPE: DNA
<213> ORGANISM: Artificial Sequence
<220> FEATURE:
<223> OTHER INFORMATION: Description of Artificial Sequence: Synthetic
      nucleotide sequence

<400> SEQUENCE: 8
ccttgatctt aaccttgctg ctgctgctgc tgcttgag                             38

<210> SEQ ID NO 9
<211> LENGTH: 42
<212> TYPE: DNA
<213> ORGANISM: Artificial Sequence
<220> FEATURE:
<223> OTHER INFORMATION: Description of Artificial Sequence: Synthetic
      nucleotide sequence

<400> SEQUENCE: 9
tcgactcaag cagcagcagc agcagcaagg ttaagatcaa gg                        42

<210> SEQ ID NO 10
<211> LENGTH: 4
<212> TYPE: PRT
<213> ORGANISM: Arabidopsis thaliana

<400> SEQUENCE: 10

Leu Asp Leu Asn
 1

<210> SEQ ID NO 11
<211> LENGTH: 17
<212> TYPE: DNA
<213> ORGANISM: Arabidopsis thaliana

<400> SEQUENCE: 11
cctggatcta aattaag                                                   17

<210> SEQ ID NO 12
<211> LENGTH: 21
<212> TYPE: DNA
<213> ORGANISM: Arabidopsis thaliana

```
<400> SEQUENCE: 12
tcgacttaat ttagatccag g                                              21

<210> SEQ ID NO 13
<211> LENGTH: 5
<212> TYPE: PRT
<213> ORGANISM: Arabidopsis thaliana

<400> SEQUENCE: 13

Leu Asp Leu Asn Leu
 1               5

<210> SEQ ID NO 14
<211> LENGTH: 20
<212> TYPE: DNA
<213> ORGANISM: Arabidopsis thaliana

<400> SEQUENCE: 14
cctggatcta aatctgtaag                                                20

<210> SEQ ID NO 15
<211> LENGTH: 24
<212> TYPE: DNA
<213> ORGANISM: Arabidopsis thaliana

<400> SEQUENCE: 15
tcgacttaca gatttagatc cagg                                           24

<210> SEQ ID NO 16
<211> LENGTH: 10
<212> TYPE: PRT
<213> ORGANISM: Arabidopsis thaliana

<400> SEQUENCE: 16

Leu Asp Leu Glu Leu Arg Leu Gly Phe Ala
 1               5                  10

<210> SEQ ID NO 17
<211> LENGTH: 35
<212> TYPE: DNA
<213> ORGANISM: Arabidopsis thaliana

<400> SEQUENCE: 17
cctggatcta gaactccgtt tgggtttcgc ttaag                               35

<210> SEQ ID NO 18
<211> LENGTH: 39
<212> TYPE: DNA
<213> ORGANISM: Arabidopsis thaliana

<400> SEQUENCE: 18
tcgacttaag cgaaacccaa acggagttct agatccagg                           39

<210> SEQ ID NO 19
<211> LENGTH: 8
<212> TYPE: PRT
<213> ORGANISM: Arabidopsis thaliana

<400> SEQUENCE: 19

Leu Asp Leu Glu Leu Gly Phe Ala
 1               5

<210> SEQ ID NO 20
```

<211> LENGTH: 29
<212> TYPE: DNA
<213> ORGANISM: Arabidopsis thaliana

<400> SEQUENCE: 20
cctggatcta gaactcggtt tcgcttaag                                         29

<210> SEQ ID NO 21
<211> LENGTH: 33
<212> TYPE: DNA
<213> ORGANISM: Arabidopsis thaliana

<400> SEQUENCE: 21
tcgacttaag cgaaaccgag ttctagatcc agg                                    33

<210> SEQ ID NO 22
<211> LENGTH: 11
<212> TYPE: PRT
<213> ORGANISM: Arabidopsis thaliana

<400> SEQUENCE: 22

Leu Glu Leu Asp Leu Ala Ala Ala Ala Ala Ala
 1               5                  10

<210> SEQ ID NO 23
<211> LENGTH: 38
<212> TYPE: DNA
<213> ORGANISM: Arabidopsis thaliana

<400> SEQUENCE: 23
actggaacta gatctagctg cagctgcagc tgcttaag                               38

<210> SEQ ID NO 24
<211> LENGTH: 42
<212> TYPE: DNA
<213> ORGANISM: Arabidopsis thaliana

<400> SEQUENCE: 24
tcgacttaag cagctgcagc tgcagctaga tctagttcca gt                          42

<210> SEQ ID NO 25
<211> LENGTH: 65
<212> TYPE: DNA
<213> ORGANISM: Cauliflower mosaic virus

<400> SEQUENCE: 25
agcttagatc tgcaagaccc ttcctctata taaggaagtt catttcattt ggagaggaca       60
cgctg                                                                   65

<210> SEQ ID NO 26
<211> LENGTH: 65
<212> TYPE: DNA
<213> ORGANISM: Cauliflower mosaic virus

<400> SEQUENCE: 26
gatccagcgt gtcctctcca aatgaaatga acttccttat atagaggaag ggtcttgcag       60
atcta                                                                   65

<210> SEQ ID NO 27
<211> LENGTH: 24
<212> TYPE: DNA
<213> ORGANISM: Cauliflower mosaic virus -continued

<400> SEQUENCE: 27
cgccagggtt tcccagtca cgac                                              24

<210> SEQ ID NO 28
<211> LENGTH: 37
<212> TYPE: DNA
<213> ORGANISM: Cauliflower mosaic virus

<400> SEQUENCE: 28
aagggtaagc ttaaggatag tgggattgtg cgtcatc                               37

<210> SEQ ID NO 29
<211> LENGTH: 19
<212> TYPE: DNA
<213> ORGANISM: Arabidopsis thaliana

<400> SEQUENCE: 29
gatggagaga tcaaacagc                                                   19

<210> SEQ ID NO 30
<211> LENGTH: 32
<212> TYPE: DNA
<213> ORGANISM: Arabidopsis thaliana

<400> SEQUENCE: 30
gataaagtta ttaccgtcga cttaagcgaa ac                                    32

<210> SEQ ID NO 31
<211> LENGTH: 204
<212> TYPE: PRT
<213> ORGANISM: Arabidopsis thaliana

<400> SEQUENCE: 31

Met Glu Arg Ser Asn Ser Ile Glu Leu Arg Asn Ser Phe Tyr Gly Arg
 1               5                  10                  15

Ala Arg Thr Ser Pro Trp Ser Tyr Gly Asp Tyr Asp Asn Cys Gln Gln
            20                  25                  30

Asp His Asp Tyr Leu Leu Gly Phe Ser Trp Pro Pro Arg Ser Tyr Thr
        35                  40                  45

Cys Ser Phe Cys Lys Arg Glu Phe Arg Ser Ala Gln Ala Leu Gly Gly
    50                  55                  60

His Met Asn Val His Arg Arg Asp Arg Ala Arg Leu Arg Leu Gln Gln
65                  70                  75                  80

Ser Pro Ser Ser Ser Ser Thr Pro Ser Pro Pro Tyr Pro Asn Pro Asn
                85                  90                  95

Tyr Ser Tyr Ser Thr Met Ala Asn Ser Pro Pro His His Ser Pro
            100                 105                 110

Leu Thr Leu Phe Pro Thr Leu Ser Pro Pro Ser Ser Pro Arg Tyr Arg
        115                 120                 125

Ala Gly Leu Ile Arg Ser Leu Ser Pro Lys Ser Lys His Thr Pro Glu
    130                 135                 140

Asn Ala Cys Lys Thr Lys Lys Ser Ser Leu Leu Val Glu Ala Gly Glu
145                 150                 155                 160

Ala Thr Arg Phe Thr Ser Lys Asp Ala Cys Lys Ile Leu Arg Asn Asp
                165                 170                 175

Glu Ile Ile Ser Leu Glu Leu Glu Ile Gly Leu Ile Asn Glu Ser Glu
            180                 185                 190

Gln Asp Leu Asp Leu Glu Leu Arg Leu Gly Phe Ala

<210> SEQ ID NO 32
<211> LENGTH: 18
<212> TYPE: DNA
<213> ORGANISM: Arabidopsis thaliana

<400> SEQUENCE: 32
gaatgatgaa atcatcag                                               18

<210> SEQ ID NO 33
<211> LENGTH: 29
<212> TYPE: DNA
<213> ORGANISM: Arabidopsis thaliana

<400> SEQUENCE: 33
catggcgact cctaacgaag tatctgcac                                   29

<210> SEQ ID NO 34
<211> LENGTH: 39
<212> TYPE: DNA
<213> ORGANISM: Arabidopsis thaliana

<400> SEQUENCE: 34
atcgttcaaa aactcaaggc taactaatca acaacggtc                        39

<210> SEQ ID NO 35
<211> LENGTH: 65
<212> TYPE: DNA
<213> ORGANISM: Cauliflower mosaic virus

<400> SEQUENCE: 35
agcttagatc tgcaagaccc ttcctctata taaggaagtt catttcattt ggagaggaca   60
cgctg                                                             65

<210> SEQ ID NO 36
<211> LENGTH: 65
<212> TYPE: DNA
<213> ORGANISM: Cauliflower mosaic virus

<400> SEQUENCE: 36
gatccagcgt gtcctctcca aatgaaatga acttccttat atagaggaag ggtcttgcag   60
atcta                                                             65

<210> SEQ ID NO 37
<211> LENGTH: 24
<212> TYPE: DNA
<213> ORGANISM: Cauliflower mosaic virus

<400> SEQUENCE: 37
cgccagggtt ttcccagtca cgac                                        24

<210> SEQ ID NO 38
<211> LENGTH: 37
<212> TYPE: DNA
<213> ORGANISM: Cauliflower mosaic virus

<400> SEQUENCE: 38
aagggtaagc ttaaggatag tgggattgtg cgtcatc                          37

<210> SEQ ID NO 39
<211> LENGTH: 44

```
<212> TYPE: DNA
<213> ORGANISM: Artificial Sequence
<220> FEATURE:
<223> OTHER INFORMATION: Description of Artificial Sequence: Synthetic
      nucleotide sequence

<400> SEQUENCE: 39
gatcagccgc cgatcagccg ccgatcagcc gccgatcagc cgcc                       44

<210> SEQ ID NO 40
<211> LENGTH: 45
<212> TYPE: DNA
<213> ORGANISM: Artificial Sequence
<220> FEATURE:
<223> OTHER INFORMATION: Description of Artificial Sequence: Synthetic
      nucleotide sequence

<400> SEQUENCE: 40
ctagggcggc tgatcggcgg ctgatcggcg gctgatcggc cggct                      45

<210> SEQ ID NO 41
<211> LENGTH: 76
<212> TYPE: DNA
<213> ORGANISM: Artificial Sequence
<220> FEATURE:
<223> OTHER INFORMATION: Description of Artificial Sequence: Synthetic
      nucleotide sequence

<400> SEQUENCE: 41
gatccacaat taccaacaac aacaaacaac aaacaacatt acaattacag atcccggggg      60
taccgtcgac gagctc                                                     76

<210> SEQ ID NO 42
<211> LENGTH: 70
<212> TYPE: DNA
<213> ORGANISM: Artificial Sequence
<220> FEATURE:
<223> OTHER INFORMATION: Description of Artificial Sequence: Synthetic
      nucleotide sequence

<400> SEQUENCE: 42
cgtcgacggt accccgggga tctgtaattg taatgttgtt tgttgtttgt tgttgttgtt      60
ggtaattgtg                                                            70

<210> SEQ ID NO 43
<211> LENGTH: 21
<212> TYPE: DNA
<213> ORGANISM: Arabidopsis thaliana

<400> SEQUENCE: 43
aatgatgttt aatgagatgg g                                               21

<210> SEQ ID NO 44
<211> LENGTH: 22
<212> TYPE: DNA
<213> ORGANISM: Arabidopsis thaliana

<400> SEQUENCE: 44
atgaatcccc gggatattat tc                                              22

<210> SEQ ID NO 45
<211> LENGTH: 19
<212> TYPE: DNA
<213> ORGANISM: Arabidopsis thaliana
```

```
<400> SEQUENCE: 45
cgacactgca gatcacaac                                                   19

<210> SEQ ID NO 46
<211> LENGTH: 30
<212> TYPE: DNA
<213> ORGANISM: Arabidopsis thaliana

<400> SEQUENCE: 46
atcccgaacc atatggatac atcttgctgc                                       30

<210> SEQ ID NO 47
<211> LENGTH: 24
<212> TYPE: DNA
<213> ORGANISM: Nicotiana tabacum

<400> SEQUENCE: 47
agtgggtcct actgtgtcgg actc                                             24

<210> SEQ ID NO 48
<211> LENGTH: 39
<212> TYPE: DNA
<213> ORGANISM: Nicotiana tabacum

<400> SEQUENCE: 48
ccaaataaca ttatcggtcg actcaaaatt ccataggtg                             39

<210> SEQ ID NO 49
<211> LENGTH: 35
<212> TYPE: PRT
<213> ORGANISM: Nicotiana tabacum

<400> SEQUENCE: 49

Val Gly Pro Thr Val Ser Asp Ser Ser Ser Ala Val Glu Glu Asn Gln
 1               5                  10                  15

Tyr Asp Gly Lys Arg Asp Ile Ala Leu Ala Leu Asn Leu Ala Pro Pro
            20                  25                  30

Met Glu Phe
        35

<210> SEQ ID NO 50
<211> LENGTH: 111
<212> TYPE: DNA
<213> ORGANISM: Nicotiana tabacum

<400> SEQUENCE: 50
agtgggtcct actgtgtcgg actcgtcctc tgcagtggaa gagaaccaat atgatgggga      60
aaagaggaat tgatcttgat cttaaccttg ctccacctat ggaattttga g              111

<210> SEQ ID NO 51
<211> LENGTH: 116
<212> TYPE: DNA
<213> ORGANISM: Nicotiana tabacum

<400> SEQUENCE: 51
tcgactcaaa attccatagg tggagcaagg ttaagatcaa gatcaattcc tcttttcccc      60
catcatattg gttctcttcc actgcagagg acgagtccga cacagtagga cccact         116

<210> SEQ ID NO 52
<211> LENGTH: 1887
<212> TYPE: DNA
```

<213> ORGANISM: Arabidopsis thaliana
<220> FEATURE:
<221> NAME/KEY: CDS
<222> LOCATION: (1)..(1887)

<400> SEQUENCE: 52

```
atg atg ttt aat gag atg gga atg tgt gga aac atg gat ttc ttc tct        48
Met Met Phe Asn Glu Met Gly Met Cys Gly Asn Met Asp Phe Phe Ser
  1               5                  10                  15 tct gga tca ctt ggt gaa gtt gat ttc tgt cct gtt cca caa gct gag        96
Ser Gly Ser Leu Gly Glu Val Asp Phe Cys Pro Val Pro Gln Ala Glu
                 20                  25                  30 cct gat tcc att gtt gaa gat gac tat act gat gat gag att gat gtt       144
Pro Asp Ser Ile Val Glu Asp Asp Tyr Thr Asp Asp Glu Ile Asp Val
             35                  40                  45 gat gaa ttg gag agg agg atg tgg aga gac aaa atg cgg ctt aaa cgt       192
Asp Glu Leu Glu Arg Arg Met Trp Arg Asp Lys Met Arg Leu Lys Arg
         50                  55                  60 ctc aag gag cag gat aag ggt aaa gaa ggt gtt gat gct gct aaa cag       240
Leu Lys Glu Gln Asp Lys Gly Lys Glu Gly Val Asp Ala Ala Lys Gln
 65                  70                  75                  80 agg cag tct caa gag caa gct agg agg aag aaa atg tct aga gct caa       288
Arg Gln Ser Gln Glu Gln Ala Arg Arg Lys Lys Met Ser Arg Ala Gln
                 85                  90                  95 gat ggg atc ttg aag tat atg ttg aag atg atg gaa gtt tgt aaa gct       336
Asp Gly Ile Leu Lys Tyr Met Leu Lys Met Met Glu Val Cys Lys Ala
                100                 105                 110 caa ggc ttt gtt tat ggg att att ccg gag aat ggg aag cct gtg act       384
Gln Gly Phe Val Tyr Gly Ile Ile Pro Glu Asn Gly Lys Pro Val Thr
            115                 120                 125 ggt gct tct gat aat tta agg gag tgg tgg aaa gat aag gtt agg ttt       432
Gly Ala Ser Asp Asn Leu Arg Glu Trp Trp Lys Asp Lys Val Arg Phe
        130                 135                 140 gat cgt aat ggt cct gcg gct att acc aag tat caa gcg gag aat aat       480
Asp Arg Asn Gly Pro Ala Ala Ile Thr Lys Tyr Gln Ala Glu Asn Asn
145                 150                 155                 160 atc ccg ggg att cat gaa ggt aat aac ccg att gga ccg act cct cat       528
Ile Pro Gly Ile His Glu Gly Asn Asn Pro Ile Gly Pro Thr Pro His
                165                 170                 175 acc ttg caa gag ctt caa gac acg act ctt gga tcg ctt ttg tct gcg       576
Thr Leu Gln Glu Leu Gln Asp Thr Thr Leu Gly Ser Leu Leu Ser Ala
            180                 185                 190 ttg atg caa cac tgt gat cct cct cag aga cgt ttt cct ttg gag aaa       624
Leu Met Gln His Cys Asp Pro Pro Gln Arg Arg Phe Pro Leu Glu Lys
        195                 200                 205 gga gtt cct cct ccg tgg tgg cct aat ggg aaa gag gat tgg tgg cct       672
Gly Val Pro Pro Pro Trp Trp Pro Asn Gly Lys Glu Asp Trp Trp Pro
    210                 215                 220 caa ctt ggt ttg cct aaa gat caa ggt cct gca cct tac aag aag cct       720
Gln Leu Gly Leu Pro Lys Asp Gln Gly Pro Ala Pro Tyr Lys Lys Pro
225                 230                 235                 240 cat gat ttg aag aag gcg tgg aaa gtc ggc gtt ttg act gcg gtt atc       768
His Asp Leu Lys Lys Ala Trp Lys Val Gly Val Leu Thr Ala Val Ile
                245                 250                 255 aag cat atg ttt cct gat att gct aag atc cgt aag ctc gtg agg caa       816
Lys His Met Phe Pro Asp Ile Ala Lys Ile Arg Lys Leu Val Arg Gln
            260                 265                 270 tct aaa tgt ttg cag gat aag atg act gct aaa gag agt gct acc tgg       864
Ser Lys Cys Leu Gln Asp Lys Met Thr Ala Lys Glu Ser Ala Thr Trp
        275                 280                 285
```

```
ctt gct att att aac caa gaa gag tcc ttg gct aga gag ctt tat ccc    912
Leu Ala Ile Ile Asn Gln Glu Glu Ser Leu Ala Arg Glu Leu Tyr Pro
    290                 295                 300 gag tca tgt cca cct ctt tct ctg tct ggt gga agt tgc tcg ctt ctg    960
Glu Ser Cys Pro Pro Leu Ser Leu Ser Gly Gly Ser Cys Ser Leu Leu
305                 310                 315                 320 atg aat gat tgc agt caa tac gat gtt gaa ggt ttc gag aag gag tct   1008
Met Asn Asp Cys Ser Gln Tyr Asp Val Glu Gly Phe Glu Lys Glu Ser
                325                 330                 335 cac tat gaa gtg gaa gag ctc aag cca gaa aaa gtt atg aat tct tca   1056
His Tyr Glu Val Glu Glu Leu Lys Pro Glu Lys Val Met Asn Ser Ser
            340                 345                 350 aac ttt ggg atg gtt gct aaa atg cat gac ttt cct gtc aaa gaa gaa   1104
Asn Phe Gly Met Val Ala Lys Met His Asp Phe Pro Val Lys Glu Glu
        355                 360                 365 gtc cca gca gga aac tcg gaa ttc atg aga aag aga aag cca aac aga   1152
Val Pro Ala Gly Asn Ser Glu Phe Met Arg Lys Arg Lys Pro Asn Arg
370                 375                 380 gat ctg aac act att atg gac aga acc gtt ttc acc tgc gag aat ctt   1200
Asp Leu Asn Thr Ile Met Asp Arg Thr Val Phe Thr Cys Glu Asn Leu
385                 390                 395                 400 ggg tgt gcg cac agc gaa atc agc cgg gga ttt ctg gat agg aat tcg   1248
Gly Cys Ala His Ser Glu Ile Ser Arg Gly Phe Leu Asp Arg Asn Ser
                405                 410                 415 aga gac aac cat caa ctg gca tgt cca cat cga gac agt cgc tta ccg   1296
Arg Asp Asn His Gln Leu Ala Cys Pro His Arg Asp Ser Arg Leu Pro
            420                 425                 430 tat gga gca gca cca tcc agg ttt cat gtc aat gaa gtt aag cct gta   1344
Tyr Gly Ala Ala Pro Ser Arg Phe His Val Asn Glu Val Lys Pro Val
        435                 440                 445 gtt gga ttt cct cag cca agg cca gtg aac tca gta gcc caa cca att   1392
Val Gly Phe Pro Gln Pro Arg Pro Val Asn Ser Val Ala Gln Pro Ile
450                 455                 460 gac tta acg ggt ata gtt cct gaa gat gga cag aag atg atc tca gag   1440
Asp Leu Thr Gly Ile Val Pro Glu Asp Gly Gln Lys Met Ile Ser Glu
465                 470                 475                 480 ctc atg tcc atg tac gac aga aat gtc cag agc aac caa acc tct atg   1488
Leu Met Ser Met Tyr Asp Arg Asn Val Gln Ser Asn Gln Thr Ser Met
                485                 490                 495 gtc atg gaa aat caa agc gtg tca ctg ctt caa ccc aca gtc cat aac   1536
Val Met Glu Asn Gln Ser Val Ser Leu Leu Gln Pro Thr Val His Asn
            500                 505                 510 cat caa gaa cat ctc cag ttc cca gga aac atg gtg gaa gga agt ttc   1584
His Gln Glu His Leu Gln Phe Pro Gly Asn Met Val Glu Gly Ser Phe
        515                 520                 525 ttt gaa gac ttg aac atc cca aac aga gca aac aac aac aac agc agc   1632
Phe Glu Asp Leu Asn Ile Pro Asn Arg Ala Asn Asn Asn Asn Ser Ser
530                 535                 540 aac aat caa acg ttt ttt caa ggg aac aac aac aac aat gtg ttt       1680
Asn Asn Gln Thr Phe Phe Gln Gly Asn Asn Asn Asn Asn Val Phe
545                 550                 555                 560 aag ttc gac act gca gat cac aac aac ttt gaa gct gca cat aac aac   1728
Lys Phe Asp Thr Ala Asp His Asn Asn Phe Glu Ala Ala His Asn Asn
                565                 570                 575 aac aat aac agt agc ggc aac agg ttc cag ctt gtg ttt gat tcc aca   1776
Asn Asn Asn Ser Ser Gly Asn Arg Phe Gln Leu Val Phe Asp Ser Thr
            580                 585                 590 ccg ttc gac atg gcg tca ttc gat tac aga gat gat atg tcg atg cca   1824
Pro Phe Asp Met Ala Ser Phe Asp Tyr Arg Asp Asp Met Ser Met Pro
        595                 600                 605
```

-continued

```
gga gta gta gga acg atg gat gga atg cag cag aag cag caa gat gta       1872
Gly Val Val Gly Thr Met Asp Gly Met Gln Gln Lys Gln Gln Asp Val
    610                 615                 620 tcc ata tgg ttc taa                                                    1887
Ser Ile Trp Phe
625

<210> SEQ ID NO 53
<211> LENGTH: 678
<212> TYPE: DNA
<213> ORGANISM: Nicotiana tabacum
<220> FEATURE:
<221> NAME/KEY: CDS
<222> LOCATION: (1)..(678)

<400> SEQUENCE: 53 atg gct gtc aaa aat aag gtt agt aat ggc aat ctg aaa gga gga aat         48
Met Ala Val Lys Asn Lys Val Ser Asn Gly Asn Leu Lys Gly Gly Asn
1               5                   10                  15 gtg aaa aca gat gga gtt aag gag gtt cac tac aga ggt gta agg aag         96
Val Lys Thr Asp Gly Val Lys Glu Val His Tyr Arg Gly Val Arg Lys
            20                  25                  30 agg cca tgg ggt cgg tat gca gct gaa atc cgt gac ccg ggt aag aag        144
Arg Pro Trp Gly Arg Tyr Ala Ala Glu Ile Arg Asp Pro Gly Lys Lys
        35                  40                  45 agt cgg gtc tgg tta ggt act ttc gac acg gcg gaa gag gcg gct aag        192
Ser Arg Val Trp Leu Gly Thr Phe Asp Thr Ala Glu Glu Ala Ala Lys
    50                  55                  60 gcg tac gac acc gcc gct cga gag ttt cgt gga ccc aaa gca aaa act        240
Ala Tyr Asp Thr Ala Ala Arg Glu Phe Arg Gly Pro Lys Ala Lys Thr
65                  70                  75                  80 aac ttc cct tca ccg acg gag aat cag agc cca agt cac agc agc acc        288
Asn Phe Pro Ser Pro Thr Glu Asn Gln Ser Pro Ser His Ser Ser Thr
                85                  90                  95 gtg gag tcc tct agt gga gag aat ggt gtt cac gcg ccg cct cat gcg        336
Val Glu Ser Ser Ser Gly Glu Asn Gly Val His Ala Pro Pro His Ala
            100                 105                 110 ccg ctc gag ctg gat ctc acg cgc cgt ctt ggc tcc gtt gct gca gat        384
Pro Leu Glu Leu Asp Leu Thr Arg Arg Leu Gly Ser Val Ala Ala Asp
        115                 120                 125 ggc ggt gac aac tgt cgc cgt tct ggg gaa gtt ggg tac ccg att ttc        432
Gly Gly Asp Asn Cys Arg Arg Ser Gly Glu Val Gly Tyr Pro Ile Phe
    130                 135                 140 cac cag cag ccg act gtg gcg gtt ctg cca aat ggc cag ccg gtt ctg        480
His Gln Gln Pro Thr Val Ala Val Leu Pro Asn Gly Gln Pro Val Leu
145                 150                 155                 160 ctc ttt gat tct ttg tgg cgg gcg gga gtt gtt aac agg cct cag cct        528
Leu Phe Asp Ser Leu Trp Arg Ala Gly Val Val Asn Arg Pro Gln Pro
                165                 170                 175 tac cat gta acg ccg atg ggg ttt aac ggc gtt aac gcc gga gtg ggt        576
Tyr His Val Thr Pro Met Gly Phe Asn Gly Val Asn Ala Gly Val Gly
            180                 185                 190 cct act gtg tcg gac tcg tcc tct gca gtg gaa gag aac caa tat gat        624
Pro Thr Val Ser Asp Ser Ser Ser Ala Val Glu Glu Asn Gln Tyr Asp
        195                 200                 205 ggg aaa aga gga att gat ctt gat ctt aac ctt gct cca cct atg gaa        672
Gly Lys Arg Gly Ile Asp Leu Asp Leu Asn Leu Ala Pro Pro Met Glu
    210                 215                 220 ttt tga                                                                678
Phe
225
```

<210> SEQ ID NO 54
<211> LENGTH: 933
<212> TYPE: DNA
<213> ORGANISM: Arabidopsis thaliana
<220> FEATURE:
<221> NAME/KEY: CDS
<222> LOCATION: (1)..(933)

<400> SEQUENCE: 54

```
atg gat gtt gat gtg ttt aac ggt tgg ggg agg cca aga ttt gaa gat        48
Met Asp Val Asp Val Phe Asn Gly Trp Gly Arg Pro Arg Phe Glu Asp
 1               5                  10                  15 gaa tcc ctt atg cca cct ggg ttt agg ttt cat cca act gat gaa gag        96
Glu Ser Leu Met Pro Pro Gly Phe Arg Phe His Pro Thr Asp Glu Glu
             20                  25                  30 ctg atc act tac tat ctc ctc aag aag gtt ctt gac tct aat ttc tct       144
Leu Ile Thr Tyr Tyr Leu Leu Lys Lys Val Leu Asp Ser Asn Phe Ser
         35                  40                  45 tgt gcc gcc att tct caa gtt gat ctc aac aag tct gag cct tgg gag       192
Cys Ala Ala Ile Ser Gln Val Asp Leu Asn Lys Ser Glu Pro Trp Glu
     50                  55                  60 ctt cct gag aaa gcg aaa atg ggg gag aag gag tgg tac ttc ttc aca       240
Leu Pro Glu Lys Ala Lys Met Gly Glu Lys Glu Trp Tyr Phe Phe Thr
 65                  70                  75                  80 cta aga gac cgt aaa tac cca acg gga ctg aga acg aac aga gca aca       288
Leu Arg Asp Arg Lys Tyr Pro Thr Gly Leu Arg Thr Asn Arg Ala Thr
                 85                  90                  95 gaa gct ggt tac tgg aaa gcc act ggt aaa gac aga gag atc aaa agc       336
Glu Ala Gly Tyr Trp Lys Ala Thr Gly Lys Asp Arg Glu Ile Lys Ser
            100                 105                 110 tca aag aca aaa tca ctt ctc ggg atg aag aaa act ctt gtc ttt tac       384
Ser Lys Thr Lys Ser Leu Leu Gly Met Lys Lys Thr Leu Val Phe Tyr
        115                 120                 125 aaa ggc aga gct cct aaa gga gag aag agt tgt tgg gtc atg cat gag       432
Lys Gly Arg Ala Pro Lys Gly Glu Lys Ser Cys Trp Val Met His Glu
    130                 135                 140 tat cgc ctt gac ggc aaa ttc tct tac cat tac att tcc tcc tcc gct       480
Tyr Arg Leu Asp Gly Lys Phe Ser Tyr His Tyr Ile Ser Ser Ser Ala
145                 150                 155                 160 aag gat gaa tgg gtt ctc tgt aaa gtt tgt ctg aaa agc ggc gta gtt       528
Lys Asp Glu Trp Val Leu Cys Lys Val Cys Leu Lys Ser Gly Val Val
                165                 170                 175 agt aga gag acg aac ttg atc tct tct tct tct tct gcc gtc acc       576
Ser Arg Glu Thr Asn Leu Ile Ser Ser Ser Ser Ser Ala Val Thr
            180                 185                 190 gga gag ttc tcc tct gcc ggt tct gca att gct ccg atc atc aat acc       624
Gly Glu Phe Ser Ser Ala Gly Ser Ala Ile Ala Pro Ile Ile Asn Thr
        195                 200                 205 ttt gcg acg gag cac gtg tcc tgt ttc tcc aat aac tct gct gct cat       672
Phe Ala Thr Glu His Val Ser Cys Phe Ser Asn Asn Ser Ala Ala His
    210                 215                 220 acc gat gcg agc ttt cat aca ttc ctt ccc gct cca ccg cca tca ctg       720
Thr Asp Ala Ser Phe His Thr Phe Leu Pro Ala Pro Pro Pro Ser Leu
225                 230                 235                 240 ccc cca cgt cag cca cgt cac gtc ggt gat ggc gtg gcg ttt ggt cag       768
Pro Pro Arg Gln Pro Arg His Val Gly Asp Gly Val Ala Phe Gly Gln
                245                 250                 255 ttt ctg gat ttg gga tca tcg gga cag att gat ttc gat gca gca gca       816
Phe Leu Asp Leu Gly Ser Ser Gly Gln Ile Asp Phe Asp Ala Ala Ala
            260                 265                 270
```

```
gca gcg ttc ttt ccg aat cta cct tct ctg cct ccc acg gtt ctt cct      864
Ala Ala Phe Phe Pro Asn Leu Pro Ser Leu Pro Pro Thr Val Leu Pro
        275                 280                 285 cct cct ccg tca ttt gca atg tac ggt gga ggc tcc ccc gcc gtg agt      912
Pro Pro Pro Ser Phe Ala Met Tyr Gly Gly Gly Ser Pro Ala Val Ser
    290                 295                 300 gtg tgg ccg ttt act ctc tga                                          933
Val Trp Pro Phe Thr Leu
305                 310

<210> SEQ ID NO 55
<211> LENGTH: 60
<212> TYPE: DNA
<213> ORGANISM: Arabidopsis thaliana

<400> SEQUENCE: 55
ttaagcgaaa cccaaacgga gttctagatc cagatcgaga gtaaagggcc acacactcac    60

<210> SEQ ID NO 56
<211> LENGTH: 26
<212> TYPE: DNA
<213> ORGANISM: Arabidopsis thaliana

<400> SEQUENCE: 56
gggatggatg ttgatgtgtt taacgg                                         26

<210> SEQ ID NO 57
<211> LENGTH: 34
<212> TYPE: DNA
<213> ORGANISM: Arabidopsis thaliana

<400> SEQUENCE: 57
cctggatcta gaactccgtt tgggtttcgc ttaa                                34

<210> SEQ ID NO 58
<211> LENGTH: 39
<212> TYPE: DNA
<213> ORGANISM: Arabidopsis thaliana

<400> SEQUENCE: 58
tcgacttaag cgaaacccaa acggagttct agatccagg                           39

<210> SEQ ID NO 59
<211> LENGTH: 37
<212> TYPE: DNA
<213> ORGANISM: Arabidopsis thaliana

<400> SEQUENCE: 59
ccttgatctt aaccttgctc cacctatgga attttga                             37

<210> SEQ ID NO 60
<211> LENGTH: 42
<212> TYPE: DNA
<213> ORGANISM: Arabidopsis thaliana

<400> SEQUENCE: 60
tcgactcaaa attccatagg tggagcaagg ttaagatcaa gg                       42

<210> SEQ ID NO 61
<211> LENGTH: 30
<212> TYPE: PRT
<213> ORGANISM: Arabidopsis thaliana
```

<400> SEQUENCE: 61

Asn Asp Glu Ile Ile Ser Leu Glu Leu Glu Ile Gly Leu Ile Asn Glu
 1               5                  10                  15
Ser Glu Gln Asp Leu Asp Leu Glu Leu Arg Leu Gly Phe Ala
             20                  25                  30

<210> SEQ ID NO 62
<211> LENGTH: 35
<212> TYPE: DNA
<213> ORGANISM: Arabidopsis thaliana

<400> SEQUENCE: 62
aaaatggagg gttcgtccaa agggctgcga aaagg                                     35

<210> SEQ ID NO 63
<211> LENGTH: 34
<212> TYPE: DNA
<213> ORGANISM: Arabidopsis thaliana

<400> SEQUENCE: 63
atcaaatttc acagtctctc catcgaaaag actc                                      34

<210> SEQ ID NO 64
<211> LENGTH: 40
<212> TYPE: DNA
<213> ORGANISM: Arabidopsis thaliana

<400> SEQUENCE: 64
ctggatctgg atctagaact ccgtttgggt ttcgcttaag                                40

<210> SEQ ID NO 65
<211> LENGTH: 40
<212> TYPE: DNA
<213> ORGANISM: Arabidopsis thaliana

<400> SEQUENCE: 65
cttaagcgaa acccaaacgg agttctagat ccagatccag                                40

<210> SEQ ID NO 66
<211> LENGTH: 747
<212> TYPE: DNA
<213> ORGANISM: Arabidopsis thaliana
<220> FEATURE:
<221> NAME/KEY: CDS
<222> LOCATION: (1)..(747)

<400> SEQUENCE: 66 atg gag ggt tcg tcc aaa ggg ctg cga aaa ggt gct tgg act act gaa          48
Met Glu Gly Ser Ser Lys Gly Leu Arg Lys Gly Ala Trp Thr Thr Glu
 1               5                  10                  15 gaa gat agt ctc ttg aga cag tgc att aat aag tat gga gaa ggc aaa          96
Glu Asp Ser Leu Leu Arg Gln Cys Ile Asn Lys Tyr Gly Glu Gly Lys
             20                  25                  30 tgg cac caa gtt cct gta aga gct ggg cta aac cgg tgc agg aaa agt         144
Trp His Gln Val Pro Val Arg Ala Gly Leu Asn Arg Cys Arg Lys Ser
         35                  40                  45 tgt aga tta aga tgg ttg aac tat ttg aag cca agt atc aag aga gga         192
Cys Arg Leu Arg Trp Leu Asn Tyr Leu Lys Pro Ser Ile Lys Arg Gly
     50                  55                  60 aaa ctt agc tct gat gaa gtc gat ctt ctt ctt cgc ctt cat agg ctt         240
Lys Leu Ser Ser Asp Glu Val Asp Leu Leu Leu Arg Leu His Arg Leu
 65                  70                  75                  80

```
cta ggg aat agg tgg tct tta att gct gga aga tta cct ggt cgg acc      288
Leu Gly Asn Arg Trp Ser Leu Ile Ala Gly Arg Leu Pro Gly Arg Thr
                 85                  90                  95 gca aat gac gtc aag aat tac tgg aac act cat ctg agt aag aaa cat      336
Ala Asn Asp Val Lys Asn Tyr Trp Asn Thr His Leu Ser Lys Lys His
            100                 105                 110 gaa ccg tgt tgt aag ata aag atg aaa aag aga gac att acg ccc att      384
Glu Pro Cys Cys Lys Ile Lys Met Lys Lys Arg Asp Ile Thr Pro Ile
        115                 120                 125 cct aca aca ccg gca cta aaa aac aat gtt tat aag cct cga cct cga      432
Pro Thr Thr Pro Ala Leu Lys Asn Asn Val Tyr Lys Pro Arg Pro Arg
    130                 135                 140 tcc ttc aca gtt aac aac gac tgc aac cat ctc aat gcc cca cca aaa      480
Ser Phe Thr Val Asn Asn Asp Cys Asn His Leu Asn Ala Pro Pro Lys
145                 150                 155                 160 gtt gac gtt aat cct cca tgc ctt gga ctt aac atc aat aat gtt tgt      528
Val Asp Val Asn Pro Pro Cys Leu Gly Leu Asn Ile Asn Asn Val Cys
                165                 170                 175 gac aat agt atc ata tac aac aaa gat aag aag aaa gac caa cta gtg      576
Asp Asn Ser Ile Ile Tyr Asn Lys Asp Lys Lys Lys Asp Gln Leu Val
            180                 185                 190 aat aat ttg att gat gga gat aat atg tgg tta gag aaa ttc cta gag      624
Asn Asn Leu Ile Asp Gly Asp Asn Met Trp Leu Glu Lys Phe Leu Glu
        195                 200                 205 gaa agc caa gag gta gat att ttg gtt cct gaa gcg acg aca aca gaa      672
Glu Ser Gln Glu Val Asp Ile Leu Val Pro Glu Ala Thr Thr Thr Glu
    210                 215                 220 aag ggg gac acc ttg gct ttt gac gtt gat caa ctt tgg agt ctt ttc      720
Lys Gly Asp Thr Leu Ala Phe Asp Val Asp Gln Leu Trp Ser Leu Phe
225                 230                 235                 240 gat gga gag act gtg aaa ttt gat tag                                  747
Asp Gly Glu Thr Val Lys Phe Asp
                245

<210> SEQ ID NO 67
<211> LENGTH: 34
<212> TYPE: DNA
<213> ORGANISM: Arabidopsis thaliana

<400> SEQUENCE: 67
aaaatgagaa tgacaagaga tggaaaagaa catg                                34

<210> SEQ ID NO 68
<211> LENGTH: 34
<212> TYPE: DNA
<213> ORGANISM: Arabidopsis thaliana

<400> SEQUENCE: 68
aaggcaatac ccattagtaa aatccatcat agtg                                34

<210> SEQ ID NO 69
<211> LENGTH: 660
<212> TYPE: DNA
<213> ORGANISM: Arabidopsis thaliana
<220> FEATURE:
<221> NAME/KEY: CDS
<222> LOCATION: (1)..(660)

<400> SEQUENCE: 69 atg aga atg aca aga gat gga aaa gaa cat gaa tac aag aaa ggt tta       48
Met Arg Met Thr Arg Asp Gly Lys Glu His Glu Tyr Lys Lys Gly Leu
  1               5                  10                  15
```

| | | |
|---|---|---|
| tgg aca gtt gaa gaa gac aag atc ctc atg gat tat gtc cga act cat<br>Trp Thr Val Glu Glu Asp Lys Ile Leu Met Asp Tyr Val Arg Thr His<br>20              25                  30 | | 96 |
| ggc cag ggc cac tgg aac cgc atc gcc aag aaa act ggg ctc aag aga<br>Gly Gln Gly His Trp Asn Arg Ile Ala Lys Lys Thr Gly Leu Lys Arg<br>    35                  40                  45 | | 144 |
| tgt ggg aaa agc tgt agg ttg aga tgg atg aac tac tta agc cct aat<br>Cys Gly Lys Ser Cys Arg Leu Arg Trp Met Asn Tyr Leu Ser Pro Asn<br>50                  55                  60 | | 192 |
| gtt aac aga ggc aat ttt act gac caa gaa gaa gat ctc atc atc aga<br>Val Asn Arg Gly Asn Phe Thr Asp Gln Glu Glu Asp Leu Ile Ile Arg<br>65                  70                  75                  80 | | 240 |
| ctc cac aag ctc ctc ggc aac aga tgg tcg ttg ata gcg aaa aga gtt<br>Leu His Lys Leu Leu Gly Asn Arg Trp Ser Leu Ile Ala Lys Arg Val<br>                85                  90                  95 | | 288 |
| ccg gga aga aca gac aac caa gta aag aat tac tgg aac aca cat ctc<br>Pro Gly Arg Thr Asp Asn Gln Val Lys Asn Tyr Trp Asn Thr His Leu<br>            100                 105                 110 | | 336 |
| agc aag aaa ctt ggt ctc gga gat cat tca act gcc gtc aaa gcc gca<br>Ser Lys Lys Leu Gly Leu Gly Asp His Ser Thr Ala Val Lys Ala Ala<br>        115                 120                 125 | | 384 |
| tgc ggt gta gag tct cca ccg tct atg gcc ctt ata acc aca acg tcc<br>Cys Gly Val Glu Ser Pro Pro Ser Met Ala Leu Ile Thr Thr Thr Ser<br>    130                 135                 140 | | 432 |
| tcc tct cat caa gag atc tcc ggt gga aaa aat tca act cta agg ttc<br>Ser Ser His Gln Glu Ile Ser Gly Gly Lys Asn Ser Thr Leu Arg Phe<br>145                 150                 155                 160 | | 480 |
| gac act tta gtt gac gaa tcc aaa ctc aaa cca aaa tcc aaa cta gtc<br>Asp Thr Leu Val Asp Glu Ser Lys Leu Lys Pro Lys Ser Lys Leu Val<br>                165                 170                 175 | | 528 |
| cac gca aca cca act gac gta gaa gtt gca gct acg gtt cca aat ctg<br>His Ala Thr Pro Thr Asp Val Glu Val Ala Ala Thr Val Pro Asn Leu<br>            180                 185                 190 | | 576 |
| ttc gat acc ttt tgg gtt ctt gaa gac gac ttc gag ctt agt tca ctc<br>Phe Asp Thr Phe Trp Val Leu Glu Asp Asp Phe Glu Leu Ser Ser Leu<br>        195                 200                 205 | | 624 |
| act atg atg gat ttt act aat ggg tat tgc ctt tga<br>Thr Met Met Asp Phe Thr Asn Gly Tyr Cys Leu<br>    210                 215 | | 660 |

<210> SEQ ID NO 70
<211> LENGTH: 24
<212> TYPE: DNA
<213> ORGANISM: Arabidopsis thaliana

<400> SEQUENCE: 70
cgtggatcac agcaatacag agcc                                              24

<210> SEQ ID NO 71
<211> LENGTH: 25
<212> TYPE: DNA
<213> ORGANISM: Arabidopsis thaliana

<400> SEQUENCE: 71
cctcctgcac ttccacttcg tcttc                                             25

<210> SEQ ID NO 72
<211> LENGTH: 20
<212> TYPE: DNA
<213> ORGANISM: Arabidopsis thaliana

<400> SEQUENCE: 72

```
aaaaagatga caggatgggt                                              20

<210> SEQ ID NO 73
<211> LENGTH: 20
<212> TYPE: DNA
<213> ORGANISM: Arabidopsis thaliana

<400> SEQUENCE: 73
cccctgtttc tgtcttgtta                                              20

<210> SEQ ID NO 74
<211> LENGTH: 26
<212> TYPE: DNA
<213> ORGANISM: Arabidopsis thaliana

<400> SEQUENCE: 74
gggatggata attcagctcc agattc                                       26

<210> SEQ ID NO 75
<211> LENGTH: 22
<212> TYPE: DNA
<213> ORGANISM: Arabidopsis thaliana

<400> SEQUENCE: 75
aactctaagg agctgcattt tg                                           22

<210> SEQ ID NO 76
<211> LENGTH: 33
<212> TYPE: DNA
<213> ORGANISM: Arabidopsis thaliana

<400> SEQUENCE: 76
gggatgagaa taaggagaag agatgaaaaa gag                               33

<210> SEQ ID NO 77
<211> LENGTH: 33
<212> TYPE: DNA
<213> ORGANISM: Arabidopsis thaliana

<400> SEQUENCE: 77
aaggcagtac tcaatatcac tagaagcaaa att                               33

<210> SEQ ID NO 78
<211> LENGTH: 33
<212> TYPE: DNA
<213> ORGANISM: Arabidopsis thaliana

<400> SEQUENCE: 78
atggccgtcg acatgtcttc caaacaaccc acc                               33

<210> SEQ ID NO 79
<211> LENGTH: 30
<212> TYPE: DNA
<213> ORGANISM: Arabidopsis thaliana

<400> SEQUENCE: 79
gcagggagtt ctcgtgccgt tcttgaatag                                   30

<210> SEQ ID NO 80
<211> LENGTH: 11
<212> TYPE: PRT
<213> ORGANISM: Artificial Sequence
<220> FEATURE:
```

<223> OTHER INFORMATION: Description of Artificial Sequence: Synthetic
      peptide

<400> SEQUENCE: 80

Leu Glu Leu Arg Leu Ala Ala Ala Ala Ala
 1               5                  10

<210> SEQ ID NO 81
<211> LENGTH: 41
<212> TYPE: DNA
<213> ORGANISM: Artificial Sequence
<220> FEATURE:
<223> OTHER INFORMATION: Description of Artificial Sequence: Synthetic
      nucleotide sequence

<400> SEQUENCE: 81
actagaactc cgtttggctg ccgcagcggc tgcataatga g                    41

<210> SEQ ID NO 82
<211> LENGTH: 45
<212> TYPE: DNA
<213> ORGANISM: Artificial Sequence
<220> FEATURE:
<223> OTHER INFORMATION: Description of Artificial Sequence: Synthetic
      nucleotide sequence

<400> SEQUENCE: 82
tcgactcatt atgcagccgc tgcggcagcc aaacggagtt ctagt                45

<210> SEQ ID NO 83
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Asp Leu Glu Leu Arg Leu
 1               5

<210> SEQ ID NO 84
<211> LENGTH: 26
<212> TYPE: DNA
<213> ORGANISM: Artificial Sequence
<220> FEATURE:
<223> OTHER INFORMATION: Description of Artificial Sequence: Synthetic
      nucleotide sequence

<400> SEQUENCE: 84
agatctagaa ctccgtttgt aatgag                                     26

<210> SEQ ID NO 85
<211> LENGTH: 30
<212> TYPE: DNA
<213> ORGANISM: Artificial Sequence
<220> FEATURE:
<223> OTHER INFORMATION: Description of Artificial Sequence: Synthetic
      nucleotide sequence

<400> SEQUENCE: 85
tcgactcatt acaaacggag ttctagatct                                 30

<210> SEQ ID NO 86
<211> LENGTH: 10
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 86

Leu Asp Leu Gln Leu Arg Leu Gly Tyr Tyr
  1               5                  10

<210> SEQ ID NO 87
<211> LENGTH: 38
<212> TYPE: DNA
<213> ORGANISM: Artificial Sequence
<220> FEATURE:
<223> OTHER INFORMATION: Description of Artificial Sequence: Synthetic
      nucleotide sequence

<400> SEQUENCE: 87
actggatcta caactccgtt tgggttatta ctaatgag                           38

<210> SEQ ID NO 88
<211> LENGTH: 41
<212> TYPE: DNA
<213> ORGANISM: Artificial Sequence
<220> FEATURE:
<223> OTHER INFORMATION: Description of Artificial Sequence: Synthetic
      nucleotide sequence

<400> SEQUENCE: 88
tcgactcatt agtaataacc caaacggagt tgtagatcca g                      41

<210> SEQ ID NO 89
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Leu Asp Leu Glu Leu Arg Leu
  1               5

<210> SEQ ID NO 90
<211> LENGTH: 29
<212> TYPE: DNA
<213> ORGANISM: Artificial Sequence
<220> FEATURE:
<223> OTHER INFORMATION: Description of Artificial Sequence: Synthetic
      nucleotide sequence

<400> SEQUENCE: 90
actggatcta gaactccgtt tgtaatgag                                    29

<210> SEQ ID NO 91
<211> LENGTH: 33
<212> TYPE: DNA
<213> ORGANISM: Artificial Sequence
<220> FEATURE:
<223> OTHER INFORMATION: Description of Artificial Sequence: Synthetic
      nucleotide sequence

<400> SEQUENCE: 91
tcgactcatt acaaacggag ttctagatcc agt                               33

<210> SEQ ID NO 92
<211> LENGTH: 11
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 92

Leu Asp Leu Glu Leu Ala Ala Ala Ala Ala
  1               5                  10

<210> SEQ ID NO 93
<211> LENGTH: 41
<212> TYPE: DNA
<213> ORGANISM: Artificial Sequence
<220> FEATURE:
<223> OTHER INFORMATION: Description of Artificial Sequence: Synthetic
      nucleotide sequence

<400> SEQUENCE: 93
actggatcta gaactcgctg ccgcagcggc tgcataatga g                   41

<210> SEQ ID NO 94
<211> LENGTH: 45
<212> TYPE: DNA
<213> ORGANISM: Artificial Sequence
<220> FEATURE:
<223> OTHER INFORMATION: Description of Artificial Sequence: Synthetic
      nucleotide sequence

<400> SEQUENCE: 94
tcgactcatt atgcagccgc tgcggcagcg agttctagat ccagt              45

<210> SEQ ID NO 95
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Leu Asp Leu Glu Leu Arg Leu Ala Ala Ala
  1               5                  10

<210> SEQ ID NO 96
<211> LENGTH: 38
<212> TYPE: DNA
<213> ORGANISM: Artificial Sequence
<220> FEATURE:
<223> OTHER INFORMATION: Description of Artificial Sequence: Synthetic
      nucleotide sequence

<400> SEQUENCE: 96
actggatcta gaactccgtt tggctgccgc ataatgag                      38

<210> SEQ ID NO 97
<211> LENGTH: 42
<212> TYPE: DNA
<213> ORGANISM: Artificial Sequence
<220> FEATURE:
<223> OTHER INFORMATION: Description of Artificial Sequence: Synthetic
      nucleotide sequence

<400> SEQUENCE: 97
tcgactcatt atgcggcagc caaacggagt tctagatcca gt                 42

<210> SEQ ID NO 98
<211> LENGTH: 11
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

Leu Glu Leu Asp Leu Ala Ala Ala Ala Ala
 1               5                  10

<210> SEQ ID NO 99
<211> LENGTH: 38
<212> TYPE: DNA
<213> ORGANISM: Artificial Sequence
<220> FEATURE:
<223> OTHER INFORMATION: Description of Artificial Sequence: Synthetic
      nucleotide sequence

<400> SEQUENCE: 99
ccttgagctt gatcttgctg ctgctgctgc tgcttgag                            38

<210> SEQ ID NO 100
<211> LENGTH: 42
<212> TYPE: DNA
<213> ORGANISM: Artificial Sequence
<220> FEATURE:
<223> OTHER INFORMATION: Description of Artificial Sequence: Synthetic
      nucleotide sequence

<400> SEQUENCE: 100
tcgactcaag cagcagcagc agcagcaaga tcaagctcaa gg                       42

<210> SEQ ID NO 101
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

Leu Asp Leu Glu Leu Arg Leu Gly
 1               5

<210> SEQ ID NO 102
<211> LENGTH: 26
<212> TYPE: DNA
<213> ORGANISM: Artificial Sequence
<220> FEATURE:
<223> OTHER INFORMATION: Description of Artificial Sequence: Synthetic
      nucleotide sequence

<400> SEQUENCE: 102
cctggatcta gaactccgtg gttaag                                         26

<210> SEQ ID NO 103
<211> LENGTH: 30
<212> TYPE: DNA
<213> ORGANISM: Artificial Sequence
<220> FEATURE:
<223> OTHER INFORMATION: Description of Artificial Sequence: Synthetic
      nucleotide sequence

<400> SEQUENCE: 103
tcgacttaac cacggagttc tagatccagg                                     30

<210> SEQ ID NO 104
```

```
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 104

Leu Glu Leu Arg Leu
 1               5

<210> SEQ ID NO 105
<211> LENGTH: 23
<212> TYPE: DNA
<213> ORGANISM: Artificial Sequence
<220> FEATURE:
<223> OTHER INFORMATION: Description of Artificial Sequence: Synthetic
      nucleotide sequence

<400> SEQUENCE: 105
tctagaactc cgtttgtaat gag                                           23

<210> SEQ ID NO 106
<211> LENGTH: 27
<212> TYPE: DNA
<213> ORGANISM: Artificial Sequence
<220> FEATURE:
<223> OTHER INFORMATION: Description of Artificial Sequence: Synthetic
      nucleotide sequence

<400> SEQUENCE: 106
tcgactcatt acaaacggag ttctaga                                       27

<210> SEQ ID NO 107
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107

Phe Asp Leu Asn Phe Ala Pro Leu Asp Cys Val
 1               5                  10

<210> SEQ ID NO 108
<211> LENGTH: 38
<212> TYPE: DNA
<213> ORGANISM: Artificial Sequence
<220> FEATURE:
<223> OTHER INFORMATION: Description of Artificial Sequence: Synthetic
      nucleotide sequence

<400> SEQUENCE: 108
attcgatctt aattttgcac cgttggattg tgtttaag                           38

<210> SEQ ID NO 109
<211> LENGTH: 45
<212> TYPE: DNA
<213> ORGANISM: Artificial Sequence
<220> FEATURE:
<223> OTHER INFORMATION: Description of Artificial Sequence: Synthetic
      nucleotide sequence

<400> SEQUENCE: 109
tcgactcatt aaacacaatc caacggtgca aaattaagat cgaat                   45
```

<210> SEQ ID NO 110
<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 110

Phe Asp Leu Asn Ile Phe Pro Pro Ile Pro Glu Phe
 1               5                  10

<210> SEQ ID NO 111
<211> LENGTH: 38
<212> TYPE: DNA
<213> ORGANISM: Artificial Sequence
<220> FEATURE:
<223> OTHER INFORMATION: Description of Artificial Sequence: Synthetic
nucleotide sequence

<400> SEQUENCE: 111
gtttgacctc aacatccctc cgatccctga attctaag                              38

<210> SEQ ID NO 112
<211> LENGTH: 42
<212> TYPE: DNA
<213> ORGANISM: Artificial Sequence
<220> FEATURE:
<223> OTHER INFORMATION: Description of Artificial Sequence: Synthetic
nucleotide sequence

<400> SEQUENCE: 112
tcgacttaga attcagggat cggagggatg ttgaggtcaa ac                         42

<210> SEQ ID NO 113
<211> LENGTH: 13
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 113

Phe Gln Phe Asp Leu Asn Phe Pro Pro Leu Asp Cys Val
 1               5                  10

<210> SEQ ID NO 114
<211> LENGTH: 44
<212> TYPE: DNA
<213> ORGANISM: Artificial Sequence
<220> FEATURE:
<223> OTHER INFORMATION: Description of Artificial Sequence: Synthetic
nucleotide sequence

<400> SEQUENCE: 114
ctttcaattc gatcttaatt ttccaccgtt ggattgtgtt taag                       44

<210> SEQ ID NO 115
<211> LENGTH: 48
<212> TYPE: DNA
<213> ORGANISM: Artificial Sequence
<220> FEATURE:
<223> OTHER INFORMATION: Description of Artificial Sequence: Synthetic
nucleotide sequence

<400> SEQUENCE: 115
tcgacttaaa cacaatccaa cggtggaaaa ttaagatcga attgaaag                   48

```
<210> SEQ ID NO 116
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 116

Asp Leu Asp Leu Arg Leu
 1               5

<210> SEQ ID NO 117
<211> LENGTH: 29
<212> TYPE: DNA
<213> ORGANISM: Artificial Sequence
<220> FEATURE:
<223> OTHER INFORMATION: Description of Artificial Sequence: Synthetic
      nucleotide sequence

<400> SEQUENCE: 117
actggatcta gatctccgtt tgtaatgag                                    29

<210> SEQ ID NO 118
<211> LENGTH: 33
<212> TYPE: DNA
<213> ORGANISM: Artificial Sequence
<220> FEATURE:
<223> OTHER INFORMATION: Description of Artificial Sequence: Synthetic
      nucleotide sequence

<400> SEQUENCE: 118
tcgactcatt acaaacggag atctagatcc agt                               33

<210> SEQ ID NO 119
<211> LENGTH: 11
<212> TYPE: PRT
<213> ORGANISM: Arabidopsis thaliana

<400> SEQUENCE: 119

Asp Leu Asp Leu Glu Leu Arg Leu Gly Phe Ala
 1               5                  10

<210> SEQ ID NO 120
<211> LENGTH: 12
<212> TYPE: PRT
<213> ORGANISM: Arabidopsis thaliana

<400> SEQUENCE: 120

Leu Asp Leu Asp Leu Glu Leu Arg Leu Gly Phe Ala
 1               5                  10

<210> SEQ ID NO 121
<211> LENGTH: 19
<212> TYPE: PRT
<213> ORGANISM: Arabidopsis thaliana

<400> SEQUENCE: 121

Val Ser Val Trp Pro Phe Thr Leu Asp Leu Asp Leu Glu Leu Arg Leu
 1               5                  10                  15

Gly Phe Ala

<210> SEQ ID NO 122
<211> LENGTH: 7
<212> TYPE: PRT
```

```
<213> ORGANISM: Artificial Sequence
<220> FEATURE:
<223> OTHER INFORMATION: Description of Artificial Sequence: Synthetic
      peptide motif
<220> FEATURE:
<221> NAME/KEY: MOD_RES
<222> LOCATION: (1)
<223> OTHER INFORMATION: Leu or Phe
<220> FEATURE:
<221> NAME/KEY: MOD_RES
<222> LOCATION: (5)
<223> OTHER INFORMATION: Leu or Phe
<220> FEATURE:
<221> NAME/KEY: MOD_RES
<222> LOCATION: (6)
<223> OTHER INFORMATION: Any amino acid

<400> SEQUENCE: 122

Xaa Asp Leu Asn Xaa Xaa Pro
 1               5

<210> SEQ ID NO 123
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(10)
<223> OTHER INFORMATION: This region may encompass 0-10 variable amino
      acids
<220> FEATURE:
<221> NAME/KEY: MOD_RES
<222> LOCATION: (14)
<223> OTHER INFORMATION: Asn or Glu
<220> FEATURE:
<221> NAME/KEY: MOD_RES
<222> LOCATION: (16)..(21)
<223> OTHER INFORMATION: Any amino acid

<400> SEQUENCE: 123

Xaa Xaa Xaa Xaa Xaa Xaa Xaa Xaa Xaa Xaa Leu Asp Leu Xaa Leu Xaa
 1               5                  10                  15

Xaa Xaa Xaa Xaa Xaa
            20

<210> SEQ ID NO 124
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(10)
<223> OTHER INFORMATION: This region may encompass 0-10 variable amino
      acids
<220> FEATURE:
<221> NAME/KEY: MOD_RES
<222> LOCATION: (15)
<223> OTHER INFORMATION: Phe or Ile
<220> FEATURE:
<221> NAME/KEY: MOD_RES
<222> LOCATION: (16)..(21)
<223> OTHER INFORMATION: Any amino acid

<400> SEQUENCE: 124

Xaa Xaa Xaa Xaa Xaa Xaa Xaa Xaa Xaa Xaa Phe Asp Leu Asn Xaa Xaa
 1               5                  10                  15
```

```
Xaa Xaa Xaa Xaa Xaa
            20

<210> SEQ ID NO 125
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(3)
<223> OTHER INFORMATION: This region may be Leu, Asp-Leu, or Leu-Asp-Leu
<220> FEATURE:
<221> NAME/KEY: MOD_RES
<222> LOCATION: (6)
<223> OTHER INFORMATION: Glu, Gln, or Asp
<220> FEATURE:
<221> NAME/KEY: MOD_RES
<222> LOCATION: (10)..(19)
<223> OTHER INFORMATION: This region may encompass 0-10 variable amino
      acids

<400> SEQUENCE: 125

Xaa Xaa Xaa Asp Leu Xaa Leu Arg Leu Xaa Xaa Xaa Xaa Xaa Xaa Xaa
  1               5                  10                  15

Xaa Xaa Xaa

<210> SEQ ID NO 126
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)
<223> OTHER INFORMATION: Glu, Gln, or Asp

<400> SEQUENCE: 126

Asp Leu Xaa Leu Arg Leu
  1               5

<210> SEQ ID NO 127
<211> LENGTH: 5
<212> TYPE: PRT
<213> ORGANISM: Arabidopsis thaliana

<400> SEQUENCE: 127

Leu Asp Leu Glu Leu
  1               5

<210> SEQ ID NO 128
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)
<223> OTHER INFORMATION: Asn or Glu

<400> SEQUENCE: 128

Leu Asp Leu Xaa Leu
  1               5
```

<210> SEQ ID NO 129
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)
<223> OTHER INFORMATION: Phe or Ile

<400> SEQUENCE: 129

Phe Asp Leu Asn Xaa
 1               5

<210> SEQ ID NO 130
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)
<223> OTHER INFORMATION: Glu, Gln, or Asp

<400> SEQUENCE: 130

Asp Leu Xaa Leu Arg Leu
 1               5

<210> SEQ ID NO 131
<211> LENGTH: 615
<212> TYPE: DNA
<213> ORGANISM: Arabidopsis thaliana
<220> FEATURE:
<221> NAME/KEY: CDS
<222> LOCATION: (1)..(615)

<400> SEQUENCE: 131

```
atg gag aga tca aac agc ata gag ttg agg aac agc ttc tat ggc cgt      48
Met Glu Arg Ser Asn Ser Ile Glu Leu Arg Asn Ser Phe Tyr Gly Arg
 1               5                  10                  15 gca aga act tca cca tgg agc tat gga gat tat gat aat tgc caa cag      96
Ala Arg Thr Ser Pro Trp Ser Tyr Gly Asp Tyr Asp Asn Cys Gln Gln
                20                  25                  30 gat cat gat tat ctt cta ggg ttt tca tgg cca cca aga tcc tac act     144
Asp His Asp Tyr Leu Leu Gly Phe Ser Trp Pro Pro Arg Ser Tyr Thr
            35                  40                  45 tgc agc ttc tgc aaa agg gaa ttc aga tcg gct caa gca ctt ggt ggc     192
Cys Ser Phe Cys Lys Arg Glu Phe Arg Ser Ala Gln Ala Leu Gly Gly
        50                  55                  60 cac atg aat gtt cac aga aga gac aga gca aga ctc aga tta caa cag     240
His Met Asn Val His Arg Arg Asp Arg Ala Arg Leu Arg Leu Gln Gln
    65                  70                  75                  80 tct cca tca tca tct tca aca cct tct cct cct tac cct aac cct aat     288
Ser Pro Ser Ser Ser Ser Thr Pro Ser Pro Pro Tyr Pro Asn Pro Asn
                85                  90                  95 tac tct tac tca acc atg gca aac tct cct cct cct cat cat tct cct     336
Tyr Ser Tyr Ser Thr Met Ala Asn Ser Pro Pro Pro His His Ser Pro
                100                 105                 110 cta acc cta ttt cca acc ctt tct cct cca tcc tca cca aga tat agg     384
Leu Thr Leu Phe Pro Thr Leu Ser Pro Pro Ser Ser Pro Arg Tyr Arg
            115                 120                 125
```

```
gca ggt ttg atc cgt tcc ttg agc ccc aag tca aaa cat aca cca gaa      432
Ala Gly Leu Ile Arg Ser Leu Ser Pro Lys Ser Lys His Thr Pro Glu
    130                 135                 140 aac gct tgt aag act aag aaa tca tct ctt tta gtg gag gct gga gag      480
Asn Ala Cys Lys Thr Lys Lys Ser Ser Leu Leu Val Glu Ala Gly Glu
145                 150                 155                 160 gct aca agg ttc acc agt aaa gat gct tgc aag atc ctg agg aat gat      528
Ala Thr Arg Phe Thr Ser Lys Asp Ala Cys Lys Ile Leu Arg Asn Asp
                165                 170                 175 gaa atc atc agc ttg gag ctt gag att ggt ttg att aac gaa tca gag      576
Glu Ile Ile Ser Leu Glu Leu Glu Ile Gly Leu Ile Asn Glu Ser Glu
            180                 185                 190 caa gat ctg gat cta gaa ctc cgt ttg ggt ttc gct taa                  615
Gln Asp Leu Asp Leu Glu Leu Arg Leu Gly Phe Ala
        195                 200
```

<210> SEQ ID NO 132
<211> LENGTH: 628
<212> TYPE: PRT
<213> ORGANISM: Arabidopsis thaliana

<400> SEQUENCE: 132

```
Met Met Phe Asn Glu Met Gly Met Cys Gly Asn Met Asp Phe Phe Ser
 1               5                  10                  15

Ser Gly Ser Leu Gly Glu Val Asp Phe Cys Pro Val Pro Gln Ala Glu
            20                  25                  30

Pro Asp Ser Ile Val Glu Asp Tyr Thr Asp Asp Glu Ile Asp Val
        35                  40                  45

Asp Glu Leu Glu Arg Arg Met Trp Arg Asp Lys Met Arg Leu Lys Arg
 50                  55                  60

Leu Lys Glu Gln Asp Lys Gly Lys Glu Gly Val Asp Ala Ala Lys Gln
 65                  70                  75                  80

Arg Gln Ser Gln Glu Gln Ala Arg Arg Lys Met Ser Arg Ala Gln
            85                  90                  95

Asp Gly Ile Leu Lys Tyr Met Leu Lys Met Met Glu Val Cys Lys Ala
            100                 105                 110

Gln Gly Phe Val Tyr Gly Ile Ile Pro Glu Asn Gly Lys Pro Val Thr
        115                 120                 125

Gly Ala Ser Asp Asn Leu Arg Glu Trp Trp Lys Asp Lys Val Arg Phe
    130                 135                 140

Asp Arg Asn Gly Pro Ala Ala Ile Thr Lys Tyr Gln Ala Glu Asn Asn
145                 150                 155                 160

Ile Pro Gly Ile His Glu Gly Asn Asn Pro Ile Gly Pro Thr Pro His
                165                 170                 175

Thr Leu Gln Glu Leu Gln Asp Thr Thr Leu Gly Ser Leu Leu Ser Ala
            180                 185                 190

Leu Met Gln His Cys Asp Pro Pro Gln Arg Arg Phe Pro Leu Glu Lys
        195                 200                 205

Gly Val Pro Pro Pro Trp Trp Pro Asn Gly Lys Glu Asp Trp Trp Pro
    210                 215                 220

Gln Leu Gly Leu Pro Lys Asp Gln Gly Pro Ala Pro Tyr Lys Lys Pro
225                 230                 235                 240

His Asp Leu Lys Lys Ala Trp Lys Val Gly Val Leu Thr Ala Val Ile
                245                 250                 255

Lys His Met Phe Pro Asp Ile Ala Lys Ile Arg Lys Leu Val Arg Gln
            260                 265                 270
```

```
Ser Lys Cys Leu Gln Asp Lys Met Thr Ala Lys Glu Ser Ala Thr Trp
        275                 280                 285

Leu Ala Ile Ile Asn Gln Glu Glu Ser Leu Ala Arg Glu Leu Tyr Pro
        290                 295                 300

Glu Ser Cys Pro Pro Leu Ser Leu Ser Gly Gly Ser Cys Ser Leu Leu
305                 310                 315                 320

Met Asn Asp Cys Ser Gln Tyr Asp Val Glu Gly Phe Glu Lys Glu Ser
                325                 330                 335

His Tyr Glu Val Glu Glu Leu Lys Pro Glu Lys Val Met Asn Ser Ser
            340                 345                 350

Asn Phe Gly Met Val Ala Lys Met His Asp Phe Pro Val Lys Glu Glu
        355                 360                 365

Val Pro Ala Gly Asn Ser Glu Phe Met Arg Lys Arg Lys Pro Asn Arg
    370                 375                 380

Asp Leu Asn Thr Ile Met Asp Arg Thr Val Phe Thr Cys Glu Asn Leu
385                 390                 395                 400

Gly Cys Ala His Ser Glu Ile Ser Arg Gly Phe Leu Asp Arg Asn Ser
                405                 410                 415

Arg Asp Asn His Gln Leu Ala Cys Pro His Arg Asp Ser Arg Leu Pro
            420                 425                 430

Tyr Gly Ala Ala Pro Ser Arg Phe His Val Asn Glu Val Lys Pro Val
        435                 440                 445

Val Gly Phe Pro Gln Pro Arg Pro Val Asn Ser Val Ala Gln Pro Ile
    450                 455                 460

Asp Leu Thr Gly Ile Val Pro Glu Asp Gly Gln Lys Met Ile Ser Glu
465                 470                 475                 480

Leu Met Ser Met Tyr Asp Arg Asn Val Gln Ser Asn Gln Thr Ser Met
                485                 490                 495

Val Met Glu Asn Gln Ser Val Ser Leu Leu Gln Pro Thr Val His Asn
            500                 505                 510

His Gln Glu His Leu Gln Phe Pro Gly Asn Met Val Glu Gly Ser Phe
        515                 520                 525

Phe Glu Asp Leu Asn Ile Pro Asn Arg Ala Asn Asn Asn Ser Ser
    530                 535                 540

Asn Asn Gln Thr Phe Phe Gln Gly Asn Asn Asn Asn Asn Val Phe
545                 550                 555                 560

Lys Phe Asp Thr Ala Asp His Asn Asn Phe Glu Ala Ala His Asn Asn
                565                 570                 575

Asn Asn Asn Ser Ser Gly Asn Arg Phe Gln Leu Val Phe Asp Ser Thr
            580                 585                 590

Pro Phe Asp Met Ala Ser Phe Asp Tyr Arg Asp Asp Met Ser Met Pro
        595                 600                 605

Gly Val Val Gly Thr Met Asp Gly Met Gln Gln Lys Gln Gln Asp Val
    610                 615                 620

Ser Ile Trp Phe
625

<210> SEQ ID NO 133
<211> LENGTH: 225
<212> TYPE: PRT
<213> ORGANISM: Nicotiana tabacum

<400> SEQUENCE: 133

Met Ala Val Lys Asn Lys Val Ser Asn Gly Asn Leu Lys Gly Gly Asn
1               5                   10                  15
```

Val Lys Thr Asp Gly Val Lys Glu Val His Tyr Arg Gly Val Arg Lys
            20                  25                  30

Arg Pro Trp Gly Arg Tyr Ala Ala Glu Ile Arg Asp Pro Gly Lys Lys
        35                  40                  45

Ser Arg Val Trp Leu Gly Thr Phe Asp Thr Ala Glu Glu Ala Ala Lys
    50                  55                  60

Ala Tyr Asp Thr Ala Ala Arg Glu Phe Arg Gly Pro Lys Ala Lys Thr
65                  70                  75                  80

Asn Phe Pro Ser Pro Thr Glu Asn Gln Ser Pro Ser His Ser Ser Thr
                85                  90                  95

Val Glu Ser Ser Ser Gly Glu Asn Gly Val His Ala Pro Pro His Ala
            100                 105                 110

Pro Leu Glu Leu Asp Leu Thr Arg Arg Leu Gly Ser Val Ala Ala Asp
        115                 120                 125

Gly Gly Asp Asn Cys Arg Arg Ser Gly Glu Val Gly Tyr Pro Ile Phe
    130                 135                 140

His Gln Gln Pro Thr Val Ala Val Leu Pro Asn Gly Gln Pro Val Leu
145                 150                 155                 160

Leu Phe Asp Ser Leu Trp Arg Ala Gly Val Val Asn Arg Pro Gln Pro
                165                 170                 175

Tyr His Val Thr Pro Met Gly Phe Asn Gly Val Asn Ala Gly Val Gly
            180                 185                 190

Pro Thr Val Ser Asp Ser Ser Ser Ala Val Glu Glu Asn Gln Tyr Asp
        195                 200                 205

Gly Lys Arg Gly Ile Asp Leu Asp Leu Asn Leu Ala Pro Pro Met Glu
    210                 215                 220

Phe
225

<210> SEQ ID NO 134
<211> LENGTH: 310
<212> TYPE: PRT
<213> ORGANISM: Arabidopsis thaliana

<400> SEQUENCE: 134

Met Asp Val Asp Val Phe Asn Gly Trp Gly Arg Pro Arg Phe Glu Asp
1               5                   10                  15

Glu Ser Leu Met Pro Pro Gly Phe Arg Phe His Pro Thr Asp Glu Glu
            20                  25                  30

Leu Ile Thr Tyr Tyr Leu Leu Lys Lys Val Leu Asp Ser Asn Phe Ser
        35                  40                  45

Cys Ala Ala Ile Ser Gln Val Asp Leu Asn Lys Ser Glu Pro Trp Glu
    50                  55                  60

Leu Pro Glu Lys Ala Lys Met Gly Glu Lys Glu Trp Tyr Phe Phe Thr
65                  70                  75                  80

Leu Arg Asp Arg Lys Tyr Pro Thr Gly Leu Arg Thr Asn Arg Ala Thr
                85                  90                  95

Glu Ala Gly Tyr Trp Lys Ala Thr Gly Lys Asp Arg Glu Ile Lys Ser
            100                 105                 110

Ser Lys Thr Lys Ser Leu Leu Gly Met Lys Lys Thr Leu Val Phe Tyr
        115                 120                 125

Lys Gly Arg Ala Pro Lys Gly Glu Lys Ser Cys Trp Val Met His Glu
    130                 135                 140

Tyr Arg Leu Asp Gly Lys Phe Ser Tyr His Tyr Ile Ser Ser Ser Ala

```
145                 150                 155                 160
Lys Asp Glu Trp Val Leu Cys Lys Val Cys Leu Lys Ser Gly Val Val
                165                 170                 175

Ser Arg Glu Thr Asn Leu Ile Ser Ser Ser Ser Ser Ala Val Thr
            180                 185                 190

Gly Glu Phe Ser Ser Ala Gly Ser Ala Ile Ala Pro Ile Ile Asn Thr
                195                 200                 205

Phe Ala Thr Glu His Val Ser Cys Phe Ser Asn Asn Ser Ala Ala His
            210                 215                 220

Thr Asp Ala Ser Phe His Thr Phe Leu Pro Ala Pro Pro Ser Leu
225                 230                 235                 240

Pro Pro Arg Gln Pro Arg His Val Gly Asp Gly Val Ala Phe Gly Gln
                245                 250                 255

Phe Leu Asp Leu Gly Ser Ser Gly Gln Ile Asp Phe Asp Ala Ala Ala
            260                 265                 270

Ala Ala Phe Phe Pro Asn Leu Pro Ser Leu Pro Pro Thr Val Leu Pro
            275                 280                 285

Pro Pro Pro Ser Phe Ala Met Tyr Gly Gly Gly Ser Pro Ala Val Ser
            290                 295                 300

Val Trp Pro Phe Thr Leu
305                 310
```

<210> SEQ ID NO 135
<211> LENGTH: 248
<212> TYPE: PRT
<213> ORGANISM: Arabidopsis thaliana

<400> SEQUENCE: 135

```
Met Glu Gly Ser Ser Lys Gly Leu Arg Lys Gly Ala Trp Thr Thr Glu
1               5                   10                  15

Glu Asp Ser Leu Leu Arg Gln Cys Ile Asn Lys Tyr Gly Glu Gly Lys
            20                  25                  30

Trp His Gln Val Pro Val Arg Ala Gly Leu Asn Arg Cys Arg Lys Ser
        35                  40                  45

Cys Arg Leu Arg Trp Leu Asn Tyr Leu Lys Pro Ser Ile Lys Arg Gly
    50                  55                  60

Lys Leu Ser Ser Asp Glu Val Asp Leu Leu Arg Leu His Arg Leu
65                  70                  75                  80

Leu Gly Asn Arg Trp Ser Leu Ile Ala Gly Arg Leu Pro Gly Arg Thr
                85                  90                  95

Ala Asn Asp Val Lys Asn Tyr Trp Asn Thr His Leu Ser Lys Lys His
            100                 105                 110

Glu Pro Cys Cys Lys Ile Lys Met Lys Lys Arg Asp Ile Thr Pro Ile
        115                 120                 125

Pro Thr Thr Pro Ala Leu Lys Asn Asn Val Tyr Lys Pro Arg Pro Arg
    130                 135                 140

Ser Phe Thr Val Asn Asn Asp Cys Asn His Leu Asn Ala Pro Pro Lys
145                 150                 155                 160
```

```
Val Asp Val Asn Pro Pro Cys Leu Gly Leu Asn Ile Asn Asn Val Cys
            165                 170                 175

Asp Asn Ser Ile Ile Tyr Asn Lys Asp Lys Lys Asp Gln Leu Val
        180                 185                 190

Asn Asn Leu Ile Asp Gly Asp Asn Met Trp Leu Glu Lys Phe Leu Glu
            195                 200                 205

Glu Ser Gln Glu Val Asp Ile Leu Val Pro Glu Ala Thr Thr Thr Glu
        210                 215                 220

Lys Gly Asp Thr Leu Ala Phe Asp Val Asp Gln Leu Trp Ser Leu Phe
225                 230                 235                 240

Asp Gly Glu Thr Val Lys Phe Asp
            245

<210> SEQ ID NO 136
<211> LENGTH: 219
<212> TYPE: PRT
<213> ORGANISM: Arabidopsis thaliana

<400> SEQUENCE: 136

Met Arg Met Thr Arg Asp Gly Lys Glu His Glu Tyr Lys Lys Gly Leu
 1               5                  10                  15

Trp Thr Val Glu Glu Asp Lys Ile Leu Met Asp Tyr Val Arg Thr His
            20                  25                  30

Gly Gln Gly His Trp Asn Arg Ile Ala Lys Lys Thr Gly Leu Lys Arg
        35                  40                  45

Cys Gly Lys Ser Cys Arg Leu Arg Trp Met Asn Tyr Leu Ser Pro Asn
    50                  55                  60

Val Asn Arg Gly Asn Phe Thr Asp Gln Glu Glu Asp Leu Ile Ile Arg
65                  70                  75                  80

Leu His Lys Leu Leu Gly Asn Arg Trp Ser Leu Ile Ala Lys Arg Val
                85                  90                  95

Pro Gly Arg Thr Asp Asn Gln Val Lys Asn Tyr Trp Asn Thr His Leu
            100                 105                 110

Ser Lys Lys Leu Gly Leu Gly Asp His Ser Thr Ala Val Lys Ala Ala
        115                 120                 125

Cys Gly Val Glu Ser Pro Pro Ser Met Ala Leu Ile Thr Thr Thr Ser
    130                 135                 140

Ser Ser His Gln Glu Ile Ser Gly Gly Lys Asn Ser Thr Leu Arg Phe
145                 150                 155                 160

Asp Thr Leu Val Asp Glu Ser Lys Leu Lys Pro Lys Ser Lys Leu Val
                165                 170                 175

His Ala Thr Pro Thr Asp Val Glu Val Ala Ala Thr Val Pro Asn Leu
            180                 185                 190

Phe Asp Thr Phe Trp Val Leu Glu Asp Asp Phe Glu Leu Ser Ser Leu
        195                 200                 205

Thr Met Met Asp Phe Thr Asn Gly Tyr Cys Leu
210                 215
```